US012642809B2

(12) United States Patent
Le-Lau

(10) Patent No.: US 12,642,809 B2
(45) Date of Patent: *Jun. 2, 2026

(54) FUCOSYLATION AND IMMUNE MODULATION IN CANCER

(71) Applicant: H. LEE MOFFITT CANCER CENTER AND RESEARCH INSTITUTE, INC., Tampa, FL (US)

(72) Inventor: Eric Le-Lau, Tampa, FL (US)

(73) Assignee: H. Lee Moffitt Cancer Center and Research Institute, Tampa, FL (US)

( * ) Notice: Subject to any disclaimer, the term of this patent is extended or adjusted under 35 U.S.C. 154(b) by 1053 days.

This patent is subject to a terminal disclaimer.

(21) Appl. No.: 17/635,847

(22) PCT Filed: Aug. 17, 2020

(86) PCT No.: PCT/US2020/046694

§ 371 (c)(1),
(2) Date: Feb. 16, 2022

(87) PCT Pub. No.: WO2021/034774

PCT Pub. Date: Feb. 25, 2021

(65) Prior Publication Data

US 2022/0305038 A1 Sep. 29, 2022

Related U.S. Application Data

(60) Provisional application No. 62/887,814, filed on Aug. 16, 2019.

(51) Int. Cl.
*A61K 31/7004* (2006.01)
*A61K 40/15* (2025.01)
(Continued)

(52) U.S. Cl.
CPC .......... *A61K 31/7004* (2013.01); *A61K 40/15* (2025.01); *A61K 40/4271* (2025.01);
(Continued)

(58) Field of Classification Search
CPC ................ A61K 31/7004; A61K 40/15; A61K 40/4271; A61K 2239/57; A61K 2039/876;
(Continued)

(56) References Cited

U.S. PATENT DOCUMENTS 3,610,795 A     10/1971  Antoine
4,946,830 A  *   8/1990  Pulverer ................ A61K 31/70
                                                            514/23

(Continued)

FOREIGN PATENT DOCUMENTS

WO         2018/226701 A1     12/2018
WO         2019/075449 A1      4/2019

OTHER PUBLICATIONS

Lau E, Feng Y, Claps G, et al. The transcription factor ATF2 promotes melanoma metastasis by suppressing protein fucosylation. Sci Signal. 2015;8(406):ra124. (Year: 2015).*

(Continued)

*Primary Examiner* — Joanne Hama
*Assistant Examiner* — Hannah Sunshine
(74) *Attorney, Agent, or Firm* — Meunier Carlin & Curfman LLC

(57)                    ABSTRACT

Disclosed are methods for treating a cancer and/or modulating immune CD4+ T cell mediated therapies comprising administering to a subject a fucose. In one aspect, disclosed herein are methods of modulating major histocompatibility complex II human lymphocyte antigen (HLA)-DRB 1 expression on the surface of a cell comprising contacting the cell with an agent that modulates the amount of fucosylation on the cell; wherein an increase in fucosylation increases (Continued)

surface expression of HLA-DRB 1; and wherein a decrease in fucosylation decreases the surface expression of HLA-DRB 1.

20 Claims, 27 Drawing Sheets

Specification includes a Sequence Listing.

(51) Int. Cl.

| | |
|---|---|
| *A61K 40/42* | (2025.01) |
| *A61P 35/00* | (2006.01) |
| *A61P 37/04* | (2006.01) |
| *C07K 16/30* | (2006.01) |
| *C12N 5/0783* | (2010.01) |

(52) U.S. Cl.
CPC .............. *A61P 35/00* (2018.01); *A61P 37/04* (2018.01); *C07K 16/30* (2013.01); *C12N 5/0636* (2013.01); *A61K 2239/57* (2023.05)

(58) Field of Classification Search
CPC .... A61K 31/702; A61K 31/715; A61K 39/39; A61P 35/00; A61P 37/04; C07K 16/30; C12N 5/0636
See application file for complete search history.

(56) References Cited

U.S. PATENT DOCUMENTS

| | | | | |
|---|---|---|---|---|
| 11,891,644 B2 * | 2/2024 | Okeley | .............. | A61K 31/7024 |
| 2015/0273033 A1 | 10/2015 | Bosch et al. | | |
| 2018/0353524 A1 | 12/2018 | Gardai et al. | | |

OTHER PUBLICATIONS

Wei SC, Duffy CR, Allison JP. Fundamental Mechanisms of Immune Checkpoint Blockade Therapy. Cancer Discov. 2018;8(9):1069-1086. (Year: 2018).*

Cancer risk and prevention. American Cancer Society. Accessed Jan. 22, 2025. https://www.cancer.org/cancer/risk-prevention.html. Internet—Wayback Machine (Year: 2025).*

Li J, Hsu HC, Ding Y, et al. Inhibition of fucosylation reshapes inflammatory macrophages and suppresses type II collagen-induced arthritis. Arthritis Rheumatol. 2014;66(9):2368-2379. (Year: 2014).*

Shan M, Yang D, Dou H, Zhang L. Fucosylation in cancer biology and its clinical applications. Prog Mol Biol Transl Sci. 2019;162:93-119. (Year: 2019).*

Alatrash G, Qiao N, Zhang M, et al. Fucosylation Enhances the Efficacy of Adoptively Transferred Antigen-Specific Cytotoxic T Lymphocytes. Clin Cancer Res. 2019;25(8):2610-2620. (Year: 2019).*

Okada M, Chikuma S, Kondo T, et al. Blockage of Core Fucosylation Reduces Cell-Surface Expression of PD-1 and Promotes Anti-tumor Immune Responses of T Cells. Cell Rep. 2017;20(5):1017-1028. (Year: 2017).*

Liang W, Mao S, Sun S, et al. Core Fucosylation of the T Cell Receptor Is Required for T Cell Activation. Front Immunol. 2018;9:78. (Year: 2018).*

Senter, Peter D., et al. "Generation of 5-fluorouracil from 5-fluorocytosine by monoclonal antibody-cytosine deaminase conjugates." Bioconjugate chemistry 2.6 (1991): 447-451.

Bagshawe, K. D. "Towards generating cytotoxic agents at cancer sites. The First Bagshawe Lecture." Br. J. Cancer 60 (1989): 275-281.

Bagshawe, K. D., et al. "A cytotoxic agent can be generated selectively at cancer sites." British journal of cancer 58.6 (1988): 700-703.

Senter, Peter D., et al. "Generation of cytotoxic agents by targeted enzymes." Bioconjugate chemistry 4.1 (1993): 3-9.

Battelli, M. G., et al. "T lymphocyte killing by a xanthine-oxidase-containing immunotoxin." Cancer Immunology, Immunotherapy 35.6 (1992): 421-425.

Pietersz, Geoffrey A., and Ian FC McKenzie. "Antibody conjugates for the treatment of cancer." Immunological reviews 129.1 (1992): 57-80.

Roffler, Steven R., et al. "Anti-neoplastic glucuronide prodrug treatment of human tumor cells targeted with a monoclonal antibody-enzyme conjugate." Biochemical pharmacology 42.10 (1991): 2062-2065.

Hughes, Brenda J., et al. "Monoclonal antibody targeting of liposomes to mouse lung in vivo." Cancer research 49.22 (1989): 6214-6220.

Litzinger, David C., and Leaf Huang. "Biodistribution and immunotargetability of ganglioside-stabilized dioleoylphosphatidylethanolamine liposomes." Biochimica et Biophysica Acta (BBA)—Biomembranes 1104.1 (1992): 179-187.

Brown, Valerie I., and Mark I. Greene. "Molecular and cellular mechanisms of receptor-mediated endocytosis." DNA and cell biology 10.6 (1991): 399-409.

Handbook of Monoclonal Antibodies, Ferrone et al., eds., Noges Publications, Park Ridge, N.J., (1985) ch. 22 and pp. 303-357.

Smith et al., Antibodies in Human Diagnosis and Therapy, Haber et al., eds., Raven Press, New York (1977) pp. 365-389.

Abe, S., et al. Safety evaluation of excessive ingestion of mozuku fucoidan in human. J Food Sci 78, T648-651 (2013).

Alam, M.S. Proximity Ligation Assay (PLA). Curr Protoc Immunol 123, e58 (2018).

Alatrash, G., et al. Fucosylation Enhances the Efficacy of Adoptively Transferred Antigen-Specific Cytotoxic T Lymphocytes. Clin Cancer Res 25, 2610-2620 (2019).

Araya, N., et al. Fucoidan therapy decreases the proviral load in patients with human T-lymphotropic virus type-1-associated neurological disease. Antivir Ther 16, 89-98 (2011).

Barber, L.D., et al. Unusual uniformity of the N-linked oligosaccharides of HLA-A,—B, and—C glycoproteins. J Immunol 156, 3275-3284 (1996).

Becker, D.J. & Lowe, J.B. Fucose: biosynthesis and biological function in mammals. Glycobiology 13, 41R-53R (2003).

Chacon, J.A., et al. Manipulating the tumor microenvironment ex vivo for enhanced expansion of tumor-infiltrating lymphocytes for adoptive cell therapy. Clin Cancer Res 21, 611-621 (2015).

Chang, C.S., Brossay, L., Kronenberg, M. & Kane, K.P. The murine nonclassical class I major histocompatibility complex-like CD1.1 molecule protects target cells from lymphokine-activated killer cell cytolysis. J Exp Med 189, 483-491 (1999).

Choi, S.S., et al. Safety evaluation of the human-identical milk monosaccharide, 1-fucose. Regul Toxicol Pharmacol 72, 39-48 (2015).

Etzioni, A. & Tonetti, M. Fucose supplementation in leukocyte adhesion deficiency type II. Blood 95, 3641-3643 (2000).

Gellrich, F.F., Schmitz, M., Beissert, S. & Meier, F. Anti-PD-1 and Novel Combinations in the Treatment of Melanoma—An Update. J Clin Med 9(2020).

Hodis, E., et al. A landscape of driver mutations in melanoma. Cell 150, 251-263 (2012).

Hsu, H.Y. & Hwang, P.A. Clinical applications of fucoidan in translational medicine for adjuvant cancer therapy. Clin Transl Med 8, 15 (2019).

Johnson, D.B., et al. Melanoma-specific MHC-II expression represents a tumour-autonomous phenotype and predicts response to anti-PD-1/PD-L1 therapy. Nat Commun 7, 10582 (2016).

Kennedy, R. & Celis, E. Multiple roles for CD4+ T cells in anti-tumor immune responses. Immunol Rev 222, 129-144 (2008).

Knight, D.A., et al. Host immunity contributes to the anti-melanoma activity of BRAF inhibitors. J Clin Invest 123, 1371-1381 (2013).

Kramer, A., Green, J., Pollard, J., Jr. & Tugendreich, S. Causal analysis approaches in Ingenuity Pathway Analysis. Bioinformatics 30, 523-530 (2014).

Lau, E., et al. The transcription factor ATF2 promotes melanoma metastasis by suppressing protein fucosylation. Sci Signal 8, ra124 (2015).

(56)　　　　　References Cited

OTHER PUBLICATIONS

Lenertz, L. Y., et al. Mutation of putative N-linked glycosylation sites on the human nucleotide receptor P2X7 reveals a key residue important for receptor function. Biochemistry 49, 4611-4619 (2010).
Liang, W., et al. Core Fucosylation of the T Cell Receptor Is Required for T Cell Activation. Front Immunol 9, 78 (2018).
Maletzki, C., et al. NSG mice as hosts for oncological precision medicine. Lab Invest 100, 27-37 (2020).
Marquardt, T., et al. Correction of leukocyte adhesion deficiency type II with oral fucose. Blood 94, 3976-3985 (1999).
Marth, J.D. & Grewal, P.K. Mammalian glycosylation in immunity. Nat Rev Immunol 8, 874-887 (2008).
Mori, N., Nakasone, K., Tomimori, K. & Ishikawa, C. Beneficial effects of fucoidan in patients with chronic hepatitis C virus infection. World J Gastroenterol 18, 2225-2230 (2012).
Okada, M., et al. Blockage of Core Fucosylation Reduces Cell-Surface Expression of PD-1 and Promotes Anti-tumor Immune Responses of T Cells. Cell Rep 20, 1017-1028 (2017).
Orczyk-Pawilowicz, M., Augustyniak, D., Hirnle, L. & Katnik-Prastowska, I. Lectin-based analysis of fucose and sialic acid expressions on human amniotic IgA during normal pregnancy. Glycoconj J 30, 599-608 (2013).
Pandey, A., et al. Glycosylation of Specific Notch EGF Repeats by O-Fut1 and Fringe Regulates Notch Signaling in Drosophila. Cell Rep 29, 2054-2066 e2056 (2019).
Raulet, D.H., et al. Specificity, tolerance and developmental regulation of natural killer cells defined by expression of class I-specific Ly49 receptors. Immunol Rev 155, 41-52 (1997).
Rillahan, C.D., et al. Global metabolic inhibitors of sialyl- and fucosyltransferases remodel the glycome. Nat Chem Biol 8, 661-668 (2012).
Rock, K.L., Reits, E. & Neefjes, J. Present Yourself! By MHC Class I and MHC Class II Molecules. Trends Immunol 37, 724-737 (2016).
Rodig, S.J., et al. MHC proteins confer differential sensitivity to CTLA-4 and PD-1 blockade in untreated metastatic melanoma. Sci Transl Med 10(2018).

Rossjohn, J., et al. T cell antigen receptor recognition of antigen-presenting molecules. Annu Rev Immunol 33, 169-200 (2015).
Rubio, G., et al. Cross-linking of MHC class I molecules on human NK cells inhibits NK cell function, segregates MHC I from the NK cell synapse, and induces intracellular phosphotyrosines. J Leukoc Biol 76, 116-124 (2004).
Spitzer, M.H., et al. Systemic Immunity Is Required for Effective Cancer Immunotherapy. Cell 168, 487-502 e415 (2017).
Steentoft, C., et al. Precision mapping of the human O-GalNAc glycoproteome through SimpleCell technology. EMBO J 32, 1478-1488 (2013).
Stern, L.J., et al. Crystal structure of the human class II MHC protein HLA-DR1 complexed with an influenza virus peptide. Nature 368, 215-221 (1994).
Talmadge, J.E. & Fidler, I.J. Enhanced metastatic potential of tumor cells harvested from spontaneous metastases of heterogeneous murine tumors. J Natl Cancer Inst 69, 975-980 (1982).
Topalian, S.L., et al. Melanoma-specific CD4+ T lymphocytes recognize human melanoma antigens processed and presented by Epstein-Barr virus-transformed B cells. Int J Cancer 58, 69-79 (1994).
Tsiakas, K., et al. Mutation of the glycosylated asparagine residue 286 in human CLN2 protein results in loss of enzymatic activity. Glycobiology 14, 1C-5C (2004).
Wang, Y., et al. Biological Activities of Fucoidan and the Factors Mediating Its Therapeutic Effects: A Review of Recent Studies. Mar Drugs 17(2019).
Weber, J.S., et al. Nivolumab versus chemotherapy in patients with advanced melanoma who progressed after anti-CTLA-4 treatment (CheckMate 037): a randomised, controlled, open-label, phase 3 trial. Lancet Oncol 16, 375-384 (2015).
Wei, W., et al. Molecular mechanisms of missense mutations that generate ectopic N-glycosylation sites in coagulation factor VIII. Biochem J 475, 873-886 (2018).
International Search Report and Written Opinion in PCT/US2020/0466694. Mailed Dec. 7, 2020. 13 pages.
Alatrash, et al. "Fucosylation Enhances the Efficacy of Adoptively Transferred Antigen-Specific Cytotoxic T Lymphocytes," Clin Cancer Res, Jan. 15, 2019. vol. 25, pp. 2610-2620.

* cited by examiner

FIG. 4A
FIG. 4B
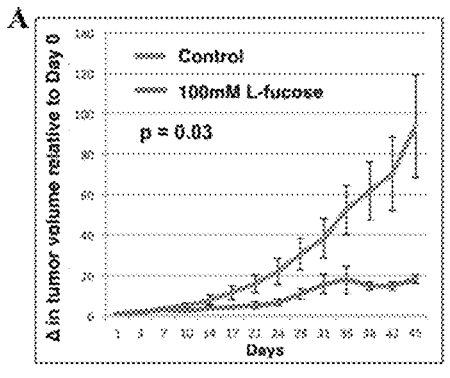
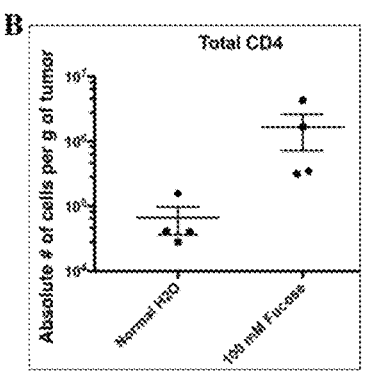
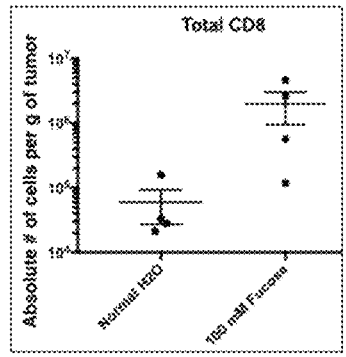
FIG. 4C
FIG. 4D
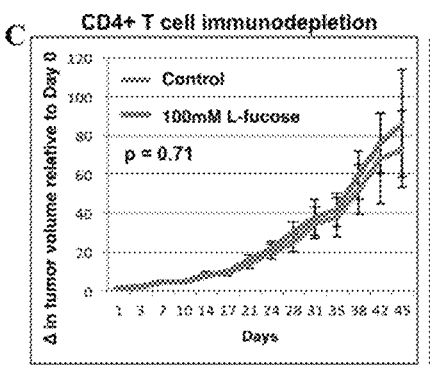
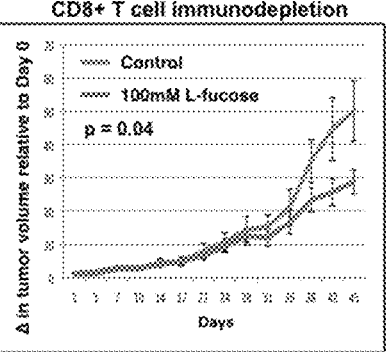
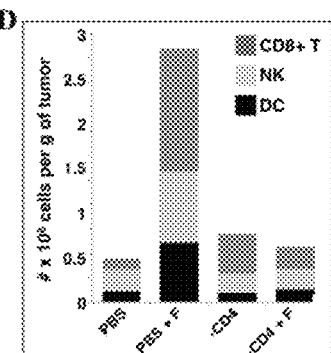

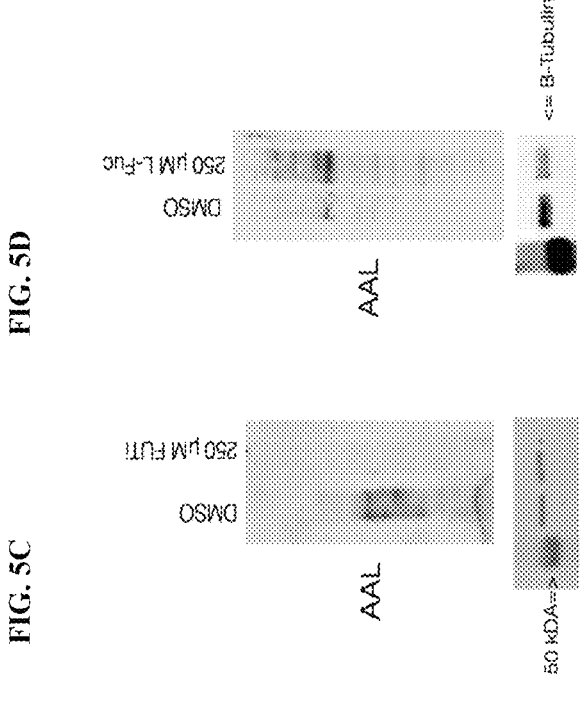
FIG. 5D
FIG. 5C
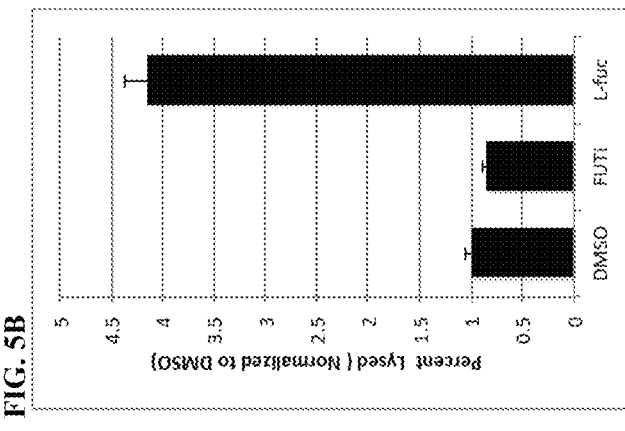
FIG. 5B
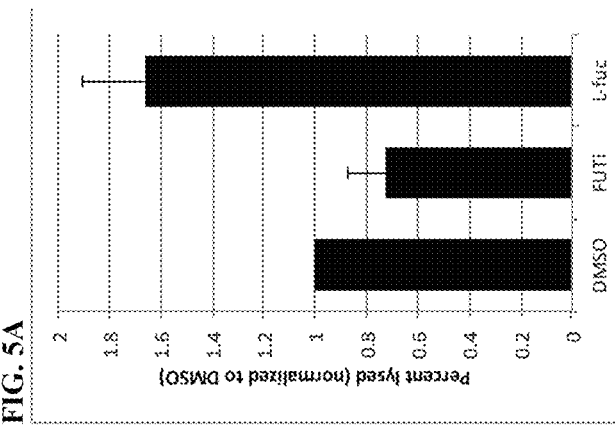
FIG. 5A

FIG. 6A
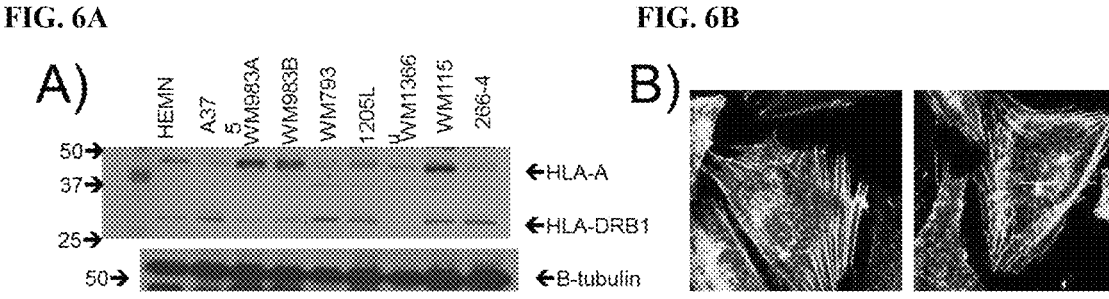
FIG. 6B
FIG. 6C
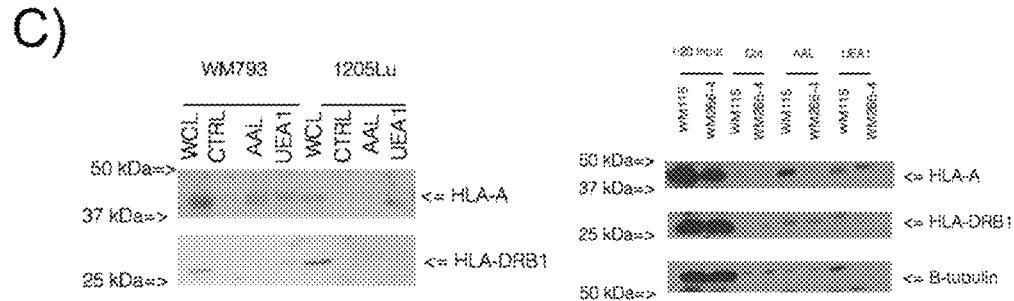
FIG. 7
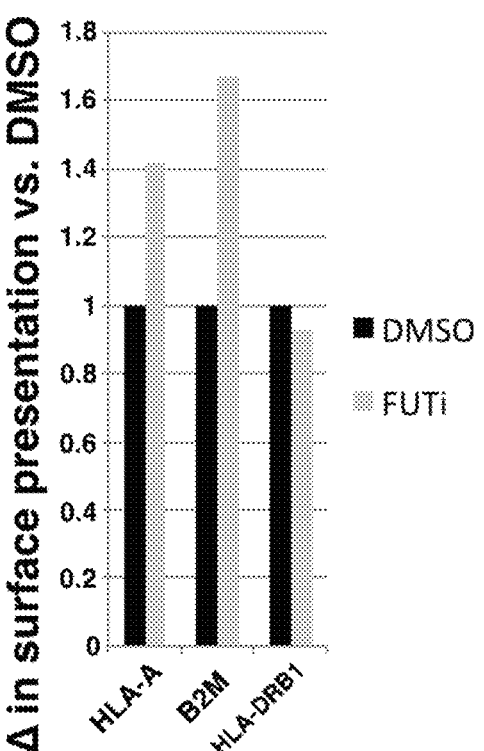

FIG. 8A
FIG. 8B
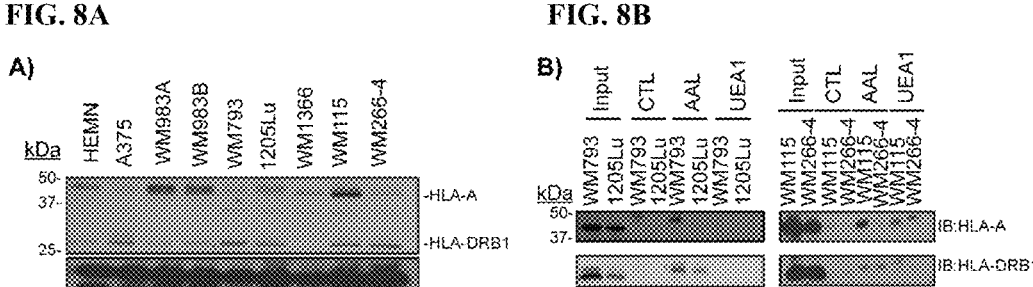
FIG. 8C
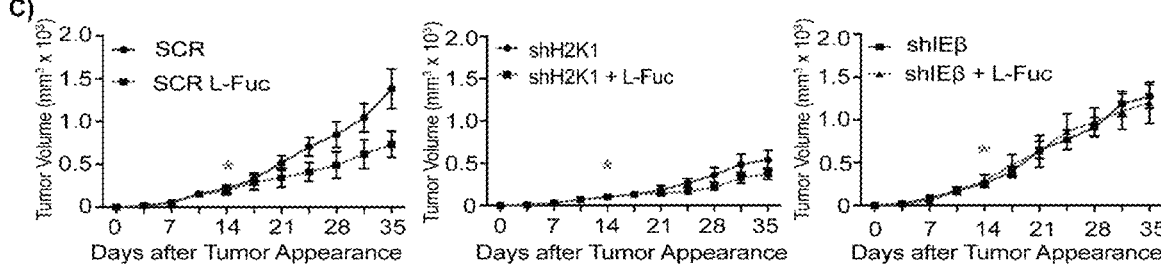

FIG. 9A                                              FIG. 9B
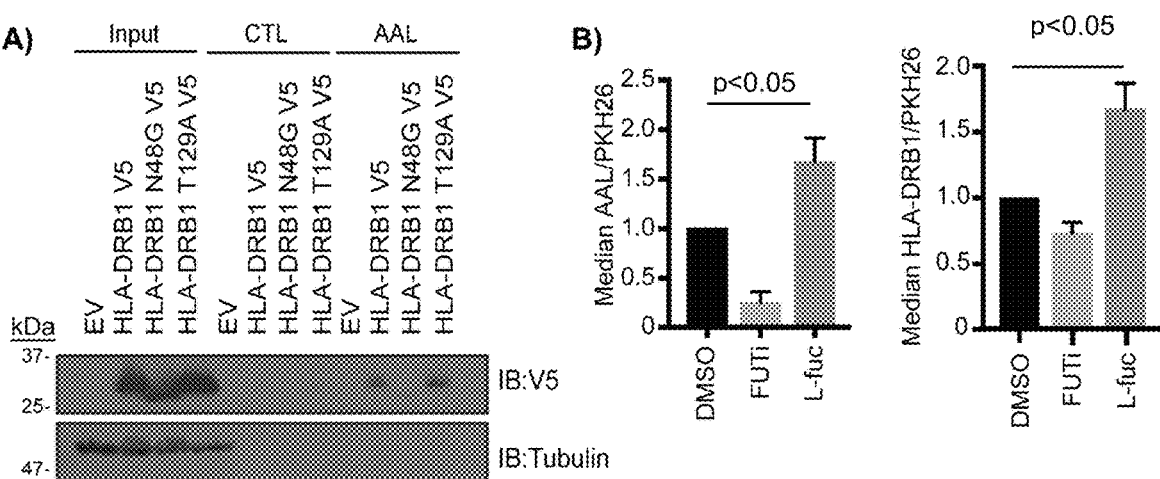
FIG. 10A                                             FIG. 10B
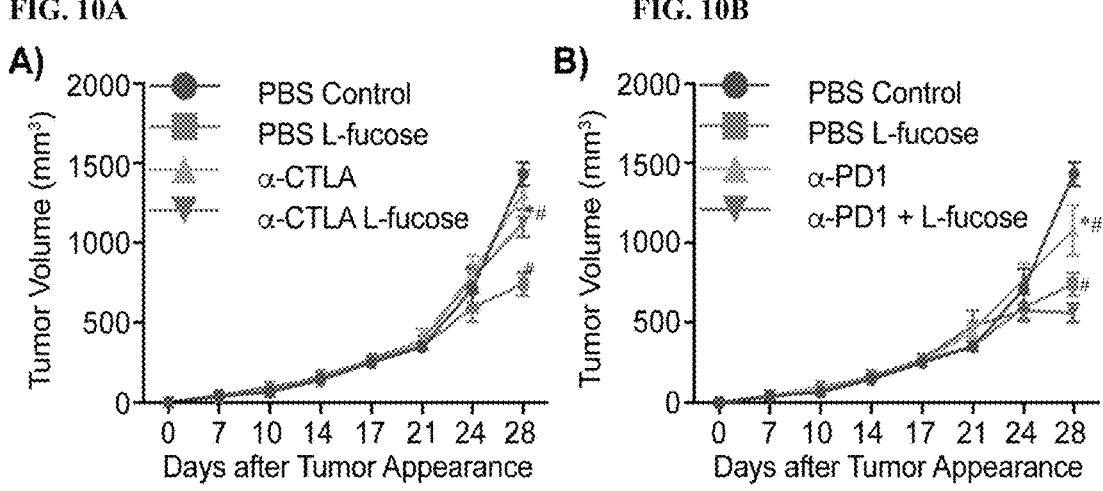

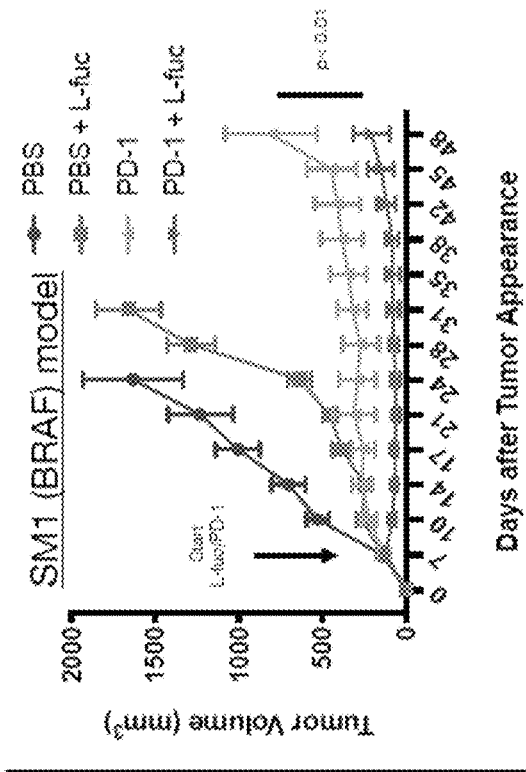
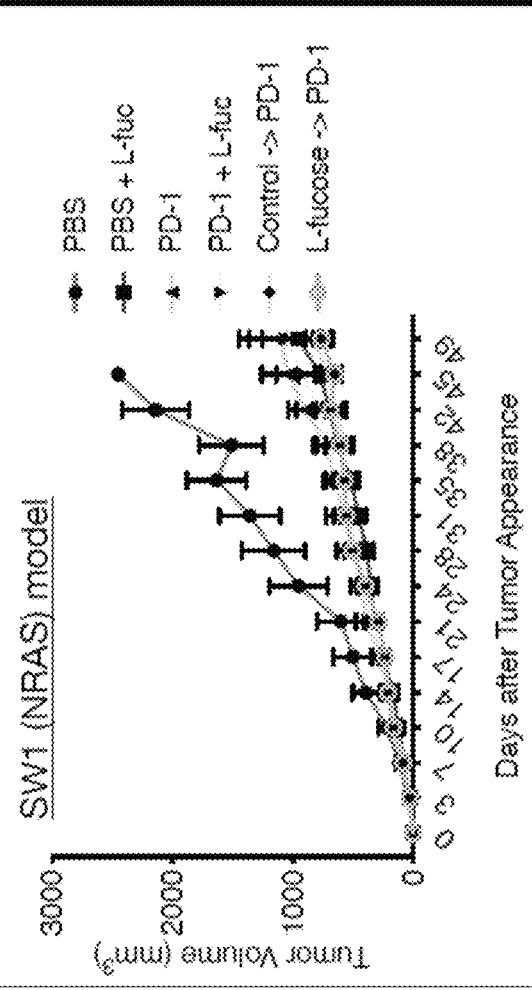
FIG. 11

FIG. 14A    FIG. 14B    FIG. 14C
FIG. 14D    FIG. 14E    FIG. 14F
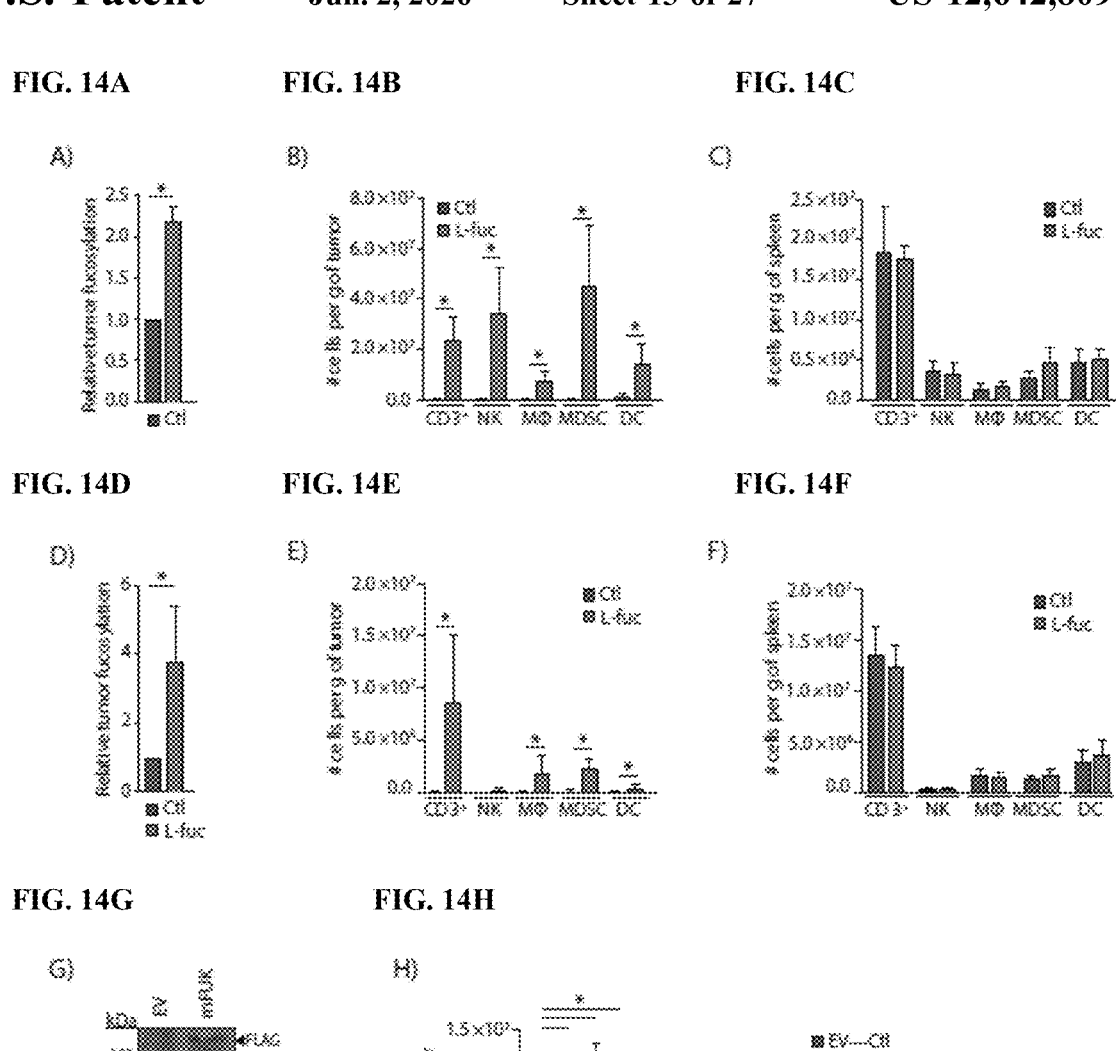
FIG. 14G    FIG. 14H
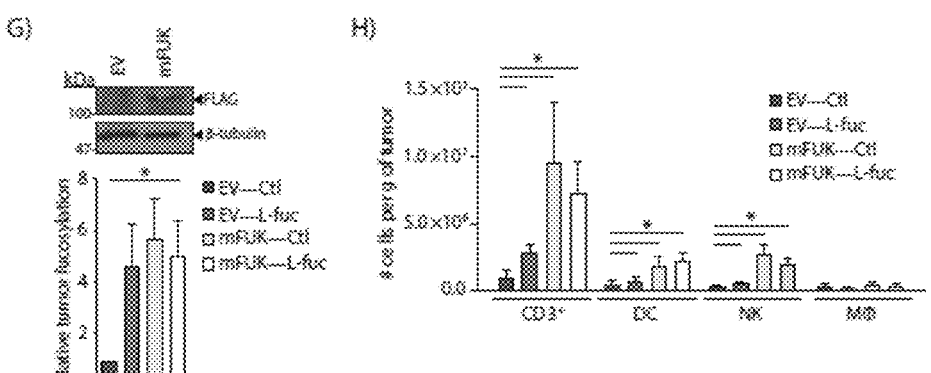
FIG. 14I    FIG. 14J
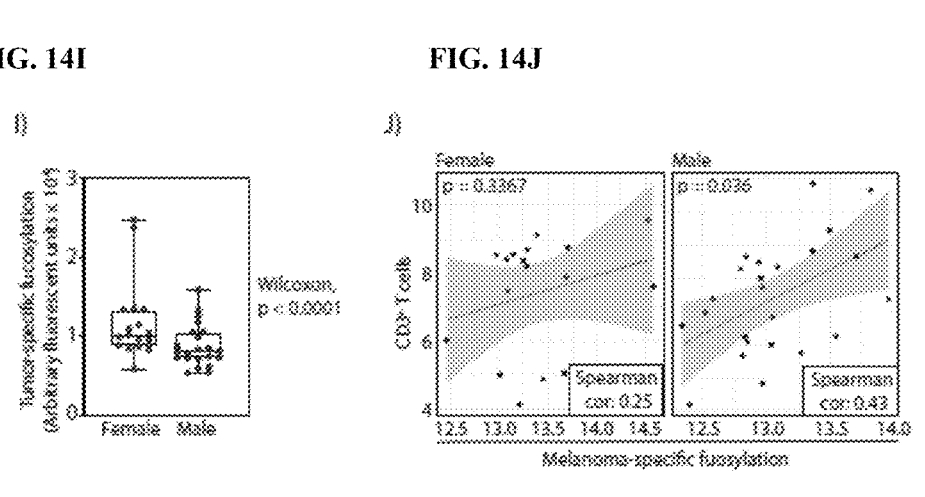

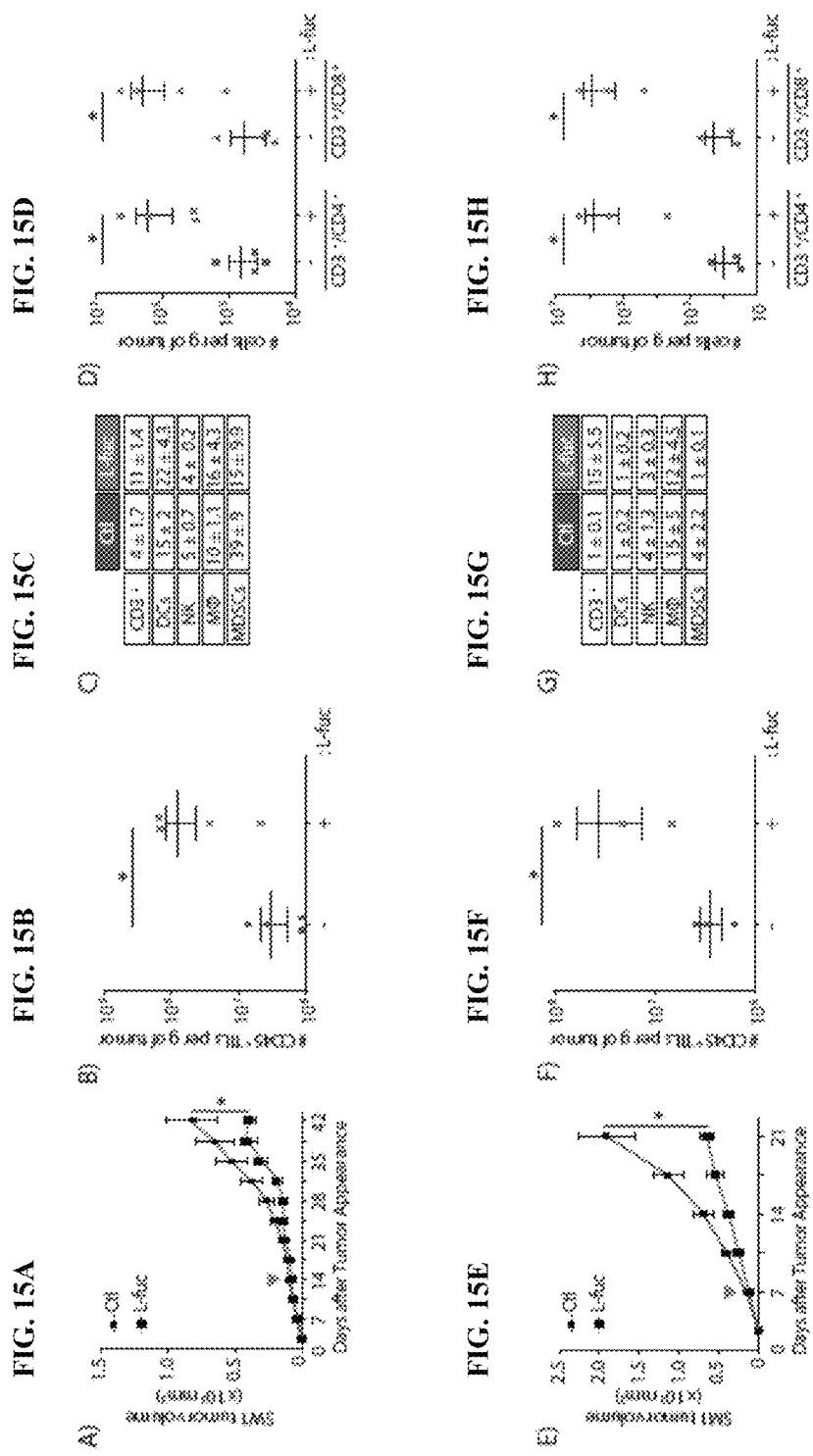

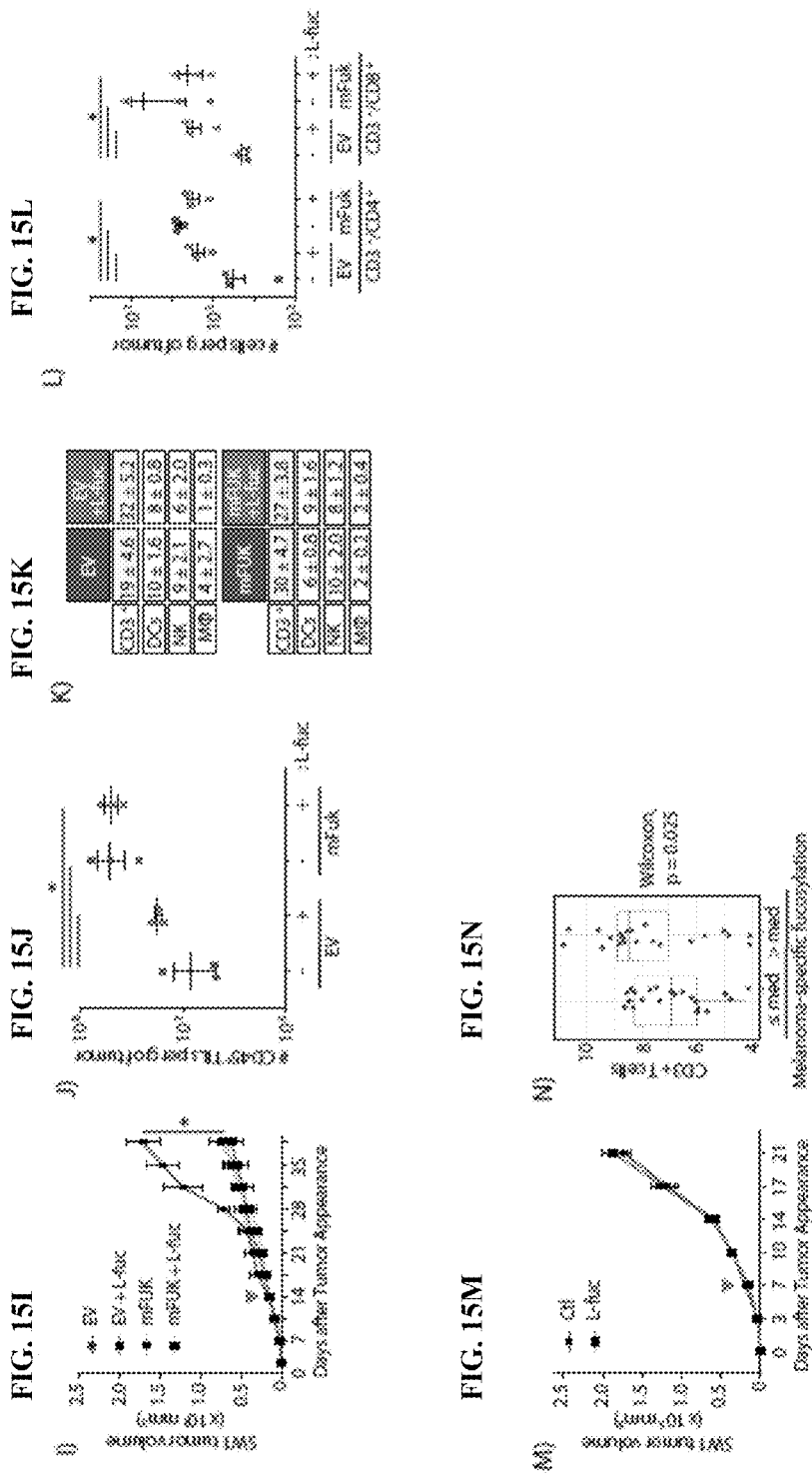

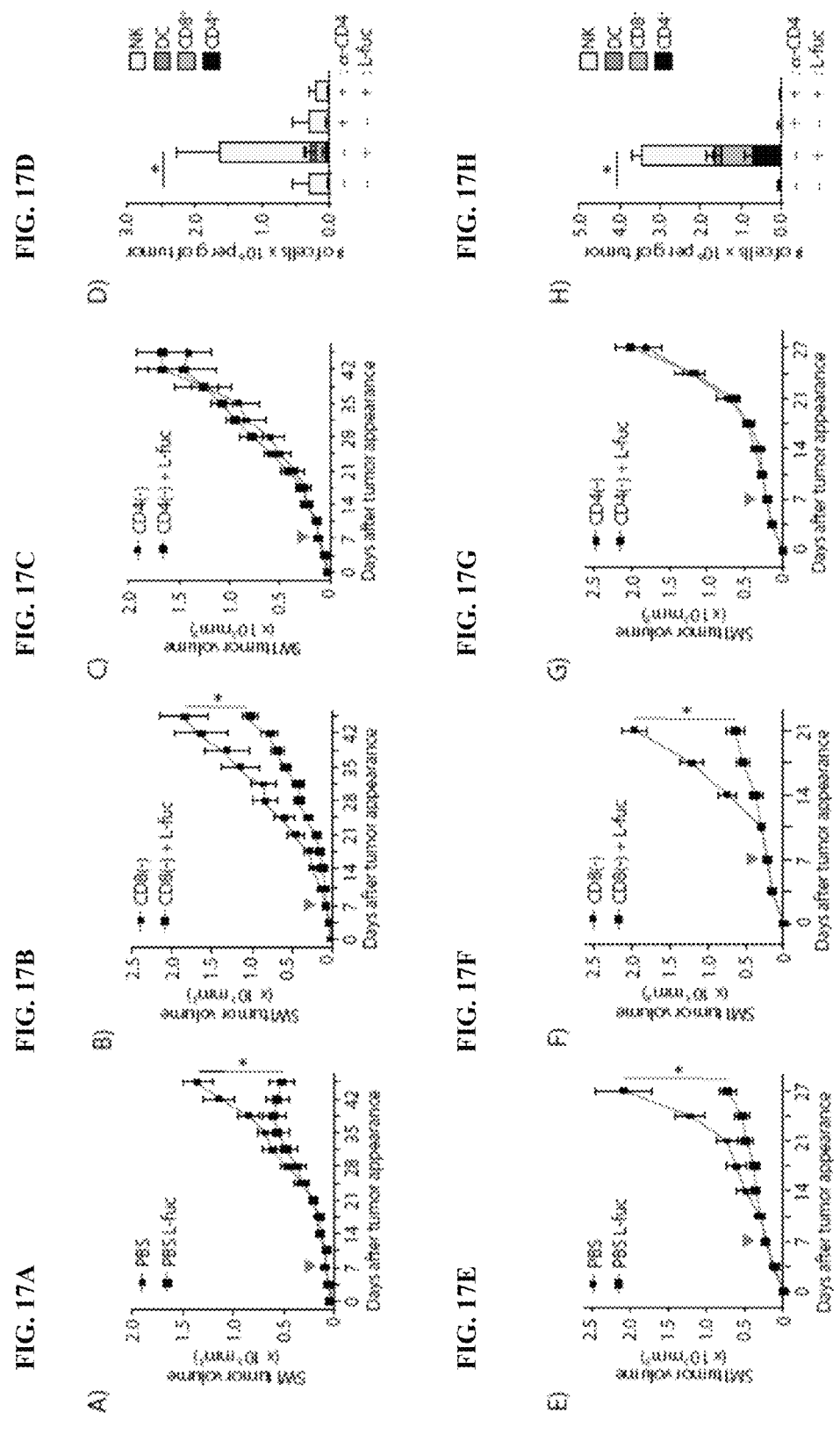

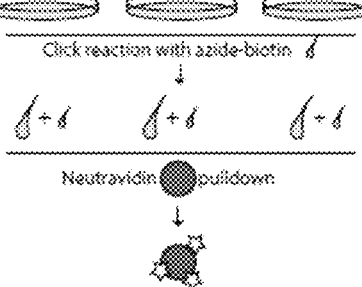

Fucosylated mass spectrometry

Metabolically label: 6-alkynyl-L-fucose    (96h)

EV        shFUK        FUK o/e

Click reaction with azide-biotin

Neutravidin pulldown

1) LC-MS/MS

2) Filtering:
-exclude hits increased by shFUK vs. FUK o/e
-exclude hits increased by EV vs. FUK o/e
-exclude MS/MS peptide count <10
-include FC ≥ 1.5

3) IPA pathway analysis

Top 20 pathways identified by Ingenuity Pathway Analysis

EIF2 signaling
Regulation of eIF4 and p70S6K signaling
mTOR signaling
Unfolded protein response
Protein ubiquitination pathway
Aldosterone signaling in epithelial cells
Glycolysis I
Gluconeogenesis I
Phagosome maturation
NRF2-mediated oxidative stress response
BAG2 signaling
Remodeling of epithelial adherens junctions
Glutaryl-CoA degradation
Ditrain signaling pathway
Antigen presentation pathway
Tryptophan degradation III
TCA cycle II
eNOS signaling
Purine nucleotides de novo biosynthesis II
Germ cell-Sertoli cell junction signaling

| I immune-related cluster | |
|---|---|
| CANX | -3.049 |
| HLA-DRB1 | -1.437 |
| PDIA3 | -1.136 |
| CALR | -0.962 |
| HLA-A | -0.212 |

| 11 plasma membrane proteins | |
|---|---|
| STRAP | -2.096 |
| SPTBN1 | -1.962 |
| CSPG4 | -1.906 |
| TFRC | -1.688 |
| ATP1A1 | -1.59 |
| HLA-DRB1 | -1.437 |
| AIMP2 | -0.981 |
| ANXA6 | -0.739 |
| CLTC | -0.314 |
| SLC3A2 | -0.224 |
| HLA-A | -0.212 |

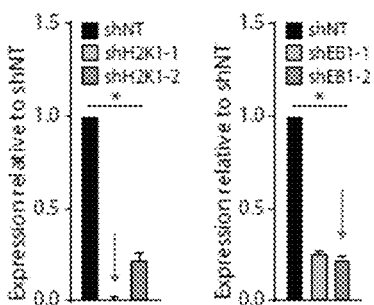

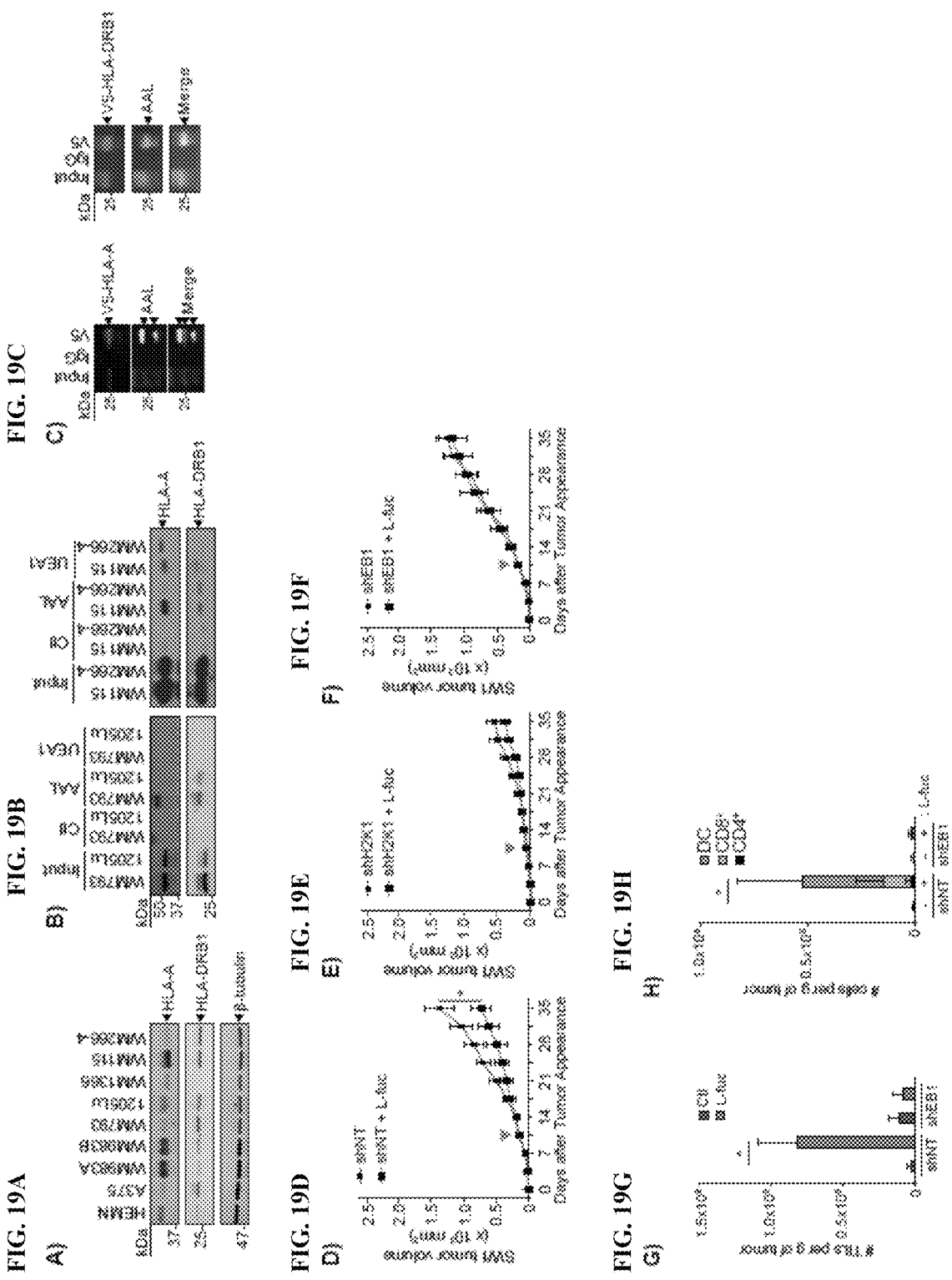

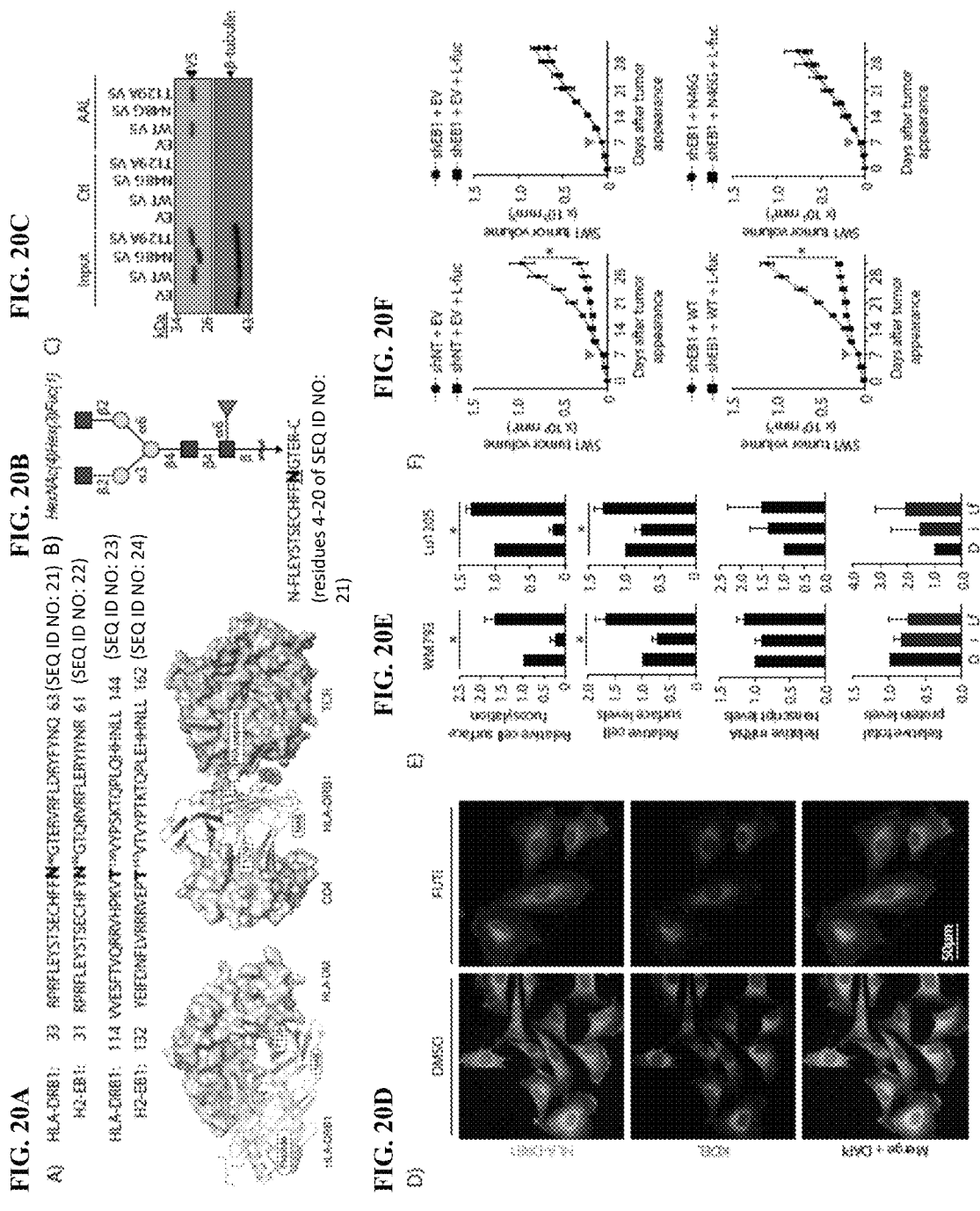

FIG. 21A
FIG. 21B
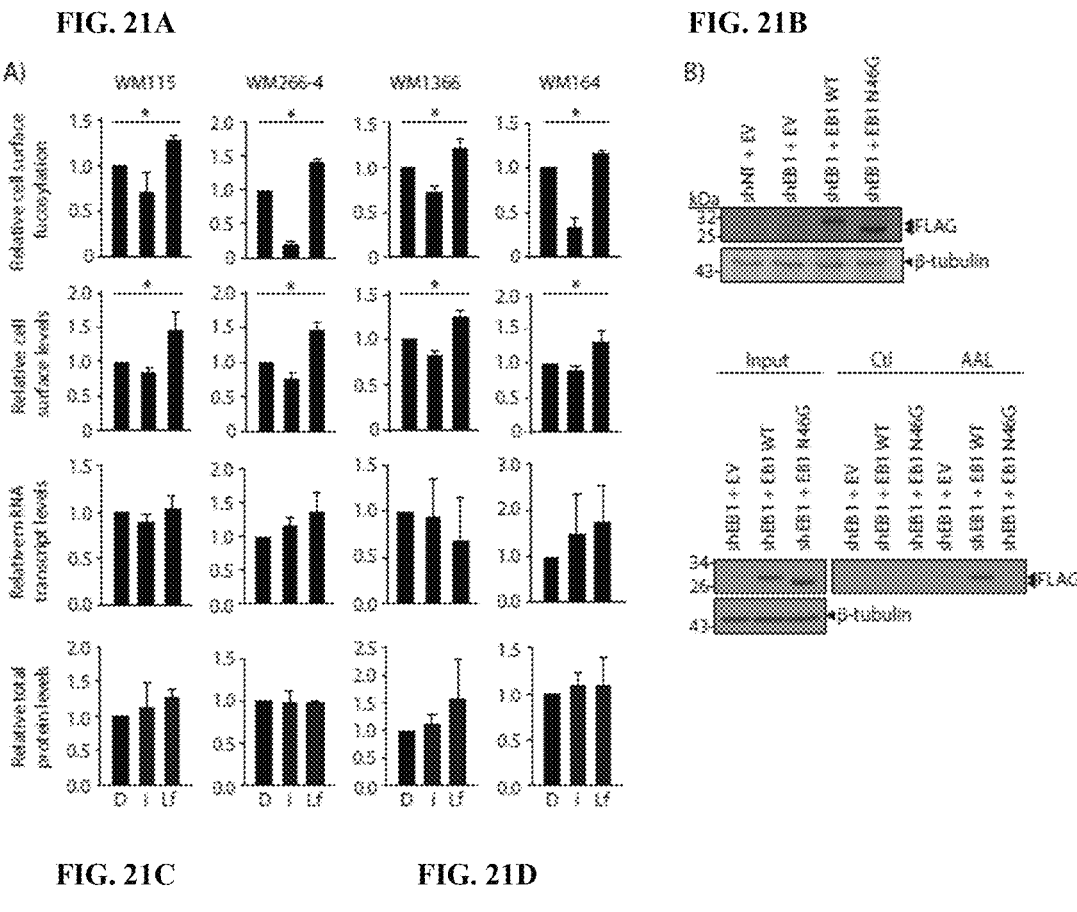
FIG. 21C
FIG. 21D
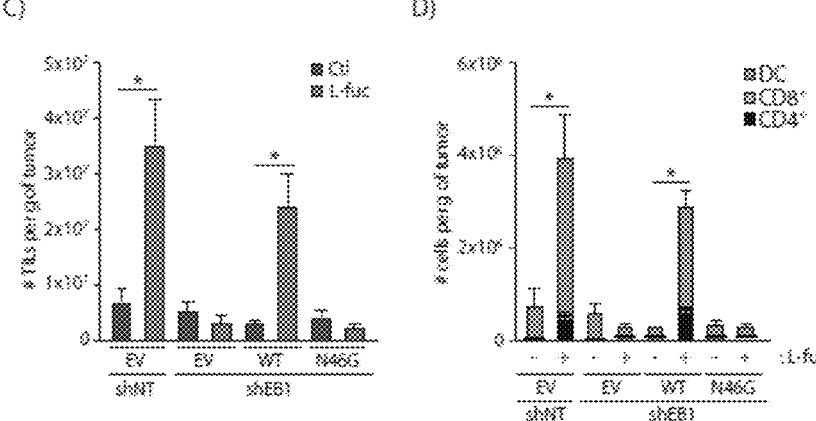

FUCOSYLATION AND IMMUNE MODULATION IN CANCER

CROSS REFERENCE TO RELATED APPLICATIONS

This application is a United States National Phase Patent Application of International Patent Application Number PCT/US2020/046694, filed on Aug. 17, 2020, which claims the benefit of priority to U.S. provisional Application No. 62/887,814, filed Aug. 16, 2019, each of which are incorporated by reference herein in their entireties.

I. BACKGROUND

Melanoma is one of the most lethal skin cancers worldwide, characterized by a striking ability to metastasize and develop therapeutic resistance. The immune system plays a crucial role in recognizing and suppressing cancers in the body. Unfortunately, melanomas can interact with and inactivate immune cells. Currently, among the most effective anti-melanoma therapies is immunotherapies. These include antibody-based immunotherapies, such Nivolumab or Ipilumumab, which block these inhibitory interactions, "reactivating" the tumor-suppressing activities of immune cells, as well as adoptive cell ("TIL") therapy which involves the ex vivo expansion of tumor-infiltrating lymphocytes. However, despite recent successes of such immunotherapies, responsiveness (and durations of responses) is limited to subsets of patients. Despite reports of striking efficacy, durable responses of immunotherapies have been limited to subsets of patients. In attempt to improve responses, clinical trials have tested combinations of immunotherapies with other therapeutic interventions, with limited success 1. Unfortunately, patients often experience significant adverse events, sometimes resulting in their withdrawal from the clinical trial. Another ongoing challenge with immunotherapies is ineffective patient stratification. Although biomarkers of responsiveness remain under active investigation, one commonality of poor response is the lack of TILs. Therefore, furthering our understanding of TIL biology and developing new approaches to increase TILs in melanoma are crucial for improving the efficacy of immunotherapies. What are needed are new immunotherapies that can overcome the limitations of existing therapeutic protocols.

II. SUMMARY

Disclosed are methods related to enhancing immune responses and treating cancers with the administration of fucose.

In one aspect, disclosed herein are methods of modulating major histocompatibility complex II human lymphocyte antigen (HLA)-DRB1 expression on the surface of a cell comprising contacting the cell with an agent that modulates the amount of fucosylation on the cell; wherein an increase in fucosylation increases surface expression of HLA-DRB1; and wherein a decrease in fucosylation decreases the surface expression of HLA-DRB1.

Also disclosed herein are methods of modulating major histocompatibility complex II HLA-DRB1 of any preceding aspect, wherein the agent that modulates fucosylation comprises an agent that increases fucosylation (such as a fucose including, but not limited to L-fucose, D-fucose, fucoidan, fucose-1-phosphate, GDP-L-fucose, or L-fucose/GDP-L-fucose analogues) or an agent that decreases fucosylation (such as, for example, 2-fluoro-fucose (FUTi)).

In one aspect, disclosed herein are methods of modulating the activation of CD4+ T cells in a subject comprising modulating fucosylation; wherein an increase in fucosylation increases surface expression of HLA-DRB1 thereby increasing CD4+ T cell activation; and wherein a decrease in fucosylation decreases the surface expression of HLA-DRB1 thereby decreasing CD4+ T cell activation.

Disclosed herein are methods of modulating the activation of CD4+ T cells comprising modulating fucosylation (for example, with an agent that modulates fucosylation (such as, for example, L-fucose, D-fucose, fucoidan, fucose-1-phosphate, GDP-L-fucose, or L-fucose/GDP-L-fucose analogues); wherein an increase in fucosylation increases CD4+ T cell activation; and wherein a decrease in fucosylation decreases CD4+ T cell activation.

Also disclosed herein are methods of modulating the activation of CD4+ T cells of any preceding aspect, wherein the agent that modulates fucosylation comprises an agent that increases fucosylation (such as a fucose including, but not limited to L-fucose, D-fucose, fucoidan, fucose-1-phosphate, GDP-L-fucose, or L-fucose/GDP-L-fucose analogues) or an agent that decreases fucosylation (such as, for example, 2-fluoro-fucose (FUTi)).

In one aspect, disclosed herein are methods of enhancing the efficacy of CD4+ T cell mediated therapy to treat a cancer (such as, for example a melanoma) in a subject, wherein said CD4+ T cell therapy is reliant on MHC class II HLA-DRB1 antigen presentation, and wherein said method comprises administering to the subject fucose (including, but not limited to L-fucose, D-fucose, fucoidan, fucose-1-phosphate, GDP-L-fucose, or L-fucose/GDP-L-fucose analogues).

Also disclosed herein are methods of enhancing the efficacy of CD4+ T cell mediated therapy of any preceding aspect, wherein the CD4+ T cell mediated therapy comprises an immune checkpoint blockade inhibitor (such as, for example, the PD-1 inhibitors lambrolizumab, OPDIVO® (Nivolumab), KEYTRUDA® (pembrolizumab), and/or pidilizumab; the PD-L1 inhibitors BMS-936559, TECENTRIQ® (Atezolizumab), IMFINZI® (Durvalumab), and/or BAVENCIO® (Avelumab); and/or the CTLA-4 inhibitor YERVOY® (ipilimumab)), adoptive cell therapies, and CAR T therapies.

In one aspect, disclosed herein are methods of increasing the number of tumor infiltrating lymphocytes (TILs) in a cancer microenvironment in a subject comprising administering to the subject an agent that an agent that modulates (including but not limited to increases) the amount of fucosylation on the cell (such as a fucose including, but not limited to L-fucose, D-fucose, fucoidan, fucose-1-phosphate, GDP-L-fucose, or L-fucose/GDP-L-fucose analogues).

Also disclosed herein are methods of increasing the efficacy of an immune checkpoint inhibitor blockade therapy (such as, for example, the PD-1 inhibitors lambrolizumab, OPDIVO® (Nivolumab), KEYTRUDA® (pembrolizumab), and/or pidilizumab; the PD-L1 inhibitors BMS-936559, TECENTRIQ® (Atezolizumab), IMFINZI® (Durvalumab), and/or BAVENCIO® (Avelumab); and/or the CTLA-4 inhibitor YERVOY® (ipilimumab)) to treat a cancer (such as for example melanoma) in a subject comprising administering to the subject an agent that modulates (including but not limited to increases) the amount of fucosylation on the cell (such as a fucose including, but not limited to L-fucose, D-fucose, fucoidan, fucose-1-phosphate, GDP-L-fucose, or L-fucose/GDP-L-fucose analogues). In one aspect, the fucose can be administered before and/or during administration of the anti-cancer agent.

In one aspect, disclosed herein are methods of treating, inhibiting, decreasing, reducing, ameliorating, and/or preventing a cancer or metastasis (such as, for example, a melanoma) in a subject comprising administering to the subject i) an immune checkpoint blockade inhibitor (such as, for example, the PD-1 inhibitors lambrolizumab, OPDIVO® (Nivolumab), KEYTRUDA®) (pembrolizumab), and/or pidilizumab; the PD-L1 inhibitors BMS-936559, TECENTRIQ® (Atezolizumab), IMFINZI® (Durvalumab), and/or BAVENCIO® (Avelumab); and/or the CTLA-4 inhibitor YERVOY® (ipilimumab)) and ii) an agent that an agent that modulates (including increases) the amount of fucosylation on the cell (such as a fucose including, but not limited to L-fucose, D-fucose, fucoidan, fucose-1-phosphate, GDP-L-fucose, or L-fucose/GDP-L-fucose analogues).

Also disclosed herein are methods of treating, inhibiting, decreasing, reducing, ameliorating, and/or preventing a cancer or metastasis (such as, for example, melanoma) in a subject comprising administering to the subject i) an immune checkpoint blockade inhibitor (such as, for example, the PD-1 inhibitors lambrolizumab, OPDIVO® (Nivolumab), KEYTRUDA® (pembrolizumab), and/or pidilizumab; the PD-L1 inhibitors BMS-936559, TECENTRIQ® (Atezolizumab), IMFINZI® (Durvalumab), and/or BAVENCIO® (Avelumab); and/or the CTLA-4 inhibitor YERVOY® (ipilimumab)) and ii) an agent that an agent that modulates the amount of fucosylation (such as a fucose including, but not limited to L-fucose, D-fucose, fucoidan, fucose-1-phosphate, GDP-L-fucose, or L-fucose/GDP-L-fucose analogues).

In one aspect, disclosed herein are methods of treating, inhibiting, decreasing, reducing, ameliorating, and/or preventing a cancer or metastasis in a subject of any preceding aspect, further comprising harvesting tumor infiltrating lymphocytes (TILs), chimeric antigen receptor (CAR) T cells, or marrow infiltrating lymphocytes (MILs), contacting TILs, CAR T cells, and/or MILs with the agent that modulates fucosylation, and administering to the subject the TILs, CAR T cells, and/or MILs that have been contacted with the agent.

Also disclosed herein are methods of increasing the efficacy of a tumor infiltrating lymphocyte (TIL) and/or marrow infiltrating lymphocyte (MIL) therapy to treat a cancer in a subject comprising administering to the subject an agent that modulates (including but not limited to increases) the amount of fucosylation on the cell (such as a fucose including, but not limited to L-fucose, D-fucose, fucoidan, fucose-1-phosphate, GDP-L-fucose, or L-fucose/GDP-L-fucose analogues).

In one aspect, disclosed herein are methods of increasing the efficacy of TIL therapy to treat a cancer of any preceding aspect, wherein the fucose is administered before resection of TILs. In one aspect, the method can further comprise administering the fucose is during ex vivo processing of the TILs or MILs.

In one aspect, disclosed herein are methods of increasing the efficacy of a chimeric antigen receptor (CAR) T cell therapy to treat a cancer in a subject comprising contacting the CAR T cells with an agent that modulates (including but not limited to increases) the amount of fucosylation on the cell (such as a fucose including, but not limited to L-fucose, D-fucose, fucoidan, fucose-1-phosphate, GDP-L-fucose, or L-fucose/GDP-L-fucose analogues) and administering the CAR T cell to the subject.

Also disclosed herein are methods of expanding or increasing the number of tumor infiltrating lymphocytes (TILs), chimeric antigen receptor (CAR) T cells, or marrow infiltrating lymphocytes (MILs) ex vivo comprising contacting the TILs, CAR T cells, and/or MILs with an agent that an agent that modulates the amount of fucosylation (such as, for example L-fucose, D-fucose, fucose-1-phosphate, or GDP-L-fucose).

In one aspect, disclosed herein are methods of activating tumor infiltrating lymphocytes (TILs), chimeric antigen receptor (CAR) T cells, or marrow infiltrating lymphocytes (MILs) ex vivo comprising contacting the TILs, CAR T cells, and/or MILs with an agent that an agent that modulates the amount of fucosylation (such as, for example L-fucose, D-fucose, fucose-1-phosphate, or GDP-L-fucose).

III. BRIEF DESCRIPTION OF THE DRAWINGS

The accompanying drawings, which are incorporated in and constitute a part of this specification, illustrate several embodiments and together with the description illustrate the disclosed compositions and methods.

FIGS. 1A, 1B, and 1C show that fucosylation decreases through melanoma progression. —Prior Art: Lau E, Feng Y, Claps G, et al. The transcription factor ATF2 promotes melanoma metastasis by suppressing protein fucosylation. Sci Signal. 2015; 8 (406): ra124. —FIG. 1A shows that immunostaining for fucosylated proteins of a melanoma tumor. FIG. 1B shows the measuring of UEA1 in HMB45/S100-positive melanoma cells. FIG. 1C shows the correlation of the level of UEA1 plotted against survival probability.

FIGS. 2A and 2B show that Dietary and Genetic modulation of the fucose pathway leads to tumor suppression as shown by supplementation of fucose (2A) and overexpression of mouse FUK (2B). —Prior Art: Lau E, Feng Y, Claps G, et al. The transcription factor ATF2 promotes melanoma metastasis by suppressing protein fucosylation. Sci Signal. 2015; 8 (406): ra124.—

FIGS. 2C and 2D show that Dietary fucose supplementation triggers increased leukocyte and NK cell infiltration of melanoma tumors. FIG. 2C shows immunofluorescent staining of a tissue sample with CD45 (general leukocyte marker, red) and DAPI to show immune cell infiltration. FIG. 2D shows the effect of fucosylation on NK cell as measured by DX5 (NK cell marker, red) and DAPI. —Prior Art: Lau E, Feng Y, Claps G, et al. The transcription factor ATF2 promotes melanoma metastasis by suppressing protein fucosylation. Sci Signal. 2015; 8 (406): ra124.—

FIGS. 3A and 3B show that dietary fucose increases immune infiltration of tumors, with a decrease in MDSCs and an increase in T cells. FIGS. 3A and 3B show the change in tumor volume following dietary fucose supplementation. FIGS. 3C and 3D show the change in (3C) total leukocytes and (3D) for T cells (CD3), CD4+ T cells (CD25), Dendritic cells (CD11c), NK cells (DX5), macrophage (F4/80), and myeloid derived suppressor cells (GR1) following dietary fucose supplementation.

FIGS. 4A, 4B, 4C, and 4D show that L-fucose triggers CD4+ T cell-dependent suppression of melanoma. FIG. 4A shows SW1 mouse melanoma tumor growth curves of mice fed with control (blue) or 100 mM L-fucose-supplemented (red) water over 45 days. FIG. 4B shows numbers of intratumoral CD4+T (left) or CD8+T (right) cells per g of tumor in control vs. L-fucose water-fed mice. FIG. 4C shows SW1 tumor growth curves in CD4+T (left) or CD8+T (right) cell-depleted mice fed with control (blue) or L-L-fucose (red) water over 45 days. FIG. 4D shows numbers of
intratumoral CD8+T (medium grey), NK (light grey) and
dendritic (DC; black) cells per g of tumor in control (PBS)
vs. CD4+ T-cell-depleted (−CD4) mice fed with control vs.
L-fucose (+F) water.

FIGS. 5A, 5B, 5C, and 5D show that Melanoma fucosy-
lation stimulated NK cell killing. FIG. 5 shows 1205LU
cells pre-treated with DMSO (control), 250 μM fucosyl-
transferase inhibitor (FUTi), or 250 μM L-fucose that were
co-cultured with immortalized (5A) or primary (5B) human
NK cells. After 8 h, LDH levels released in the media were
measured. *=p 0.02; •=p<0.001. FIGS. 5C and 5D show
Immunoblot analysis using AAL lectin (another fucose-
binding lectin) was performed to confirm the effects of FUTi
(C) or L-fucose (D) on 1205Lu cells (96 h treatment). (•:
p-value≥0.02) (*: p-value≥0.002).

FIGS. 6A, 6B, and 6C show that HLA-A and HLA-DRB1
are fucosylated in melanoma cell lines. The previous fuco-
sylated protein mass spectrometric analyses identified
HLA-A and HLA-DRB1 as fucosylated immunomodulatory
proteins in melanoma cells. FIG. 6A shows immunoblot
analysis for HLA-A, HLA-DRB1, and b-tubulin expression
was performed on a panel of melanocyte and melanoma cell
lines. FIG. 6B shows lectin-mediated proximity ligation
assay performed on WM793 cells for fucosylated HLA-A
(left) and HLA-DRB1 (right) (red), phalloidin (green), and
DAPI (blue). FIG. 6C shows that UEA1 and AAL lectin
pulldown was performed in WM793, 1205Lu, WM115, and
WM266-4 cell lines, followed by immunoblot analysis for
HLA-A and HLA-DRB1.

FIG. 7 shows Inhibiting fucosylation increases surface
presentation of HLA-A and β2-microglobulin, but not HLA-
DRB1. WM793 cells treated with DMSO (control, black) or
250 μM FUTi (grey) for 72 h stained with PKH26 (plasma
membrane stain) and HLA-A. β2-microglobulin (B2M), or
HLA-DRB1 antibodies. Stained cells were subjected to flow
cytometric analyses and quantitation of protein signal/
PKH26 signal to quantitate protein per relatice surface area.

FIGS. 8A, 8B, and 8C show that melanoma HLA-DRB1
is fucosylated and required for L-fucose-triggered mela-
noma suppression. FIG. 8A shows that human primary
melanocytes (HEMN) or indicated melanoma cell lines
immunoblotted (IB) for HLA-A, HLA-DRB1, and β-tubulin
FIG. 8B shows that I-fucose-binding lectin (AAL & UEA1)
pulldown of WM793 and 1205Lu or WM115 and WM266-4
patient-matched primary and metastatic cell line_pairs, IB
for HLA-A and HLA-DRB1. FIG. 8C shows growth curves
of control (SCR; left), H2K1 (shH2K1; center)- or IEB
(shIEB)-knocked down tumors in mice fed ±100 mM L-fuc
water. N=7 mice/condition. •: p<0.01. Differences in ±L-fuc
curves for shH2K1/shIEβ are not significant. (* initiate
L-fucose).

FIGS. 9A and 9B show HLA-DRB1 is fucosylated on
N48, and fucosylation promotes its cell surface presentation.
FIG. 9A shows AAL lectin pulldown of WM793 cells
transduced to express V5-tagged wild type HLA-DRB1,
N48G or T129A fucomutants of HLA-DRB1 followed by IB
for V5 or β-tubulin. FIG. 9B shows flow cytometry quan-
titating cell surface fucosylation (AAL lectin binding, left)
or HLA-DRB1 (right) of WM793 cells treated with DMSO,
FUTi, or L-fuc. AAL or HLA-DRB1 signals were normal-
ized to PKH26 (total membrane stain).

FIGS. 10A and 10B show Oral L-fucose is more tumor
suppressive than α-CTLA4 or α-PD1 alone, beginnings of
improved effects. SW1 tumor growth curves in mice fed
±100 mM L-fucose treated with either control (PBS) or
α-CTLA1 (10A) or α-PD1 (10B). Combinations are color-

6 coded as indicated. N=8 mice per condition. L-fucose was
administered in the water starting on day 14 (refreshed twice
weekly); α-CTLA4 or α-PD1 was administered (20 mg/kg
each) twice weekly starting day 14. Compared with PBS
control: #: p<0.001; *: p<0.05:

FIG. 11 shows that addition of L-fucose in combination
with anti-PD1 can enhance tumor suppression when com-
pared to either agent alone.

Figures 1A, 1B, 1C:
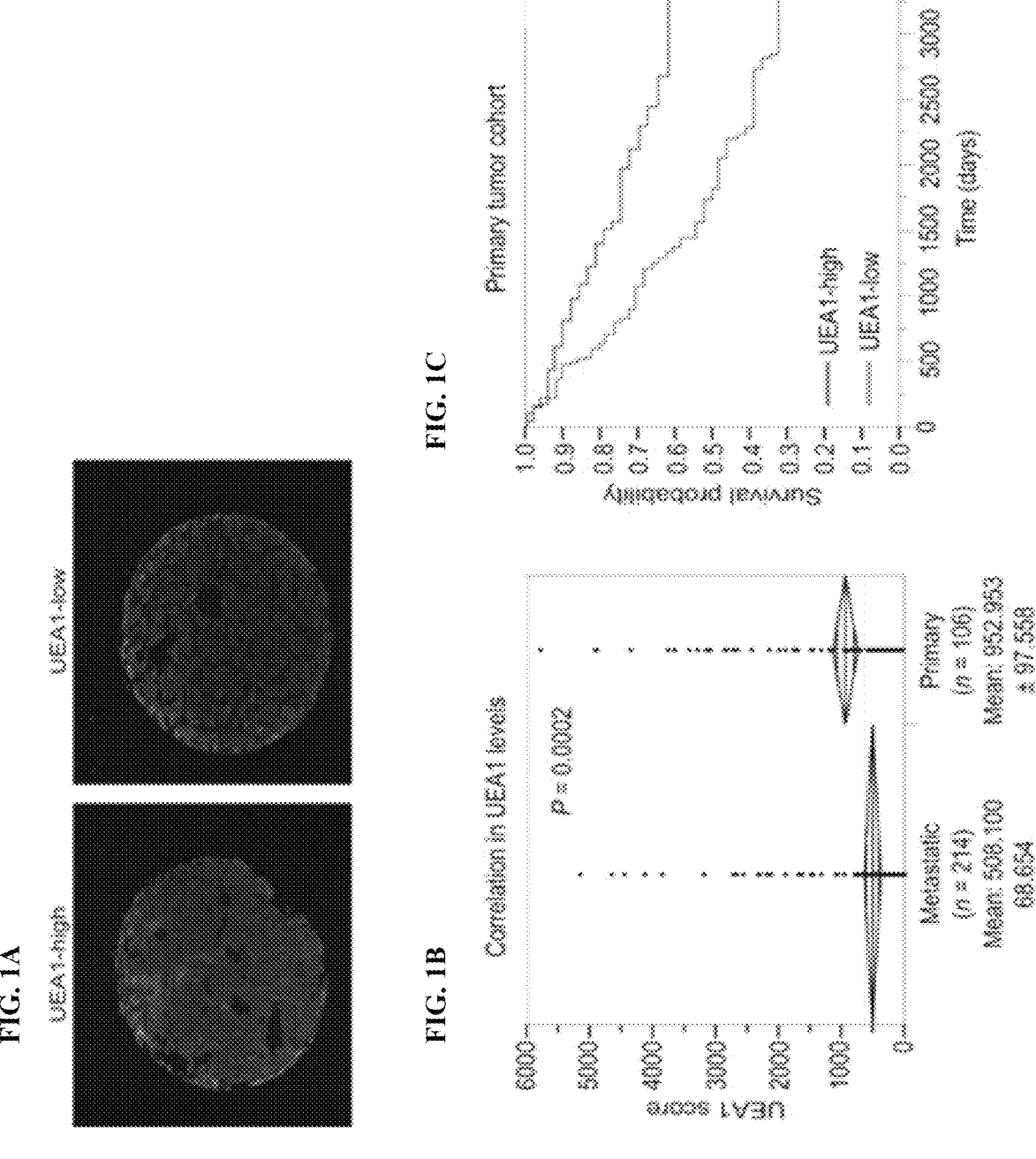

FIGS. 14A, 14B, 14C, 14D, 14E, 14F, 14G, 14H, and 14I
show that confirming increased tumor fucosylation and TIL
counts, lack of altered splenic immune cell profiles, and
correlations between tumor fucosylation and CD3+ T cells
in female vs. male melanoma patients. FIG. 14A shows
immunofluorescent (IF) staining analysis of SW1 intratu-
moral fucosylation (FFPE sections) and flow cytometric
profiling of immune populations (absolute cell numbers;
CD3+ T cells, natural killer cells (NKs), macrophages (MΦ),
MDSC-like cells (MDSCs), and dendritic cells (DCs)) in
(14B) spleens and (14C) SW1 tumors in control (Ctl)- or
L-fuc-supplemented C3H/HeN mice from FIG. 15A. FIG.
14D shows IF staining analysis of SM1 (14C) intratumoral
fucosylation (FFPE sections) and flow cytometric profiling
of indicated immune populations in (14E) spleens and (14F)
SMI melanoma tumors from Ctl- or L-fuc-supplemented
C57BL/6 mice from FIG. 15E. FIG. 14G shows IB analysis
confirming mFUK expression in SW1 cells (upper), IF
staining analysis of SW1 intratumoral fucosylation (FFPE
sections; lower), and (14H) flow cytometric profiling of
indicated immune populations in EV- or mFUK-expressing
SW1 tumors from Ctl- or L-fuc-supplemented C3H/HeN
mice. The tumor growth curves are means±SEM from ≥7
mice per group. *=p-value<0.05. FIG. 14I is TMA data
showing more significant correlation between tumor fuco-
sylation and intratumoral CD3+ T cell counts in male
patients. FIG. 14J shows scatterplots showing that the cor-
relation between melanoma-specific fucosylation and CD3+
T cell density (log 2 scale) is higher in the male melanoma
patients (Spearman's rho=0.43; p=0.036) than in female
patients (Spearman's rho=0.25; p=0.3367).

FIGS. 15A, 15B, 15C, 15D, 15E, 15F, 15G, 15H, 15I, 15J,
15K, 15L, 15M, and 15N show that increasing melanoma
fucosylation suppresses tumors and increases TIL abun-
dance, particularly intratumoral CD4+ and CD8+ T cells.
(15A) Volumetric growth curves, (15B) total TIL, counts,
(15C) % TIL subpopulations (CD3+ T cells, dendritic cells
(DCs), natural killer cells (NKs), macrophages (M), and
MDSC-like (MDSC) cells), and (15D)) intratumoral CD3+/
CD4+ (CD4+) and CD3+/CD8+ (CD8+) T cell counts of SW1
melanoma tumors in C3H/HeN mice. (15E) Volumetric
growth curves, (15F) total TIL counts, (15G) % TIL sub-
populations, and (15H) intratumoral CD4+ and CD8+ T cell
counts of SMI melanoma tumors in C57BI/6 mice. (15I)
Volumetric growth curves, (15J) total TIL, counts, (15K) %
TIL, subpopulations, and (15L) intratumoral CD4+ and
CD8+ T cell counts of empty vector (EV)- or mouse fucoki-
nase (mFUK)-expressing SW1 tumors in C3H/HeN mice.
(15M) Volumetric growth curves of SW1 tumors in NSG
mice. (15N) Association of melanoma-specific fucosylation
and CD3+ T cell density in a 41-patient melanoma tissue
microarray (log 2 scale). For each tumor mouse model:
when tumors reached ~150 mm³, control (Ctl)- or L-fucose-
supplemented water (L-fuc, 100 mM; ▼=initiated supplementation) was provided ad libitum. The tumor growth curves are means±SEM from ≥7 mice per group. *=p-value<0.05.

FIGS. 16A, 16B, 16C, 16D, 16E, and 16F show confirming CD4$^+$ and CD8$^+$ T cell immunodepletion in in vivo tumor models. Flow cytometric profiling of splenic CD4$^+$ T cells in control (PBS-injected) vs. CD4$^+$ T cell-depleted (16A) SW1 tumor-bearing C3H/HeN mice and (16D) SM1 tumor-bearing C57BL6 mice fed ±L-fuc from FIG. 17. Percentages represent % CD4$^+$ T of total splenic cells. Immunofluorescent histological profiling of splenic CD8$^+$ T cells in control vs. CD8$^+$ T cell-depleted (16B) SW1 tumor-bearing C3H/HeN mice and (16E) SMI tumor-bearing C57BL6 mice fed ±L-fuc from FIG. 17. Relative fold-changes in splenic CD8$^+$ T cells were determined by (total intrasplenic CD8$^+$ signal area/total intrasplenic DAPI area) as a measure of relative CD8$^+$ T cell abundance/spleen. Flow cytometric profiling of total TIL counts in control (PBS-injected) vs. CD4$^+$ T cell-depleted (16C) SW1 tumor-bearing C3H/HeN mice and (16F) SM1 tumor-bearing C57BL6 mice fed ±L-fuc from FIG. 17. *=p-value<0.05.

FIGS. 17A, 17B, 17C, 17D, 17E, 17F, 17G, and 17H show CD4$^+$ T cells are central for L-fucose-triggered tumor suppression and increases in NK, DC, and CD8$^+$ T cells. Volumetric growth curves for SW1 tumors in (17A) PBS (control)-injected, (17B) CD8$^+$ T cell-, or (17C) CD4$^+$ T cell-immunodepleted C3H/HeN mice. (17D) Comparison of intratumoral NK, DC, CD8$^+$ T, and CD4$^+$ T cell subpopulations (absolute cell numbers) from tumors in (17A) and (17C). Volumetric growth curves for SMI tumors in (17E) control (PBS)-injected, (17F) CD8$^+$ T cell-, or (17G) CD4$^+$ T cell-immunodepleted C57BL6 mice. (17H) Comparison of intratumoral NK, DC, CD8$^+$ T, and CD4$^+$ T subpopulations from tumors in (17E) and (17G). For each tumor mouse model: when tumors reached ~150 mm$^2$, control (Ctl)- or L-fucose-supplemented water (L-fuc, 100) mM; ▼=initiated supplementation) was provided ad libitum. The tumor growth curves are means±SEM from ≥7 mice per group. *=p-value<0.05.

FIGS. 18A and 18B show fucosylated mass spectrometric analysis and knockdown efficiency of H2K1 and H2EB1. FIG. 18A show (left) Schematic for proteomic analysis of fucosylated proteins in human melanoma cells using plenti-GFP empty vector (EV)-, pLenti-FUK-GFP-, or shFUK-expressing WM793 cells. (right) Top 20 pathways, plasma membrane- and immune-related proteins identified by Ingenuity Pathway Analysis (Qiagen) to be significantly altered by fucosylation. FIG. 18B shows qRT-PCR analysis confirming knockdown of H2K1 (shH2K1; left) or H2EB1 (shEB1; right) using 2 shRNAs per target compared to control non-targeting (shNT) shRNA. Red arrows indicate the specific shRNA clones used in functional experiments in the remainder of the study.

FIGS. 19A, 19B, 19C, 19D, 19E, 19F, 19G, and 19H show that HLA-DRB1 is expressed, fucosylated, and required for L-fucose-triggered melanoma suppression and increased TIL, abundance. FIG. 19A shows Immunoblot (IB) analysis of HLA-A and HLA-DRB1 protein levels in primary human melanocytes (HEMN) or the following human melanoma cell lines: A375, WM983A, WM983B, WM793, 1205Lu, WM1366, WM115, and WM266-4. FIG. 19B shows lectin pulldown (LPD) and IB analysis of the patient-matched primary and metastatic cell line pairs WM793 and 1205Lu (left) and WM115 and WM266-4 (right) for HLA-A and HLA-DRB1. FIG. 19C shows V5-immunoprecipitation (IP) and V5 and AAL IB analyses of WM793 cells expressing (left) V5-tagged HLA-A or (right)

V5-tagged HLA-DRB1. Volumetric growth curves for (19D) non-targeting control shRNA (shNT)-, (19E) H2K1-targeting shRNA (shH2K1)—, or (19F) H2EB1-targeting shRNA (shEB1)-expressing SW1 tumors in C3H/HeN mice. Flow cytometric comparison of (19G) absolute TIL, counts or (19H) intratumoral DC, CD8$^+$, and CD4$^+$ subpopulations from shNT- or shEB1-expressing SW1 tumors in (19D) and (19F). For (19D, 19E, and 19F): when tumors reached ~150 mm$^3$, control (Control) or L-fucose-supplemented water (L-fuc, 100 mM; ▼=initiated supplementation) was provided ad libitum. The tumor growth curves are means±SEM from ≥7 mice per group. *=p-value<0.05.

FIGS. 20A, 20B, 20C, 20D, 20E, and 20F show that fucosylation of HLA-DRB1 at N48 increases its cell surface presentation and is required for tumor suppression and increased TIL abundance. FIG. 20A shows (upper) Amino acid sequence alignments showing conservation of predicted N- and O-linked fucosylation sites in human HLA-DRB1 (N48 (SEQ ID NO: 21) and T129 (SEQ ID NO: 23)) and mouse H2EB1 (N46 (SEQ ID NO: 22) and T147 (SEQ ID NO: 24)). Structural model of the HLA-DRB1: HLA-DM complex (PDB ID, 4FQX); HLA-DRB1 (yellow) and DM (gray) (lower left). Structural model of CD4: HLA-DRB1: TCR complex (lower right). The model is reconstituted by superimposing the DRB1 beta chains from CD4: HLA-DR1 complex (PDB ID, 3S5L) and TCR: HLA-DR1 complex (PDB ID, 6CQR) using PyMOL. RMSD between the 163 backbone atoms is 0.497. The potential glycosylation sites, N48 and T129, of HLA-DR1 beta chain are shown as sticks. CD4 (cyan), HLA-DRB1 (yellow), antigen peptide (magenta), and TCR (green) (lower right). FIG. 20B shows HLA-DRB1 peptide fragment identified by nano-LC/MS to be fucosylated on N, with predicted HexNAc (4) Hex (3) Fuc (1) glycan structure shown above. FIG. 20C shows lectin pull down (LPD) and IB analyses of EV and V5-tagged wild-type HLA-DRB1 (WT)-, HLA-DRB1 N48G (N48G)-, and HLA-DRB1 T129A (T129A)-expressing WM793 cells. FIG. 20D shows DMSO- or fucosyltransferase inhibitor (FUTi)-treated WM793 cells immunofluorescently stained for endogenous HLA-DRB1, KDEL (ER marker), and DAPI. FIG. 20E shows flow cytometric analysis for relative cell surface fucosylation (upper) and cell surface HLA-DRB1 (upper middle), qRT-PCR analysis of relative HLA-DRB1 mRNA levels (lower middle), and IB analysis of HLA-DRB1 protein levels (lower) in WM793 and 1205Lu cells treated with DMSO (D), 250 µM FUTi (i), or 250 µM L-fuc (L-f). FIG. 20F shows volumetric growth curves for SW1 tumors expressing shNT (non-targeting shRNA)+EV (control) (upper left), shEB1+EV (upper right), shEB1+EB1 WT (lower left), or shEB1+EB1 N46G (lower right) in C3H/HeN mice. For (20F) when tumors reached ~150 mm$^3$, control (grey) or L-fucose supplemented water (red, 100 mM; ▼=initiated supplementation) was provided ad libitum. The tumor growth curves are means±SEM from ≥7 mice per group. *=p-value<0.05. Images shown in (D) are 20× magnification.

FIGS. 21A, 21B, 21C, and 21D show assessing the effects of modulating fucosylation on HLA-DRB1 localization, total protein, and mRNA levels; validation of knockdown/reconstitution and fucosylation of EB1 WT and N46G and its effects on TILs in vivo. FIG. 21A shows flow cytometric analysis for relative cell surface fucosylation (upper) and cell surface HLA-DRB1 levels (upper middle), qRT-PCR analysis of relative HLA-DRB1 mRNA levels (lower middle), and IB analysis of HLA-DRB1 protein levels (lower) in WM115, WM266-4, WM1366, and WM164 cell lines treated with DMSO (D), 250 µM FUTi (i), or 250 µM L-fuc (L-f). FIG. 21B (upper) shows IB analysis of SW1 cells expressing shNT (non-targeting shRNA)+EV (control), shEB1+EV-FLAG, shEB1+EB1 WT-FLAG, or shEB1+EB1 N46G-FLAG. (lower) shows LPD and IB analysis of SW1 cells expressing shEB1+EV-FLAG, shEB1+EB1 WT-FLAG, or shEB1+EB1 N46G-FLAG. FIG. 21C shows total TIL counts and (21D)) indicated immune subpopulations in the tumors of the control or EB1 knockdown/EB1 WT- or EB1 N46G-reconstituted SW1 tumors of the Ctl- or L-fuc-supplemented C3H/HeN mice in FIG. 20F. *=p-value<0.05.

Figures 22A, 22B, 22C:
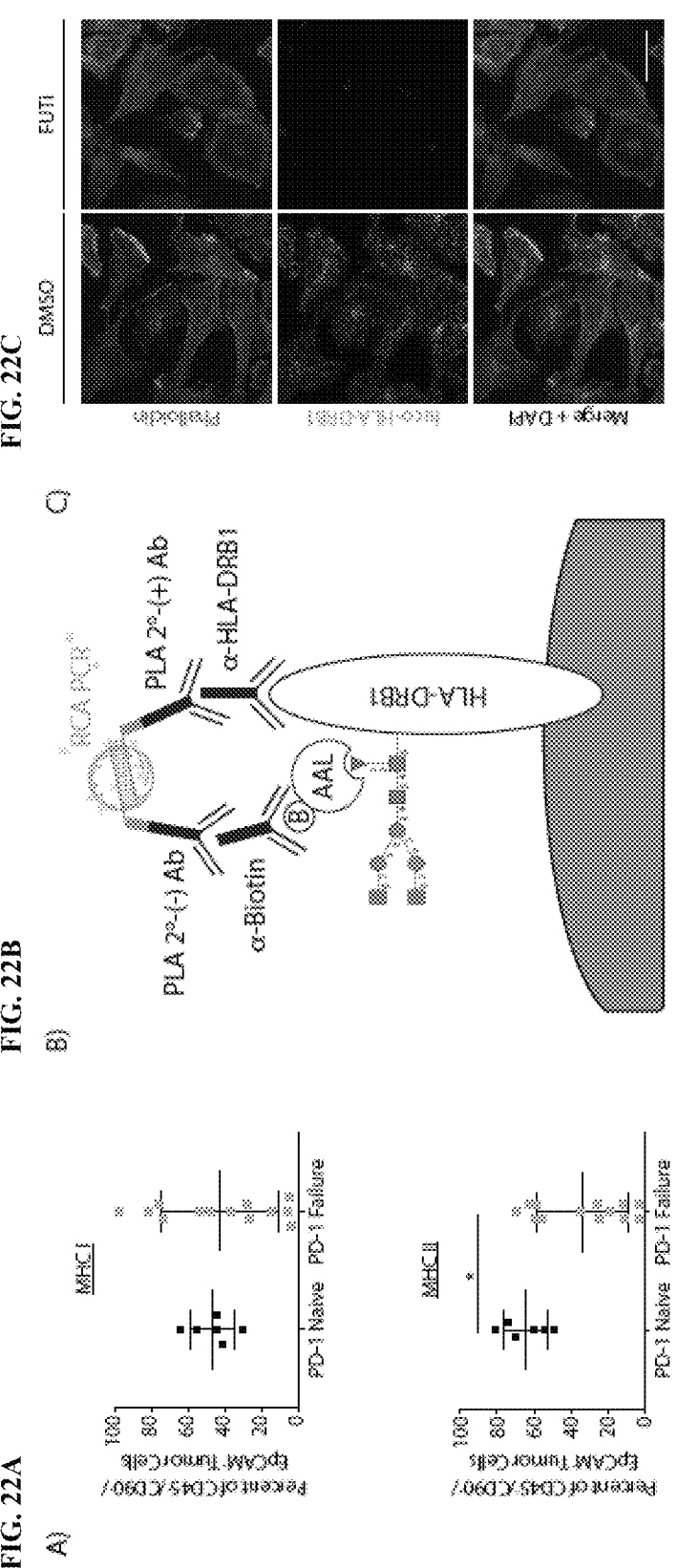
Figures 22D, 22E, 22F:
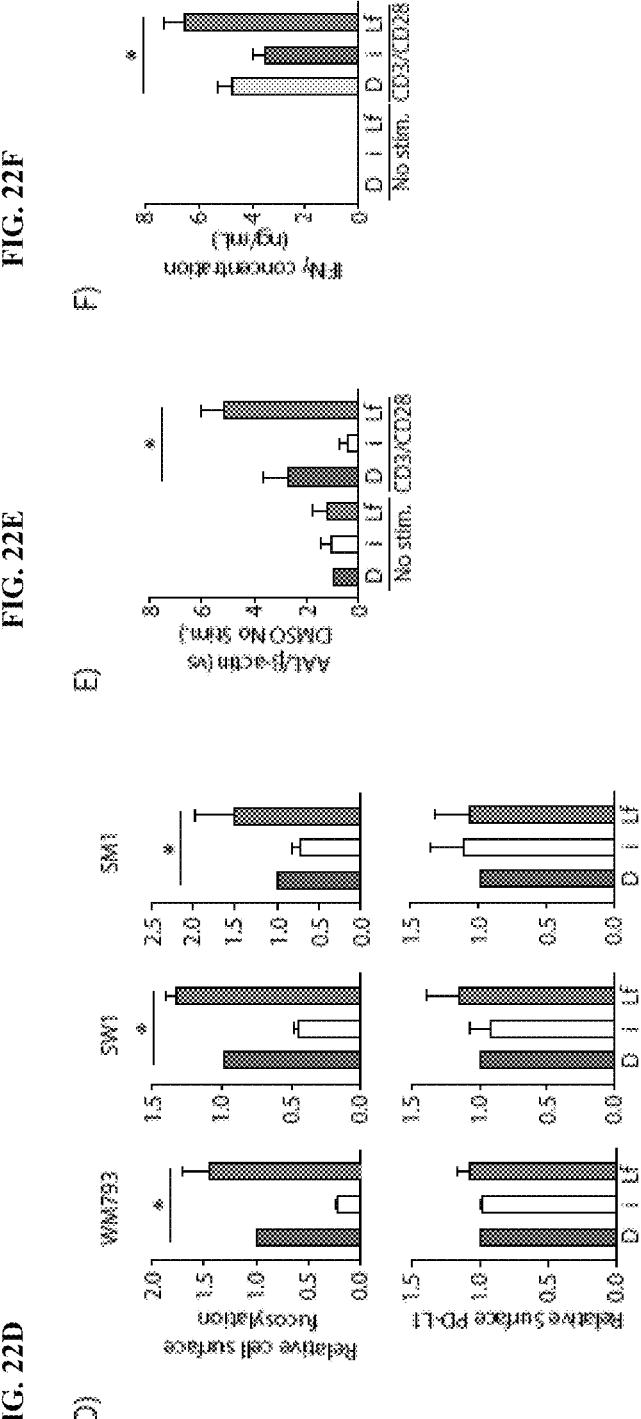

FIGS. 22A, 22B, 22C, 22D, 22E, and 22F show reduced cell surface class II MHC during anti-PD-1 failure; L-PLA schematic and the effects of L-fucose on tumoral PD-L1 expression and peripheral human CD4$^+$ T cell fucosylation and IFN$\gamma$ production/secretion. FIG. 22A shows the % of total CD45$^-$/CD90$^-$/EpCAM tumor cells exhibiting positive (upper) pan MHC-I or (lower) pan MHC-II staining from either anti-PD1 naïve patients (n=6) or patients who failed anti-PD1 (n=13). FIG. 22B shows a schematic of lectin-mediated proximity ligation analysis (L-PLA) using fucosylated HLA-DRB1 as an example. We stained for (i) HLA-DRB1 using anti-HLA-DRB1 followed by (+) oligo-conjugated PLA secondary and (ii) fucosylated glycan using biotinylated ("B") AAL lectin followed by anti-biotin followed by (−) oligo-conjugated PLA secondary. Ligated PLA oligos were subjected to rolling circle amplification PCR (RCA PCR), giving rise to fluorescent punctae. FIG. 22C shows lectin-mediated proximity ligation analysis (L-PLA) of endogenous, fucosylated HLA-DRB1 was performed on WM793 cells treated with DMSO or FUTi (with phalloidin and DAPI co-stains; scale bar: 50 μm). FIG. 22D shows WM793 (left), SW1 (middle), and SM1 (right) cells were treated with DMSO (D) or 250 μM FUTi (i) or L-fuc (L-f) and subjected to flow cytometric assessment of changes in cell surface fucosylation (upper) and PD-L1 levels (lower). Healthy human donor peripheral CD4$^+$ T cells were treated with DMSO (D) and 250 μM FUTi (i) or L-fuc (L-f) and subjected to (22E) IB analysis for changes in fucosylation (AAL IB) or (22F) ELISA assay to measure changes in IFN$\gamma$ production/secretion. *=p-value<0.05.

FIGS. 23A, 23B, 23C, 23D, and 23E show L-fucose is as efficacious or improves the efficacy of anti-PD1 checkpoint blockade therapy. Volumetric growth curves for SW1 tumors in C3H/HeN mice (23A) and SMI tumors in C57BL/6 mice (23B) fed ±L-fuc and treated with PBS (control) or anti-PD-1. For both mouse models, PBS or anti-PD-1 was administered by intraperitoneal injection starting at day 7 (concurrent with initiation of L-fuc supplementation) and was re-administered every 3-4 days until endpoint. The tumor growth curves are means±SEM from ≥7 mice per group. Lectin-mediated proximity ligation analysis (L-PLA) of endogenous, fucosylated HLA-DRB1 was performed on (23C) coverslip-grown WM793 cells (with phalloidin and DAPI co-stains; scale bar: 50 μm), or (23D), human melanoma FFPE tissue specimens (with MART1+S100 and DAPI as co-stains; scale bar: 25 μm). Shown are representative images of secondary antibody-only control (upper) or full L-PLA (lower) stainings. (23E) Shown are box plots of (i) total fucosylation (AAL), (ii) total DRB1, (iii) fucosylated HLA-DRB1 staining intensities per cell, and (iv) total number of CD4$^+$ T cells within MART1+S100-positive regions in FFPE tumor sections of 2 responder (Pt. 1 & 2) and 2 non-responder (Pt. 3 & 4) patients.

Figure 24:
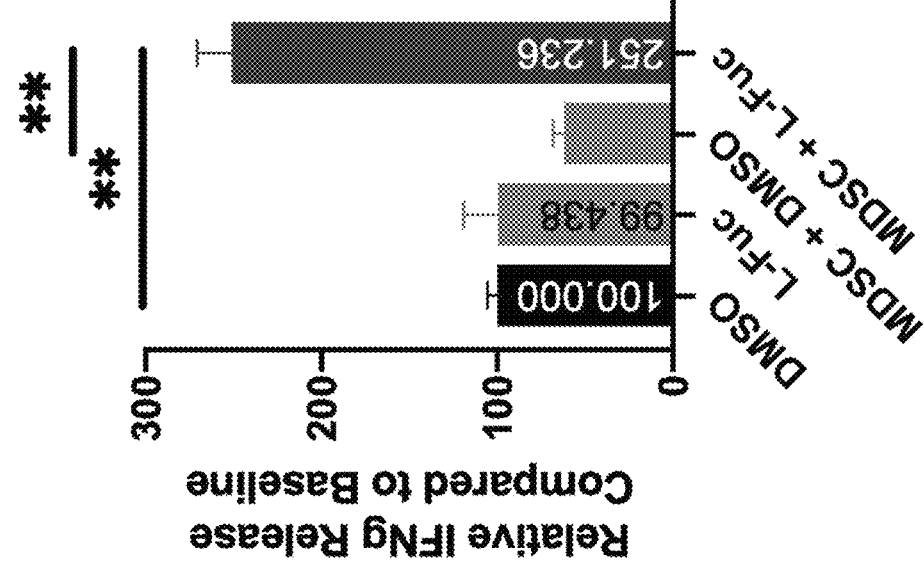

FIG. 24 shows that L-fucose pre-treatment alleviates MDSC suppression of T cell activity. Shown are IFN$\gamma$ production/secretion levels of combined bulk CD4$^+$ and CD8$^+$ T cells from BalbC mice treated with either DMSO (black column) or L-fucose (red column) or co-cultured with MDSCs pre-treated with DMSO (aquamarine column) or with L-fucose (purple column). The T cells were activated using CD3/CD28 beads. These data show that whereas DMSO or L-fuc significantly impact overall IFN$\gamma$ production/secretion by combined/pooled CD4$^+$ and CD8$^+$ T, L-fuc completely reverts MDSC-mediated T cell suppression. In fact, the significant enhancement in IFNg production/secretion triggered by co-culture of the T cells with MDSCs that were pre-treated with L-fucose suggest that L-fucose might be shifting MDSC phenotype from immunosuppressive to known antigen-presenting (and T cell-stimulating) phenotype.

Figure 25:
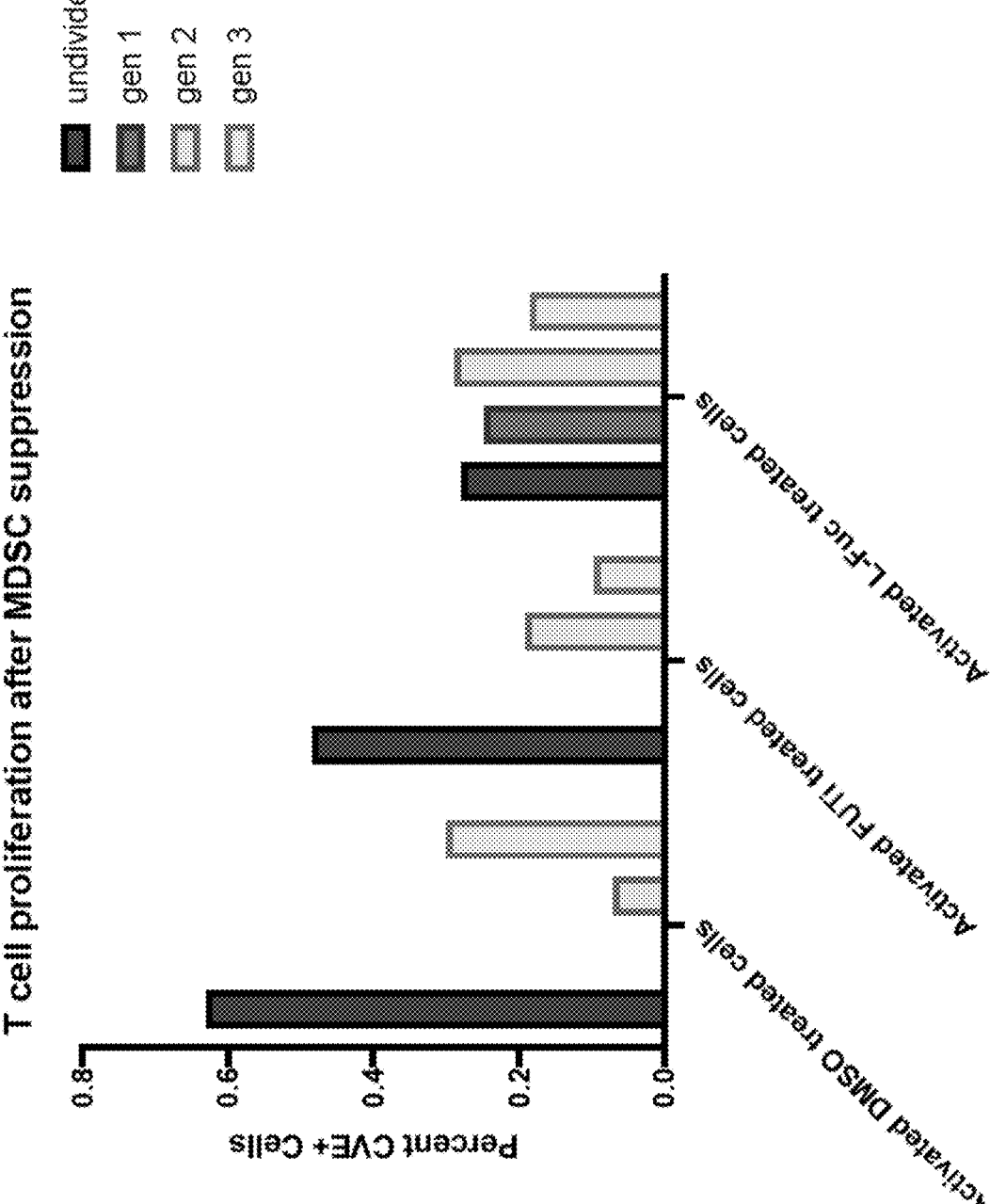

FIG. 25 shows that L-fucose pre-treatment alleviates MDSC suppression of T cell proliferation. Shown progressive divisions of CD3/CD28-activated T cells (both CD4+ and CD8+ combined) as affected by co-culture with DMSO (control)-, FUTi (fucosyltransferase inhibitor)-, or L-fucose-pre-treated MDSCs. Undivided T cells are represented by the dark grey column. Divisions were measured by loss of CellTrace™ Violet stain. First division is represented by the light green column; second division is represented by the yellow column; and third division is represented by the navy blue column. The data show that whereas DMSO- or FUTi-pre-treated MDSCs generally suppress T cell proliferation upon CD3/CD28 activation, L-fucose-pre-treated MDSCs do not, as reflected by the increase in progressive T cell divisions.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A number of embodiments of the invention have been described. Nevertheless, it will be understood that various modifications may be made without departing from the spirit and scope of the invention. Accordingly, other embodiments are within the scope of the following claims.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself.

For example, if the value "10)" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims that follow, reference will be made to a number of terms which shall be defined to have the following meanings:

"Optional" or "optionally" means that the subsequently described event or circumstance may or may not occur, and that the description includes instances where said event or circumstance occurs and instances where it does not.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

"Biocompatible" generally refers to a material and any metabolites or degradation products thereof that are generally non-toxic to the recipient and do not cause significant adverse effects to the subject.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions provided and/or claimed in this disclosure. Embodiments defined by each of these transition terms are within the scope of this disclosure.

A "control" is an alternative subject or sample used in an experiment for comparison purposes. A control can be "positive" or "negative."

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

A "pharmaceutically acceptable" component can refer to a component that is not biologically or otherwise undesirable, i.e., the component may be incorporated into a pharmaceutical formulation provided by the disclosure and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Polymer" refers to a relatively high molecular weight organic compound, natural or synthetic, whose structure can be represented by a repeated small unit, the monomer. Non-limiting examples of polymers include polyethylene, rubber, cellulose. Synthetic polymers are typically formed by addition or condensation polymerization of monomers. The term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers. The term "polymer" encompasses all forms of polymers including, but not limited to, natural polymers, synthetic polymers, homopolymers, heteropolymers or copolymers, addition polymers, etc.

A "binding molecule" or "antigen binding molecule" (e.g., an antibody or antigen-binding fragment thereof) as provided herein refers in its broadest sense to a molecule that specifically binds an antigenic determinant. In one embodiment, the binding molecule specifically binds to an immunoregulator molecule (such as for example, a transmembrane SEMA4D (CD100) polypeptide of about 150 kDa or a soluble SEMA4D polypeptide of about 120 kDa). In another embodiment, a binding molecule is an antibody or an antigen binding fragment thereof, e.g., MAb 67 or pepinemab.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a non-immunogenic cancer). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Methods and Compositions

Fucosylation, the post-translational modification of proteins with the dietary sugar L-fucose, is a mechanism that is well established for its importance in immune cell biology and organ developmental processes but that is poorly understood in terms of its roles in cancer. Fucose is transported extracellularly through the plasma membrane, where it is first phosphorylated by fucokinase (FUK). Then it is conjugated with GDP, yielding GDP-Fucose, which is a usable form in the cell. GDP-Fucose is transported into the ER/Golgi through SLC35C1/2, where it can be conjugated to a serine/threonine via an oxygen, which is referred to as O'-linked fucosylation, or to an arginine via a nitrogen, which is referred to as N'-linked fucosylation. The fucosylated protein can then be either trafficked to the cytoplasm or the cell surface. Global fucosylation is reduced during progression in human melanomas (UEA1 fucose-binding lectin staining analysis of tumor microarray (TMA; n=~300 patients)) via an ATF2-mediated transcriptional repression of fucokinase (FUK). Importantly, increasing fucosylation by genetic manipulation of tumor cells or by dietary L-fucose supplementation significantly blocks tumor growth and metastasis by >50% in mouse models. The studies herein demonstrate that i) tumor fucosylation levels can be used to identify different stages of cancer, and ii), the manipulation of fucosylation represents a feasible anti-cancer approach.

In one aspect, disclosed are methods modulating major histocompatibility complex II human lymphocyte antigen (HLA)-DRB1 expression on the surface of a cell comprising contacting the cell with an agent that modulates the amount of fucosylation on the cell; wherein an increase in fucosylation increases surface expression of HLA-DRB1; and wherein a decrease in fucosylation decreases the surface expression of HLA-DRB1. The modulation of HLA-DDRB1 can be accomplished by increasing (including, but not limited to L-fucose, D-fucose, fucoidan, fucose-1-phosphate, GDP-L-fucose, or I-fucose/GDP-L-fucose analogues) or decreasing fucosylation through the use of agents such as fucose or fucose comprising compositions that increase fucosylation of the use of agents that suppress fucosylation such as 2-fluoro-fucose (FUTi). The disclosure herein shows that through the administration of fucose increases the surface expression of MHC class II HLA-DRB1 and as a result increased CD4+ T cell activation. Conversely administration of a suppressor of fucosylation decreased surface expression of MHC class II HLA-DRB1 and as a result decreased CD4+ T cell activation. Accordingly, disclosed herein are methods of modulating the activation of CD4+ T cells in a subject comprising modulating fucosylation; wherein an increase in fucosylation increases surface expression of HLA-DRB1 thereby increasing CD4+ T cell activation; and wherein a decrease in fucosylation decreases the surface expression of HLA-DRB1 thereby decreasing CD4+ T cell activation. Disclosed herein are methods of modulating the activation of CD4+ T cells comprising modulating fucosylation (for example, with an agent that modulates fucosylation (such as, for example, L-fucose, D-fucose, fucoidan, fucose-1-phosphate, GDP-L-fucose, or L-fucose/GDP-L-fucose analogues); wherein an increase in fucosylation increases CD4+ T cell activation; and wherein a decrease in fucosylation decreases CD4+ T cell activation.

Accordingly, in one aspect, disclosed herein are methods of increasing the number of tumor infiltrating lymphocytes (such as, for example NK cells, dendritic cells, and T cells) at least 10, 11, 12, 13, 14, 15, 16, 17, 18, 19, 20, 21, 22, 23, 24, 25, 30, 35, 40, 45, or 50-fold (for example between about 10-fold and about 50-fold) in a subject with a tumor comprising administering fucose to the subject. It is understood that the methods of increasing the number of tumor infiltrating lymphocytes, wherein the fucose is administered orally. It is understood and herein contemplated that the increase in immune effector cells can coincide with a subsequent decrease in immune suppressor cells. Thus, in one aspect, disclosed herein are methods of any preceding aspect, wherein the method further results in at least a 20% reduction in myeloid-derived suppressor cells.

The fucose modulating compositions (including, but not limited to fucose (such as, for example L-fucose, D-fucose, fucoidan, fucose-1-phosphate, GDP-L-fucose, or L-fucose/

GDP-L-fucose analogues), fucose comprising compositions, and agents the suppress fucosylation (such as, for example, 2-fluoro-fucose (FUTi)) can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The fucose modulating compositions (including, but not limited to fucose (such as, for example L-fucose, D-fucose, fucoidan, fucose-1-phosphate, GDP-L-fucose, or L-fucose/GDP-L-fucose analogues), fucose comprising compositions, and agents the suppress fucosylation (such as, for example, 2-fluoro-fucose (FUTi)) may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the fucose comprising compositions into the nose and nasal passages through one or both of the nares and can comprise delivery by a spraying mechanism or droplet mechanism, or through aerosolization of the nucleic acid or vector. Administration of the fucose modulating compositions (including, but not limited to fucose (such as, for example L-fucose, D-fucose, fucoidan, fucose-1-phosphate, GDP-L-fucose, or L-fucose/GDP-L-fucose analogues), fucose comprising compositions, and agents the suppress fucosylation (such as, for example, 2-fluoro-fucose (FUTi)) by inhalant can be through the nose or mouth via delivery by a spraying or droplet mechanism. Delivery can also be directly to any area of the respiratory system (e.g., lungs) via intubation. The exact amount of the fucose comprising compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the fucose modulating compositions (including, but not limited to fucose (such as, for example L-fucose, D-fucose, fucoidan, fucose-1-phosphate, GDP-L-fucose, or L-fucose/GDP-L-fucose analogues), fucose comprising compositions, and agents the suppress fucosylation (such as, for example, 2-fluoro-fucose (FUTi)), if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bio-*

*conjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and Mckenzie, *Immunolog. Reviews,* 129:57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

The fucose modulating compositions (including, but not limited to fucose (such as, for example L-fucose, D-fucose, fucoidan, fucose-1-phosphate, GDP-L-fucose, or L-fucose/GDP-L-fucose analogues), fucose comprising compositions, and agents the suppress fucosylation (such as, for example, 2-fluoro-fucose (FUTi)) can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The fucose comprising compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Fucose modulating compositions (including, but not limited to fucose (such as, for example L-fucose, D-fucose, fucoidan, fucose-1-phosphate, GDP-L-fucose, or L-fucose/GDP-L-fucose analogues), fucose comprising compositions, and agents the suppress fucosylation (such as, for example, 2-fluoro-fucose (FUTi)) for oral administration include powders or granules, suspensions or solutions in water or non-aqueous media, capsules, sachets, or tablets. Thickeners, flavorings, diluents, emulsifiers, dispersing aids or binders may be desirable.

Some of the fucose modulating compositions (including, but not limited to fucose (such as, for example L-fucose, D-fucose, fucose-1-phosphate, or GDP-L-fucose), fucose comprising compositions and agents the suppress fucosylation (such as, for example, 2-fluoro-fucose (FUTi)) compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Effective dosages and schedules for administering the fucose comprising compositions may be determined empirically, and making such determinations is within the skill in the art. The dosage ranges for the administration of the fucose comprising compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

As disclosed herein, the administration of fucose can expand and/or activate TILs, marrow infiltrating lymphocytes (MILs), and chimeric antigen receptor (CAR) T cell production ex vivo and expanding TILs and MILs in vivo. Thus, disclosed herein are methods of increasing and/or expanding the number of and/or activating tumor infiltrating lymphocytes (TILs) or marrow infiltrating lymphocytes (MILs) in a cancer microenvironment in a subject comprising administering to the subject an agent that modulates (including but not limited to increases) the amount of fucosylation on the cell (such as a fucose including, but not limited to L-fucose, D-fucose, fucoidan, fucose-1-phosphate, GDP-L-fucose, or L-fucose/GDP-L-fucose analogues). As noted above the expansion can also occur to cells contacted with the agent that modulated fucosylation ex vivo. Thus, in one aspect, disclosed herein are methods of increasing, expanding, and/or activating an ex-vivo population of tumor infiltrating lymphocytes (TILs), marrow infiltrating lymphocytes (MILs), and or chimeric antigen receptor T cells comprising contacting the TILs, MILs, and/or CAR T cells with an agent that modulates (including but not limited to increases) the amount of fucosylation (such as a fucose including, but not limited to L-fucose, D-fucose, fucoidan, fucose-1-phosphate, GDP-L-fucose, or L-fucose/GDP-L-fucose analogues).

In the production of TILs and MILs, once a surgically resectable tumor has been obtained, the tumor is typically cut into small fragments and multiple fragments placed into wells of a culture plate where initial TIL, or MIL, expansion (referred to as "Pre-REP") occurs. The initially expanded TIL, and/or MIL, population is then subject for a second round of expansion (referred to as "REP") in tissue culture flasks. It is understood and herein contemplated that increasing (i.e., expanding) the Pre-REP population of TILs and/or MILs can increase the efficacy of TIL and MIL, immunotherapy the effectiveness of which can be dependent on the size of the TIL or MIL, population prior to resection. Accordingly, disclosed herein are methods of increasing the efficacy of a tumor infiltrating lymphocyte (TIL) and/or marrow infiltrating lymphocyte (MIL) therapy to treat a cancer in a subject comprising administering to the subject an agent that modulates (including but not limited to increases) the amount of fucosylation on the cell (such as a fucose including, but not limited to L-fucose, D-fucose, fucoidan, fucose-1-phosphate, GDP-L-fucose, or L-fucose/GDP-L-fucose analogues).

As disclosed herein, administration of the fucose or fucose comprising composition can occur at any time before, during, or after production of TILs, MILs, and/or CAR T cells including, but not limited to before, during, or after pre-REP or before, during, or after REP. In other words, administration of fucose can occur before pre-REP can occur at least 96, 84, 72, 60, 48, 36, 24, 18, 12, 8, 6, 5, 4, 3, 2, 1 hrs, 45, 30, 15, 10, or 5 minutes before the pre-REP expansion, concurrent with the commencement of pre-REP expansion, or at least 1, 2, 3, 4, 5, 10, 15, 30, 45 minutes, 1, 2, 3, 4, 5, 6, 7, 8, 9, 10, 11, 12, 18, 24, 36, 48, 60, 72, 84, or 96 hours after the commencement of the pre-REP expansion. Similarly, administration of fucose can occur before REP expansion can occur at least 96, 84, 72, 60, 48, 36, 24, 18, 12, 8, 6, 5, 4, 3, 2, 1 hrs, 45, 30, 15, 10, or 5 minutes before the REP expansion, concurrent with the commencement of pre-REP expansion, or at least 1, 2, 3, 4, 5, 10, 15, 30, 45 minutes, 1, 2, 3, 4, 5, 6, 7, 8, 9, 10, 11, 12, 18, 24, 36, 48, 60, 72, 84, or 96 hours after the commencement of the REP expansion. In one aspect, fucose can be administered to the subject in vivo following REP expansion of TILS and before, concurrently with, or after administration of TILs grown ex vivo are transferred to a subject in need thereof. Thus, in one aspect, the expansion of TILS via fucosylation can occur in vivo. In one aspect, fucose can be administered at least 96, 84, 72, 60, 48, 36, 24, 18, 12, 8, 6, 5, 4, 3, 2, 1 hrs, 45, 30, 15, 10, or 5 minutes before the transfer of ex vivo expanded TILs, concurrent with the administration of TILs, or at least 1, 2, 3, 4, 5, 10, 15, 30, 45 minutes, 1, 2, 3, 4, 5, 6, 7, 8, 9, 10, 11, 12, 18, 24, 36, 48, 60, 72, 84, or 96 hours after the administration of TILs to the subject.

In one aspect, disclosed herein are methods of treating, reducing, decreasing, inhibiting, ameliorating, and/or preventing a cancer or metastasis (such as, for example, melanoma) in a subject comprising administering to the subject fucose (such as for example, L-fucose, D-fucose, fucoidan, fucose-1-phosphate, GDP-L-fucose, or L-fucose/GDP-L-fucose analogues) and CD4+ T cell mediated therapy such as, for example, an anti-cancer agent (such as, for example, PD1/PDL1 blockade inhibitors and/or CTLA4/B7-1 or 2 inhibitors (such as, for example, PD-1 inhibitors lambrolizumab, OPDIVO® (Nivolumab), KEYTRUDA® (pembrolizumab), and pidilizumab; PD-L1 inhibitors BMS-936559, TECENTRIQ® (Atezolizumab), IMFINZI® (Durvalumab), and BAVENCIO® (Avelumab); and CTLA-4 inhibitors YERVOY® (ipilimumab) or any other anti-cancer agent disclosed herein), adoptive cell therapies, and/or CAR T therapies. The disclosed methods of treating and enhancing immune responses comprising the administration of fucose, have the functional effect of being an adjuvant as the addition of fucose stimulates increased fucosylation and increased MHC class II HLA-DRB1 expression which in turn increases CD4+ T cell activation. Accordingly, disclosed herein are enhancing the efficacy of CD4+ T cell mediated therapy (such as, for example, PD-1 inhibitors lambrolizumab, OPDIVO® (Nivolumab), KEYTRUDA® (pembrolizumab), and pidilizumab; PD-L1 inhibitors BMS-936559, TECENTRIQ® (Atezolizumab), IMFINZI® (Durvalumab), and BAVENCIO® (Avelumab); and CTLA-4 inhibitors YERVOY® (ipilimumab) or any other anti-cancer agent disclosed herein) adoptive cell therapies, and/or CAR T therapies comprising the administration of any known fucose including I-fucose, D-fucose, or any other known fucose isomer including phosphorylated fucose including, but not limited to fucose-1-phosphate (a.k.a., phosphorylated L-fucose), and/or GDP-L-fucose.

The disclosed methods of treating cancer; expanding and/or activating T cells, and or enhancing the efficacy of a CD4+ T cell mediated therapy can be used to treat any disease where uncontrolled cellular proliferation occurs such as cancers. Thus, in one aspect disclosed herein are methods of treating, inhibiting, decreasing, reducing, ameliorating, and/or preventing a cancer or metastasis (such as, for example, a melanoma) in a subject comprising administering to the subject an agent that an agent that modulates (including increases) the amount of fucosylation on the cell (such as a fucose including, but not limited to L-fucose, D-fucose, fucoidan, fucose-1-phosphate, GDP-L-fucose, or L-fucose/GDP-L-fucose analogues). A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer. The methods disclosed herein may also be used for the treatment of precancer conditions such as cervical and anal dysplasias, other dysplasias, severe dysplasias, hyperplasias, atypical hyperplasias, and neoplasias.

The disclosed methods of treatment and/or enhancing the efficacy of CD4+ T cell mediated therapy (including, but not limited immune checkpoint blockade inhibition therapy) contemplate the co-administration of a CD4+ T cell mediated therapy such as an anti-cancer agent. The anti-cancer agent can comprise any anti-cancer agent known in the art including, but not limited to antibodies, tumor infiltrating lymphocytes, checkpoint inhibitors, dendritic cell vaccines, anti-cancer vaccines, immunotherapy, and chemotherapeutic agents. In one aspect, the anti-cancer agent can include, but is not limited to Abemaciclib, Abiraterone Acetate, Abitrexate (Methotrexate), ABRAXANE® (Paclitaxel Albumin-stabilized Nanoparticle Formulation), ABVD, ABVE, ABVE-PC, AC, AC-T, ADCETRIS® (Brentuximab Vedotin), ADE, Ado-Trastuzumab Emtansine, Adriamycin (Doxorubicin Hydrochloride), Afatinib Dimaleate, AFINITOR® (Everolimus), AKYNZEO® (Netupitant and Palonosetron Hydrochloride), ALDARA® (Imiquimod), Aldesleukin, ALECENSA® (Alectinib), Alectinib, Alemtuzumab, Alimta (Pemetrexed Disodium), ALIQOPA® (Copanlisib Hydrochloride), ALKERAN® for Injection (Melphalan Hydrochloride), ALKERAN® Tablets (Melphalan), ALOXI® (Palonosetron Hydrochloride), ALUNBRIG® (Brigatinib), Ambochlorin (Chlorambucil), Amboclorin Chlorambucil), Amifostine, Aminolevulinic Acid, Anastrozole, Aprepitant, AREDIA® (Pamidronate Disodium), ARIMIDEX® (Anastrozole), AROMASIN® (Exemestane), ARRANON® (Nelarabine), Arsenic Trioxide, ARZERRA® (Ofatumumab), Asparaginase *Erwinia chrysanthemi*, Atezolizumab, AVASTIN® (Bevacizumab), Avelumab, Axitinib, Azacitidine, BAVENCIO® (Avelumab), BEACOPP, Becenum (Carmustine), BELEODAQ® (Belinostat), Belinostat, Bendamustine Hydrochloride, BEP, BESPONSA® (Inotuzumab Ozogamicin), Bevacizumab, Bexarotene, BEXXAR® (Tositumomab and Iodine I 131 Tositumomab), Bicalutamide, BiCNU (Carmustine), Bleomycin, Blinatumomab, BLINCYTO® (Blinatumomab), Bortezomib, BOSULIF® (Bosutinib), Bosutinib, Brentuximab Vedotin, Brigatinib, BuMel, Busulfan, BUSULFEX® (Busulfan), Cabazitaxel, CABOMETYX® (Cabozantinib-S-Malate), Cabozantinib-S-Malate, CAF, CAMPATH® (Alemtuzumab), CAMPTOSAR®, (Irinotecan Hydrochloride), Capecitabine, CAPOX, CARAC® (Fluorouracil—Topical), Carboplatin, CARBOPLATIN-TAXOL, Carfilzomib, CARMUBRIS® (Carmustine), Carmustine, Carmustine Implant, CASODEX® (Bicalutamide), CEM, Ceritinib, CERUBIDINE® (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, CLAFEN® (Cyclophosphamide), Clofarabine, Clofarex (Clofarabine), CLOLAR® (Clofarabine), CMF, Cobimetinib, COMETRIQ™ (Cabozantinib-S-Malate), Copanlisib Hydrochloride, COPDAC, COPP, COPP-ABV, COSMEGEN® (Dactinomycin), COTELLIC® (Cobimetinib), Crizotinib, CVP, Cyclophosphamide, Cyfos (Ifosfamide), CYRAMZA® (Ramucirumab), Cytarabine, Cytarabine Liposome, CYTOSAR®-U (Cytarabine), CYTOXAN® (Cyclophosphamide), Dabrafenib, Dacarbazine, DACOGEN® (Decitabine), Dactinomycin, Daratumumab, DARZALEX® (Daratumumab), Dasatinib, Daunorubicin Hydrochloride, Daunorubicin Hydrochloride and Cytarabine Liposome, Decitabine, Defibrotide Sodium, DEFITELIO® (Defibrotide Sodium), Degarelix, Denileukin Diftitox, Denosumab, DEPOCYT® (Cytarabine Liposome), Dexamethasone, Dexrazoxane Hydrochloride, Dinutuximab, Docetaxel, DOXIL® (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, EFUDEX® (Fluorouracil—Topical), ELITEK® (Rasburicase), ELLENCE® (Epirubicin Hydrochloride), Elotuzumab, ELOXATIN® (Oxaliplatin), Eltrombopag Olamine, EMEND® (Aprepitant), EMPLICITI® (Elotuzumab), Enasidenib Mesylate, Enzalutamide, Epirubicin Hydrochloride, EPOCH, ERBITUX® (Cetuximab), Eribulin Mesylate, ERIVEDGE (Vismodegib), Erlotinib Hydrochloride, ERWINAZE® (Asparaginase *Erwinia chrysanthemi*), ETHYOL® (Amifostine), ETOPOPHOS® (Etoposide Phosphate), Etoposide, Etoposide Phosphate, EVACET® (Doxorubicin Hydrochloride Liposome), Everolimus, EVISTA®, (Raloxifene Hydrochloride), EVOMELA® (Melphalan Hydrochloride), Exemestane, 5-FU (Fluorouracil Injection), 5-FU (Fluorouracil—Topical), FARESTON® (Toremifene), FARYDAK® (Panobinostat), FASLODEX® (Fulvestrant), FEC, FEMARA® (Letrozole), Filgrastim, FLUDARA® (Fludarabine Phosphate), Fludarabine Phosphate, FLUOROPLEX® (Fluorouracil—Topical), Fluorouracil Injection, Fluorouracil—Topical, Flutamide, FOLEX® (Methotrexate), FOLEX® PFS (Methotrexate), FOLFIRI, FOLFIRI-BEVACIZUMAB, FOLFIRI-CETUXIMAB, FOLFIRINOX, FOLFOX, FOLOTYN® (Pralatrexate), FU-LV, Fulvestrant, GARDASIL® (Recombinant HPV Quadrivalent Vaccine), GARDASIL® 9 (Recombinant HPV Nonavalent Vaccine), GAZYVA® (Obinutuzumab), Gefitinib, Gemcitabine Hydrochloride, GEMCITABINE-CISPLATIN, GEMCITABINE-OXALIPLATIN, Gemtuzumab Ozogamicin, GEMZAR® (Gemcitabine Hydrochloride), GILOTRIF® (Afatinib Dimaleate), GLEEVEC® (Imatinib Mesylate), GLIADEL® (Carmustine Implant), GLIA- DEL®) wafer (Carmustine Implant), Glucarpidase, Goserelin Acetate, HALAVEN® (Eribulin Mesylate), HEMANGEOL® (Propranolol Hydrochloride), HERCEPTIN® (Trastuzumab), HPV Bivalent Vaccine, Recombinant, HPV Nonavalent Vaccine, Recombinant, HPV Quadrivalent Vaccine, Recombinant, HYCAMTIN® (Topotecan Hydrochloride), HYDREA® (Hydroxyurea), Hydroxyurea, Hyper-CVAD, IBRANCE® (Palbociclib), Ibritumomab Tiuxetan, Ibrutinib, ICE, ICLUSIG® (Ponatinib Hydrochloride), IDAMYCIN® (Idarubicin Hydrochloride), Idarubicin Hydrochloride, Idelalisib, IDHIFA® (Enasidenib Mesylate), Ifex (Ifosfamide), Ifosfamide, Ifosfamidum (Ifosfamide), IL-2 (Aldesleukin), Imatinib Mesylate, IMBRUVICA® (Ibrutinib), IMFINZI® (Durvalumab), Imiquimod, IMLYGIC® (Talimogene Laherparepvec), INLYTA® (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, IRESSA® (Gefitinib), Irinotecan Hydrochloride, Irinotecan Hydrochloride Liposome, ISTODAX® (Romidepsin), Ixabepilone, Ixazomib Citrate, IXEMPRA® (Ixabepilone), JAKAFI® (Ruxolitinib Phosphate), JEB, JEVTANA® (Cabazitaxel), KADCYLA® (Ado-Trastuzumab Emtansine), Keoxifene (Raloxifene Hydrochloride), KEPIVANCE® (Palifermin), KEYTRUDA® (Pembrolizumab), KISQALI® (Ribociclib), KYMRIAH® (Tisagenlecleucel), KYPROLIS®) (Carfilzomib), Lanreotide Acetate, Lapatinib Ditosylate, LARTRUVO™ (Olaratumab), Lenalidomide, Lenvatinib Mesylate, LENVIMA® (Lenvatinib Mesylate), Letrozole, Leucovorin Calcium, LEUKERAN® (Chlorambucil), Leuprolide Acetate, LEUSTATIN® (Cladribine), LEVULAN® (Aminolevulinic Acid), Linfolizin (Chlorambucil), LIPODOX® (Doxorubicin Hydrochloride Liposome), Lomustine, LONSURF® (Trifluridine and Tipiracil Hydrochloride), LUPRON® (Leuprolide Acetate), LUPRON®) Depot (Leuprolide Acetate), LUPRON®) Depot-Ped (Leuprolide Acetate), LYNPARZA® (Olaparib), MARQIBO® (Vincristine Sulfate Liposome), MATULANE® (Procarbazine Hydrochloride), Mechlorethamine Hydrochloride, Megestrol Acetate, MEKINIST® (Trametinib), Melphalan, Melphalan Hydrochloride, Mercaptopurine, Mesna, MESNEX® (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, MITOZYTREX™ (Mitomycin C), MOPP, MOZOBIL® (Plerixafor), MUSTARGEN® (Mechlorethamine Hydrochloride), MUTAMYCIN® (Mitomycin C), MYLERAN® (Busulfan), Mylosar (Azacitidine), MYLOTARG™ (Gemtuzumab Ozogamicin), Nanoparticle Paclitaxel (Paclitaxel Albumin-stabilized Nanoparticle Formulation), NAVELBINE® (Vinorelbine Tartrate), Necitumumab, Nelarabine, Neosar (Cyclophosphamide), Neratinib Maleate, NERLYNX® (Neratinib Maleate), Netupitant and Palonosetron Hydrochloride, NEULASTA® (Pegfilgrastim), NEUPOGEN® (Filgrastim), NEXAVAR® (Sorafenib Tosylate), NILANDRON® (Nilutamide), Nilotinib, Nilutamide, NINLARO® (Ixazomib Citrate), Niraparib Tosylate Monohydrate, Nivolumab, NOLVADEX® (Tamoxifen Citrate), NPLATE® (Romiplostim), Obinutuzumab, ODOMZO® (Sonidegib), OEPA, Ofatumumab, OFF, Olaparib, Olaratumab, Omacetaxine Mepesuccinate, ONCASPAR® (Pegaspargase), Ondansetron Hydrochloride, ONIVYDE® (Irinotecan Hydrochloride Liposome), ONTAK® (Denileukin Diftitox), OPDIVO® (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), PARAPLATIN® (Carboplatin), Pazopanib Hydrochloride, PCV, PEB, Pegaspargase, Pegfilgrastim, Peginterferon Alfa-2b, PEGINTRON® (Peginterferon Alfa-2b), Pembrolizumab, Pemetrexed Disodium, PERJETA® (Pertuzumab), Pertuzumab, PLATINOL® (Cisplatin), PLATINOL®-AQ (Cisplatin), Plerixafor, Pomalidomide, POMALYST® (Pomalidomide), Ponatinib Hydrochloride, PORTRAZZA® (Necitumumab), Pralatrexate, Prednisone, Procarbazine Hydrochloride, PROLEUKIN® (Aldesleukin), PROLIA® (Denosumab), PROMACTA® (Eltrombopag Olamine), Propranolol Hydrochloride, PROVENGE® (Sipuleucel-T), PURINETHOL® (Mercaptopurine), PURIXAN® (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, RELISTOR® (Methylnaltrexone Bromide), R-EPOCH, REVLIMID® (Lenalidomide), RHEUMATREX® (Methotrexate), Ribociclib, R-ICE, RITUXAN® (Rituximab), RITUXAN HYCELA® (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), RUBRACA® (Rucaparib Camsylate), Rucaparib Camsylate, Ruxolitinib Phosphate, RYDAPT® (Midostaurin), SCLEROSOL®) Intrapleural Aerosol (Talc), Siltuximab, Sipuleucel-T, SOMATULINE® Depot (Lanreotide Acetate), Sonidegib, Sorafenib Tosylate, SPRYCEL® (Dasatinib), STANFORD V, Sterile Talc Powder (Talc), STERITALC® (Talc), STIVARGA® (Regorafenib), Sunitinib Malate, SUTENT® (Sunitinib Malate), SYLATRON™ (Peginterferon Alfa-2b), SYLVANT® (Siltuximab), SYNRIBO® (Omacetaxine Mepesuccinate), TABLOID® (Thioguanine), TAC, TAFINLAR® (Dabrafenib), TAGRISSO® (Osimertinib), Talc, Talimogene Laherparepvec, Tamoxifen Citrate, Tarabine PFS (Cytarabine), TARCEVA® (Erlotinib Hydrochloride), TARGRETIN® (Bexarotene), TASIGNA® (Nilotinib), TAXOL® (Paclitaxel), TAXOTERE® (Docetaxel), TECENTRIQ® (Atezolizumab), TEMODAR® (Temozolomide), Temozolomide, Temsirolimus, Thalidomide, THALOMID® (Thalidomide), Thioguanine, Thiotepa, Tisagenlecleucel, TOLAK® (Fluorouracil—Topical), Topotecan Hydrochloride, Toremifene, TORISEL® (Temsirolimus), Tositumomab and Iodine I 131 Tositumomab, TOTECT® (Dexrazoxane Hydrochloride), TPF, Trabectedin, Trametinib, Trastuzumab, TREANDA® (Bendamustine Hydrochloride), Trifluridine and Tipiracil Hydrochloride, TRISENOX® (Arsenic Trioxide), TYKERB® (Lapatinib Ditosylate), UNITUXIN® (Dinutuximab), Uridine Triacetate, VAC, Vandetanib, VAMP, VARUBI® (Rolapitant Hydrochloride), VECTIBIX® (Panitumumab), VeIP, VELBAN® (Vinblastine Sulfate), VELCADE® (Bortezomib), Velsar (Vinblastine Sulfate), Vemurafenib, VENCLEXTA® (Venetoclax), Venetoclax, VERZENIO® (Abemaciclib), VIADUR® (Leuprolide Acetate), VIDAZA® (Azacitidine), Vinblastine Sulfate, VINCASAR PES® (Vincristine Sulfate), Vincristine Sulfate, Vincristine Sulfate Liposome, Vinorelbine Tartrate, VIP, Vismodegib, VISTOGARD® (Uridine Triacetate), VORAXAZE® (Glucarpidase), Vorinostat, VOTRIENT® (Pazopanib Hydrochloride), VYXEOS® (Daunorubicin Hydrochloride and Cytarabine Liposome), Wellcovorin (Leucovorin Calcium), XALKORI® (Crizotinib), XELODA® (Capecitabine), XELIRI, XELOX, XGEVA® (Denosumab), XOFIGO® (Radium 223 Dichloride), XTANDI®) (Enzalutamide), YERVOY® (Ipilimumab), YONDELIS® (Trabectedin), ZALTRAP® (Ziv-Aflibercept), ZARXIO® (Filgrastim), Zejula (Niraparib Tosylate Monohydrate), ZELBORAF® (Vemurafenib), ZEVALIN® (Ibritumomab Tiuxetan), ZIN-ECARD® (Dexrazoxane Hydrochloride), Ziv-Aflibercept, ZOFRAN® (Ondansetron Hydrochloride), ZOLADEX®) (Goserelin Acetate), Zoledronic Acid, ZOLINZA® (Vorinostat), ZOMETA® (Zoledronic Acid), ZYDELIG® (Idelalisib), ZYKADIA® (Ceritinib), and/or ZYTIGA® (Abiraterone Acetate). Also contemplated herein are chemotherapeutics that are checkpoint inhibitiors, such as, for example, PD1/PDL1 blockade inhibitors and/or CTLA4/B7-1 or 2 inhibitors (such as, for example, PD-1 inhibitors lambrolizumab, OPDIVO® (Nivolumab), KEYTRUDA® (pembrolizumab), and pidilizumab; PD-L1 inhibitors BMS-936559, TECENTRIQ® (Atezolizumab), IMFINZI® (Durvalumab), and BAVENCIO® (Avelumab); and CTLA-4 inhibitors YERVOY® (ipilimumab). In one aspect, the CD4+ T cell mediated therapy can comprise adoptive cell therapies, and CAR T therapies. Accordingly, disclosed herein are methods of treating, inhibiting, decreasing, reducing, ameliorating, and/or preventing a cancer or metastasis (such as, for example, a melanoma) in a subject comprising administering to the subject i) an immune checkpoint blockade inhibitor (such as, for example, the PD-1 inhibitors lambrolizumab, OPDIVO® (Nivolumab), KEYTRUDA® (pembrolizumab), and/or pidilizumab; the PD-L1 inhibitors BMS-936559, TECENTRIQ® (Atezolizumab), IMFINZI® (Durvalumab), and/or BAVENCIO® (Avelumab); and/or the CTLA-4 inhibitor YERVOY® (ipilimumab)) and ii) an agent that an agent that modulates (including increases) the amount of fucosylation on the cell (such as a fucose including, but not limited to L-fucose, D-fucose, fucoidan, fucose-1-phosphate, GDP-L-fucose, or L-fucose/GDP-L-fucose analogues). In one aspect, the fucose can be administered before and/or during administration of the anti-cancer agent.

Also disclosed herein are methods of treating, inhibiting, decreasing, reducing, ameliorating, and/or preventing a cancer or metastasis (such as, for example, melanoma) in a subject comprising administering to the subject i) an immune checkpoint blockade inhibitor (such as, for example, the PD-1 inhibitors lambrolizumab, OPDIVO® (Nivolumab), KEYTRUDA® (pembrolizumab), and/or pidilizumab; the PD-L1 inhibitors BMS-936559, TECEN-TRIQ® (Atezolizumab), IMFINZI® (Durvalumab), and/or BAVENCIO® (Avelumab); and/or the CTLA-4 inhibitor YERVOY® (ipilimumab)) and ii) an agent that an agent that modulates the amount of fucosylation (such as a fucose including, but not limited to L-fucose, D-fucose, fucoidan, fucose-1-phosphate, GDP-L-fucose, or L-fucose/GDP-L-fucose analogues). In one aspect, disclosed herein are methods of treating, inhibiting, decreasing, reducing, ameliorating, and/or preventing a cancer or metastasis in a subject can further comprise harvesting tumor infiltrating lymphocytes (TILs), chimeric antigen receptor (CAR) T cells, or marrow infiltrating lymphocytes (MILs), contacting TILs, CAR T cells, and/or MILs with the agent that modulates fucosylation, and administering to the subject the TILs, CAR T cells, and/or MILs that have been contacted with the agent.

The combination of fucose and an anti-cancer agent can be formulated in the same composition of separately. Where separate, the fucose can be administered before, after, or concurrently with the anti-cancer agent. Administration of fucose can be accomplished prophylactically or therapeutically.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

C. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: Fucosylation and Immune Surveillance

Fucosylation has an important role in immune suppression of melanoma tumors. To determine whether cellular fucosylation correlates with melanoma progression, a melanoma tumor tissue microarray containing over 300 patient tumor biopsies was immunostained using UEA1, a lectin that binds to fucosylated proteins (green), and HMB45/S100 cocktail, specific markers for melanoma cells (red). UEA1 signals were measured within HMB45/S100-positive melanoma cells and correlated UEA1 intensity with melanoma progression. A ~50% reduction in fucosylation in metastatic compared with primary lesions was observed. To determine whether fucosylation levels correlate with survival outcome, primary tumor specimens were dichotomized according to high vs. low UEA1 signals and analyzed their correlation with survival probability (FIG. 1).

Figures 2A, 2B, 2C, 2D:
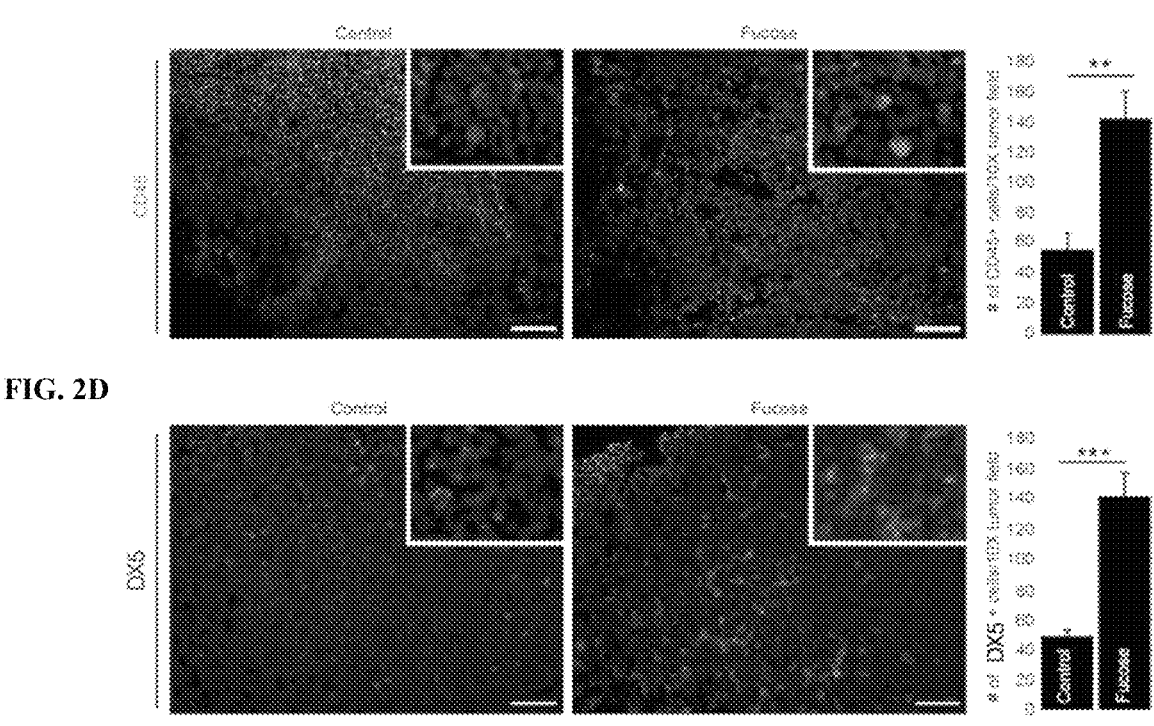

To determine whether dietary or genetic modulation of fucosylation affects tumor growth and metastasis, we previously studied a mouse melanoma model in which tumor fucosylation was increased either by dietary supplementation (FIG. 2A) with 100 mM fucose or by overexpressing mouse FUK (FIG. 2B). Increasing fucose irrespective of route resulted in increased tumor suppression. To determine whether fucosylation affects tumor infiltration by immune cells, Immunofluorescent staining analysis of CD45 (general leukocyte marker, red) and DAPI (blue) was performed (FIG. 2C). To determine whether fucosylation affects tumor infiltration by NK cells, immunofluorescent staining analysis for DX5 (an NK cell marker, red) and DAPI (blue) was performed (FIG. 2D). Both NK cells and CD4+ T cells were elevated in samples from fucose supplemented mice.

Figures 3A, 3B:
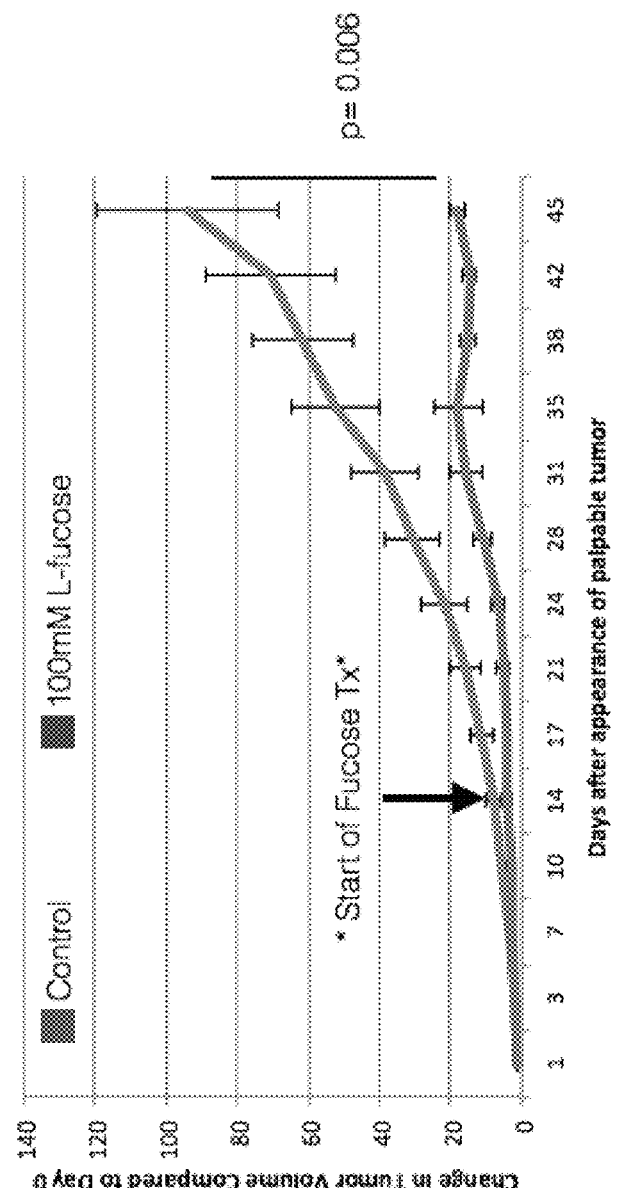
Figures 3C, 3D:
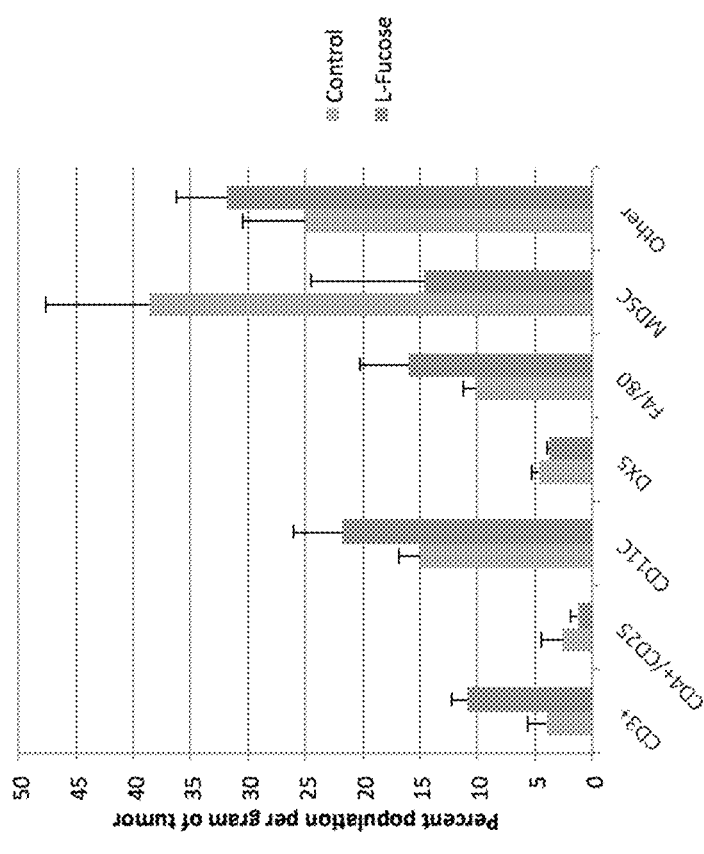

To determine which immune cell populations were affected by L-fucose, another mouse melanoma model treated with control or L-fucose-supplemented water was used. First, $1.25\times10^6$ SW1 mouse melanoma cells were injected into the back right flanks of the mice and allowed the tumors to grow to 150 mm³. At 150 mm³ (14 days), 100 mM L-fucose was administered via the drinking water to half of the mice. Tumor growth was monitored (FIGS. 3A and 3B). Total and specific subpopulations of tumor-infiltrating lymphocytes were assessed by cell flow cytometric analysis (FIGS. 3C and 3D). Assessed populations included F4/80 (macrophage)-, Gr-1 (MDSCs)-, Cd11c (Dendritic cells)-, and DX5 (NK cells)-positive cells. For T-cells, we probed for CD3 (general T-cell marker) and further for CD4 and CD8 (for those T cell subpopulations). Of the CD4-positive cells, CD25 positive cells was used to elucidate the T regulatory cells. The data show that overall immune infiltration of tumors is increased in response to dietary fucose supplementation. Both CD4 and CD8 positive T cells (CD3+ cells) increased in response to fucose. However, myeloid derived suppressor cells (MDSCs) decreased in response to dietary fucose supplementation.

Increasing fucosylation suppresses melanoma tumors, it was observed that the >50% reduction in tumor growth triggered by L-fucose supplementation is associated with significant increases in infiltration of tumors by CD45+ immune cells and natural killer (NK) cells. This SW1 melanoma tumor/C3H mouse isogenic model was recapitulated to profile—in detail—tumor-infiltrating immune populations. >65% reduced tumor growth was observed during dietary L-fucose supplementation (FIG. 4A). Flow cytometric analyses revealed that the tumors from L-fucose-supplemented mice contain 10-50-fold more infiltrating immune cells (per gram of tumor) than tumors from mice on control diet, indicating that fucosylation enhances immune suppression of tumors. Although most tumor-suppressive immune cell types were increased in the fucosylation-high, smaller tumors, tumor-infiltrating CD4+ and CD8+ T cells were most increased-doubled-in these tumors compared to control diet tumors (FIG. 4B, left and right). To determine whether CD4+ or CD8+ T cells are required for L-fucose-triggered melanoma tumor suppression, the melanoma mouse model above was repeated but added cohorts of mice in which either CD4+ or CD8+ T cells were immunodepleted. The immunodepletion models revealed that loss of CD4+ T cells significantly, but not CD8+ T cells, abrogated tumor suppression (FIG. 4C, left and right) and reduced numbers of intratumoral CD8+ T cells, CD11c+ dendritic cells (DCs), and NK cells (FIG. 4D), indicating that during L-fucose treatment, CD4+ T cells are required for intratumoral recruitment of these cell types to suppress tumor growth. The presence and cytolytic activity of CD4+ T cells in tumors has been correlated with better patient survival rates and increased responsiveness to immunotherapies, respectively.

The possibility that tumor fucosylation can directly activate the tumor cell-killing activity of NK cells was explored. To assay for this possibility, a lactate dehydrogenase (LDH)-release-based assay was used in which the fucosylation of LU1205 melanoma cells was modulated prior to co-culture with NK cells. Specifically, primary NK cells isolates (5A) or immortalized NK92 cell line (5B) were co-cultured with 1205Lu melanoma cells that were pre-treated with DMSO, 250 µM pan-fucosyltransferase inhibitor (FUTi), or 250 µM L-fucose for 8 hours. Non-radioactive LDH-release cytotoxicity assay was performed to measure extent of NK cell-mediated killing. The findings show that increasing tumor fucosylation alone is sufficient to induce the tumor-cell killing activity of both immortalized and primary human NK cells (FIGS. 5A and 5B). Immunoblot analysis using AAL lectin (another fucose-binding lectin) was performed to confirm the effects of FUTi (5C) or L-fucose (5D) on 1205Lu cells (96 h treatment). (•: p-value≥0.02) (*: p-value≥0.002).

To determine molecular mechanisms underlying the effects of fucosylation, a click-chemistry-based proteomic screen was perfomed to identify all fucosylated proteins in melanoma cells. 2 fucosylated immunomodulatory proteins, HLA-A and HLA-DRB1, were identified in melanoma cells. Fucose-binding lectin pulldown and immunoblot analysis confirmed the i) the expression and ii) the fucosylation of these 2 HLA proteins in melanoma cells, and further, indicate that their fucosylation is reduced when comparing patient-matched primary vs. metastatic cell lines (FIGS. 6A & 6C). The proximity ligation analysis technique, a cutting edge technique conventionally implemented to visualize 2 directly interacting proteins or post-translationally modified species of specific proteins when antibodies for the modifications are available (e.g., phosphorylated Tyr using an anti-phospho-Tyr antibody). However, as there are no antibodies specific for fucosylated moeities, biotinylated AAL, lectin and HLA-A- or HLA-DRB1-targeted antibodies were used to adapt generally double-layer PLA protocols into a triple-layer PLA protocol (a.k.a., lectin-mediated PLA, or L-PLA) to visualize fucosylated HLA-A and HLA-DRB1. The results reveal that fucosylated HLA-A and HLA-DRB1 localize to punctae throughout the cell (FIG. 6B). To further characterize the effects of fucosylation on HLA-A and HLA-DRB1, preliminary flow cytometric assessment of the cell surface presentation of these 2 proteins was performed. The results indicate that inhibiting global fucosylation results in the increased surface presentation of HLA-A and its binding partner, β2-microglobulin, whereas modulation of fucosylation did not appear to alter the surface presentation of HLA-DRB1 (FIG. 7). These data indicate that fucosylation suppresses the surface presentation of HLA-A.

Together, the data indicates roles for fucosylation and HLA-A/HLA-DRB1 in promoting immune cell-mediated melanoma cell killing. Reduced fucosylation, as is observed during melanoma progression, impairs immune surveillance of melanoma tumors. However, the observations highlight the potential implementation of dietary L-fucose supplementation as a non-toxic, effective therapeutic agent to boost immune-mediated suppression of melanoma tumors. L-fucose (pre-) supplementation can enhance the efficacy of current immunotherapeutic approaches (e.g., Nivolumab or TIL, therapy), particularly in patients who do not exhibit upfront responsiveness. The studies herein elucidate: (a) how fucosylation regulates HLA-A/HLA-DRB1 and the interaction between melanoma and CD4+ T cells (and other immune cells), and (b), whether fucosylation/fucosylated HLA-A/HLA-DRB1 correlates with responsiveness (clinical parameters) of melanomas to current immunotherapies (e.g., Nivolumab or TIL, therapy). The studies disclosed herein highlight how fucosylation/fucosylated HLA-A/HLA-DRB1 can be exploited as a novel adjuvant for therapeutic modalities and enhanced patient stratification, improving patient response rates and durations of response to immunotherapy.

a) Determination of how L-Fucose and Melanoma Tumor Fucosylation Affect CD4+ T Cell Biology and CD4+ T Cell-Dependent Tumor Suppression:

(1) Verify Altered CD4+ T Cell-Regulated TILs in Systemic L-Fucose Treatment Vs. Tumor-Specific Fucosylation CD4+ T cells are required for L-fucose-mediated melanoma tumor suppression (FIGS. 4B & 4C). However, the relative contribution of systemic fucosylation vs. tumor cell fucosylation (or both) to the tumor suppression observed are unclear. Mouse FUK was ectopically overexpressed in melanoma cells to increase tumor fucosylation and similar tumor suppression as dietary (systemic) L-fucose supplementation was observed. However, the precise contribution of tumor cell-specific fucosylation to the CD4+ T cell-mediated recruitment of other immune cell types and tumor suppression remains to be delineated. To address these issues, the model in FIGS. 4A and 4C can be repeated using SW1 mouse melanoma cells expressing either empty vector (control) or mouse Fuk (mFuk; to genetically increase fucosylation). Briefly, control empty vector (EV)- or mFuk-overexpressing SW1 murine melanoma cells can be injected into the rear flanks of C3H/HeJ mice. The mice can also be immunodepleted (or not) of CD4+ T cells as previously described. Mouse cohort number calculations are described in Data and Statistical Analysis Plan section. Upon reaching 1.5 cm², the tumors were harvested, and immune cells can be isolated and profiled by flow cytometry. Profiling markers included F4/80, CD11b, CD163, CD206 (macrophages and polarization); GR-1 (MDSCs); CD11c (DCs); CD14 (monocytes); CD3, CD4, CD8, CD25, FoxP3, CD69, 41BB, PD1, Tim-3, BTLA, and Lag-3 (T cells and activation, and Tregs), CD19 (B cells), and NKp46 (NK cells) (see FIG. 3D). This experiment addresses the question of systemic vs. tumor-specific fucosylation contribution, as well as CD4+ T cell-mediated alterations to tumor-infiltrating immune cell landscape.

(2) Determine Signaling Changes in CD4+ T Cells Induced by Tumor Fucosylation and Systemic L-Fucose To determine how fucose/fucosylation is affecting crucial signaling pathways in CD4+ T cells, phosphoproteomic analyses can be performed on CD4+ T cells isolated from either control or mFUK-expressing SW1 tumors or from SW1 tumors from mice treated ±dietary l-fucose as detailed above. The CD4+ T cells can be immediately harvested from the models above in parallel to flow studies above using standard antibody-magnetic bead-based isolation methods and subject to phosphoproteomic analyses, followed by Ingenuity Pathway Analysis. These analyses allow for unbiased global profiling to identify significant signaling changes induced in CD4+ T cells by both systemic fucose and melanoma tumor-specific fucosylation. CD4+ T cell signaling pathways found to be significantly altered by tumor fucosylation can be verified by IB and qRT-PCR analyses using the mouse CD4+ T cells harvested, as well as human CD4+ T cells.

(3) Investigate the Contribution of Dendritic Cells (DC) to CD4+ T Cell-Mediated Melanoma Suppression Given the observation of the L-fucose-triggered, CD4+ T cell-dependent increase in DC and NK cells, it is possible that CD4+ T cells are first stimulated by tumor fucosylation (i.e., fucosylated HLA) to recruit DCs, which facilitate antigen processing/presentation to recruit other immune subtypes including NK cells. To test the possibility that DC cells are crucial downstream effectors of CD4+ T cells in this context.

Control- or mFUK-expressing SW1 tumor or SW1 tumor±L-fucose supplementation models were conducted as above as detailed above, in which the mice can be subject to CD4+ T cell depletion (or not). In addition, the mice can be injected with (or not) an agonistic CD40 antibody that has been used in previous studies to activate DC cells. This approach can be used to activate DC cells independently of CD4+ T cell presence. The mice can be monitored for tumor growth, and effects on TILs can be assessed by flow as detailed above. Mouse cohort number calculations are described in Data and Statistical Analysis Plan section.

(4) Verification with Patient-Matched TIL-Derived CD4+T and Tumor Cells

In order to validate the findings relating the effects of fucosylation on CD4+ T cells, patient-matched T and tumor cells can be used. CD4+ T cells can be sorted from the patient T cells by magnetic bead method. Either the melanoma cells alone ("tumor autonomous fucosylation") or both the melanoma and CD4+ T cells ("systemic L-fucose treatment") can be pre-treated with DMSO (control), 250 μM FUTi, or 250 μM L-fucose to modulate fucosylation. The melanoma cells can then be co-cultured with the CD4+ T cells over a time course of 8 h. Every 2 h, co-culture CD4+ T cells can be harvested and assessed for activation analysis by ELISA for γ-IFN, as well as for markers of the signaling pathway(s) identified to be activated. Further, there are currently limited numbers (<30) of de-identified patient tumor digests that have been cryopreserved. In vitro co-culture cytotoxicity assays (as in FIG. 5) can be performed using the patient-matched tumor cell lines for those digests. The patient tumor cell lines can be pretreated with DMSO (control) 250 μM FUTi, or 250 μM L-fucose to modulate fucosylation, followed by co-culture using the TIL-containing patient-matched TILs. The requirement for CD4+ T cells can be verified in this in vitro assay by pre-immunodepleting the patient TILs (using magnetic bead method as previously indicated).

The studies disclosed herein delineate the crucial immune effects induced by systemic L-fucose vs. tumor cell-specific fucosylation. Further, these studies elucidate how fucosylation triggers CD4+ T cell activation (signaling changes) and infiltration into melanoma tumors by systemic fucose and tumor-specific fucosylation. The studies also delineate requirement/role of DCs downstream of CD4+ T cells in this scenario. Where DCs are a predominant and crucial downstream effector of CD4+ T cells, the CD40 agonistic antibody can rescue tumor suppression in dietary L-fucose-supplemented, CD4+ T cell immunodepleted mice.

b) Determine how Fucosylation of HLA-A/HLA-DRB1 Affects their Role in Melanoma: Immune Cell Interactions:

(1) Delineate Requirement of HLA-A/HLA-DRB1 in Fucosylation-Stimulated Tumor Suppression and CD4+ T Cell Recruitment, Verify In Vivo Observations In Vitro with De-Identified Patient-Derived TIL First, the requirement for HLA-A/HLA-DRB1 for recruitment/activation of CD4+ T cells was determined by fucosylation. Mouse HLA-A/HLA-DRB1 orthologs (a.k.a., H2K1 and H2EB1) can be knockeddown/overexpressed in SW1 cells that can be isografted into C3H/HeJ mice. Tumor growth can be monitored, and following tumor harvest, infiltrating immune cell populations can be profiled by flow cytometry. FFPE blocks and frozen portions of tumor and spleen can be used to verify the flow analyses (by IF staining and qRT-PCR for markers of immune cells of interest (i.e., CD4+ and CD8+ T cells, DCs, NK cells, etc.).

Next, in vitro co-culture assays can be performed using patient melanoma cell lines that can have knocked down for HLA-A or HLA-DRB1 (using control or targeted shRNAs) and co-cultured±L-fucose with patient-matched CD4+ T cells to assess CD4+ T cell activation. Activation of CD4+ T cells can be verified as described above. Similarly, co-culture cytotoxicity assays (as described in FIG. 5) can be performed using control or CD4+ T cell immunodepleted tumor digests with HLA-A- or HLA-DRB1-knocked down patient tumor-matched cell lines. Loss of either HLA-A or HLA-DRB1 is impairs CD4+T activation and TIL-mediated cell killing.

(2) Determine how Fucosylation Affects HLA-A/HLA-DRB1 Protein Stability, Subcellular Localization, Partner Binding, and Effects on Immune Cell Activity First, direct fucosylation can be confirmed using the following 2-pronged enzymatic and biochemical approach. HLA-A/HLA-DRB1 immunoprecipitated from control (DMSO) or FUTi-treated human melanoma (WM793 or WM1366) cells can be subjected to enzymatic sugar removal using 3 fucosidases (to remove α1,2; α1,3/4; or α1,2/3/4/6-linked fucose) or PNGaseF (to remove N'-linked glycans, followed by AAL, lectin pulldown and immunoblot (IB) analysis for HLA-A/HLA-DRB1, which implicates respective fucose linkages. FUTi can serve as a positive control to block fucosylation, reducing the amount of HLA-A/HLA-DRB1 pulled down by AAL. WM793/WM1366 can be used as they exhibit relatively higher fucosylation than others which allows for more significant chemical modulation of fucosylation. A click-chemistry fucose technique can be used to biotinylate fucosylated exogenously expressed, V5-tagged HLA-A/HLA-DRB1 and detect by V5-IP followed by IB for biotin. Briefly, V5-empty vector- or V5-HLA-A/HLA/DRB 1-expressing melanoma cells can be incubated with alkyne-fucose to label all cellular fucosylated proteins. Cells can be lysed and subject to a click reaction using azide-biotin to render fucosylated proteins as biotinylated. Lysates can be subject to V5-IP and IB for biotin (streptavidin) and HLA-A/HLA-DRB1 (simultaneous visualization can be performed using a Li-Cor system). Controls can include non-labeled cells and lysates subject to click reaction without azide-biotin. Visualization of a biotin-positive HLA-A/HLA-DRB1 bands confirms direct fucosylation. For robustness, experiments can be repeated in A375, LU1205, WM115, WM266-4, WM983A/B melanoma lines.

To identify requisite fucosylation sites, V5-tagged exogenously expressed HLA-A and HLA-DRB1 were purified from melanoma cells and subject them to mass spectrometric analysis. In addition, fucosylation site prediction software was used to predict putative fucosylation sites on HLA-A (N110 and T206) and HLA-DRB1 (N48 and T129). Based on these predictions, site (alanine) mutants were generated for each predicted site to abolish potential fucosylation. Upon confirmation of the site(s), these "fucomutants" constructs can be used for reconstitution into melanoma cell lines to evaluate how site-specific fucosylation affects behavior and function of HLA-A/HLA-DRB1.

To assess how fucosylation affects the protein stability of HLA-A/HLA-DRB1, WM793 or WM1366 are treated with DMSO (control), 250 μM FUTi, or 250 μM L-fucose to modulate fucosylation, followed by immunoblot analysis for total levels of HLA-A/HLA-DRB1. This experiment reveals changes in steady-state levels of HLA-A/HLA-DRB1. To further assay changes in HLA-A/HLA-DRB1 protein degradation dynamics, cyclohexamide (CHX) chases can be performed (timecourses where cells are treated with DMSO/FUTi/L-fucose in the presence of CHX, which blocks protein translation/production) or MG132 blocks (where cells are treated with DMSO/FUTi/L-fucose in the presence of MG132, which blocks proteosomal degradation). These experiments can be repeated with exogenous fucomutant HLA-A/HLA-DRB1 constructs to confirm that the exogenous constructs behave the same as the endogenous HLAs. These experiments reveal changes (if any) in the half-life and degradation rates of HLA-A/HLA-DRB1 induced by altered fucosylation.

Next, the effects of fucosylation on subcellular localization (and thus function/plasma membrane presentation) of HLA-A/HLA-DRB1 can be tested. Standard immunofluorescence cytochemistry is performed using antibodies against these proteins, as well as L-PLA, on DMSO (control)-, 250 μM FUTi-, or 250 μM L-fucose-treated WM793 and WM1366 cells using lectin- and protein-targeted antibodies followed by immunofluorescent microscopy and ImageJ (NIH) analysis of puncta. Conventional PLA immunofluorescence technique was successfully modified to using fucose-binding AAL lectin (FIG. 4). The results can be further verified on cells treated as detailed above by more in-depth cell surface flow cytometric analyses as described in (FIG. 5). These experiments can be repeated with exogenous fucomutant HLA-A/HLA-DRB 1 constructs to confirm that the exogenous constructs behave the same as the endogenous HLAs.

To examine how fucosylation affects partner binding of HLA-A and HLA-DRB1, the V5-tagged WT vs. fucomutant HLA constructs can be expressed, perform V5 IP, followed by IB for known partners. For HLA-A, partners can include β2-microglobulin, and for HLA-DRB1, partners can include HLA-DRAI or LAG3 (to be assessed by in vitro pullday assay using V5-HLA-DRB1 and immune cell lysates).

To verify that the crucial role that site-specific fucosylation plays in CD4+T activation, de-identified patient-derived melanoma cells can be modified to express wild-type vs. fucomutant HLAs (the patient's HLA-A and HLA-DRB1 can be cloned from their melanoma cell's cDNA). The melanoma cells can be co-cultured with the patient-matched CD4+ T cells over a timecourse of 8 h and assessed for CD4+ T cell activation.

(3) Assess Clinical Correlations Between General Fucosylation and Fucosylated HLA-A/HLA-DRB1 in Nivolumab- or TIL Therapy-Treated Patient Samples.

Lastly, how general melanoma tumor fucosylation vs. fucosylated HLA-A/HLA-DRB1 correlates with clinical parameters (e.g., overall survival or progression-free survival) in Nivolumab or TIL therapy-treated patients can be assessed. This is important for determing whether general tumor fucosylation vs. HLA fucosylation has prognostic utility for immunotherapy in melanoma. Immunostaining analysis of the FFPE samples can be performed for AAL/UEA1 lectin and HLA-A/HLA-DRB1 (total and fucosylated (by lectin-PLA, as in FIG. 6B). The tumor sections can be counterstained with MARTI, a melanoma marker. Stained tumors are imaged, and lectin/HLA-A/HLA-DRB1/and fucosylated HLA-A/HLA-DRB1 signal intensities are blindly scored from within MARTI-positive regions only. The tumor-specific intensities are analyzed for correlation with clinical parameters (e.g., overall survival/time to progression/progression-free survival).

The studies disclosed herein elucidate the role(s) of fucosylation in the regulation of HLA-A/HLA-DRB1. The MS efforts at identifying HLA-A/HLA-DRB1 fucosylation sites allow for the generation of fucomutants for functional studies. The studies shown herein allowed for the determination of whether overall tumor fucosylation, as well as the specific fucosylation of HLA-A and HLA-DRB1, correlate with patient responsiveness to Nivolumab and/or TIL, therapy. These findings provide the basis for an efficient patient stratification approach for Nivolumab/TIL, therapy using general tumor fucosylation and/or fucosylated HLA-A/HLA-DRB1. L-fucose supplementation mouse model provides support for the concept that L-fucose is an effective and safe adjuvant agent for Nivolumab/TIL, therapy. Importantly, the results provide the basis for an adjuvant utility of L-fucose for other immunotherapies in other cancers.

2. Example 2: Fucosylated DRB1: A Biomarker for Checkpoint Inhibitors

HLA-DRB1 is expressed (FIG. 8A) and fucosylated (FIG. 8B) in melanoma cells. shRNA knockdown of the mouse ortholog of HLA-DRB1 (IEB in this mouse model) abrogates L-fucose-triggered tumor suppression vs. control shRNA (SCR) in the SW1 mouse melanoma: syngeneic C3H/HeJ mouse model (FIG. 8C), indicating that HLA-DRB1 is required for L-fucose-triggered tumor suppression. Fucosylation of HLA-DRB1 occurs on amino acid N48 (mutation to G abolishes interaction with fucose-binding AAL, lectin) (FIG. 9A). Increasing fucosylation (L-fucose treatment) promotes cell surface abundance of HLA-DRB1 (which is expected to increase CD4+ T cell activation) (FIG. 9B). Oral L-fucose suppresses melanoma growth in the SW1/C3H/HeJ model more significantly than anti-CTLA4 or anti-PD1 alone (FIG. 10). L-fucose+anti-PD1 appears to have improved efficacy over anti-PD1 at this timepoint (FIG. 10B). Given longer co-treatment, L-fucose+anti-PD1 can exhibit significant tumor suppression. To further investigate the efficacy of the combination therapy of L-fucose and anti-PD1 and to see if the combination of L-fucose and anti-PD1 improved the efficacy of either agent alone, two mouse melanoma mouse models were used. The first was the NRAS-mutant melanoma mouse model. Here, C3H mice were pretreated with anti-PD1 and/or L-fucose or a L-fucose pre-dose followed by anti-PD1 antibody (FIG. 11). Mice receiving L-fucose or anti-PD1 were able to effectively control the tumor. At early time points, because anti-PD1 and L-fucose effectively suppressed tumor growth a significant improvement with combination therapy was not observed. However, 45 days after tumor challenge, combination therapies did show a marginal improvement over anti-PD1 therapy alone. Using a BRAF-mutant melanoma model, the efficacy of the combination therapy was more pronounced. Here C57BL6 mice were challenged with SMI cells (FIG. 11). 7 days post challenge, mice received either a control, anti-PD1, L-fucose, or L-fucose and anti-PD1. Within 3 days post administration, the combination therapy showed a statistically significant improvement over either L-fucose or anti-PD1 treatment alone. Thus, L-fucose is either able to suppress tumors as well as anti-PD1 and/or augment the efficacy of anti-PD1.

Example 3: Modulation of MHC Class II Presentation

Figure 12:
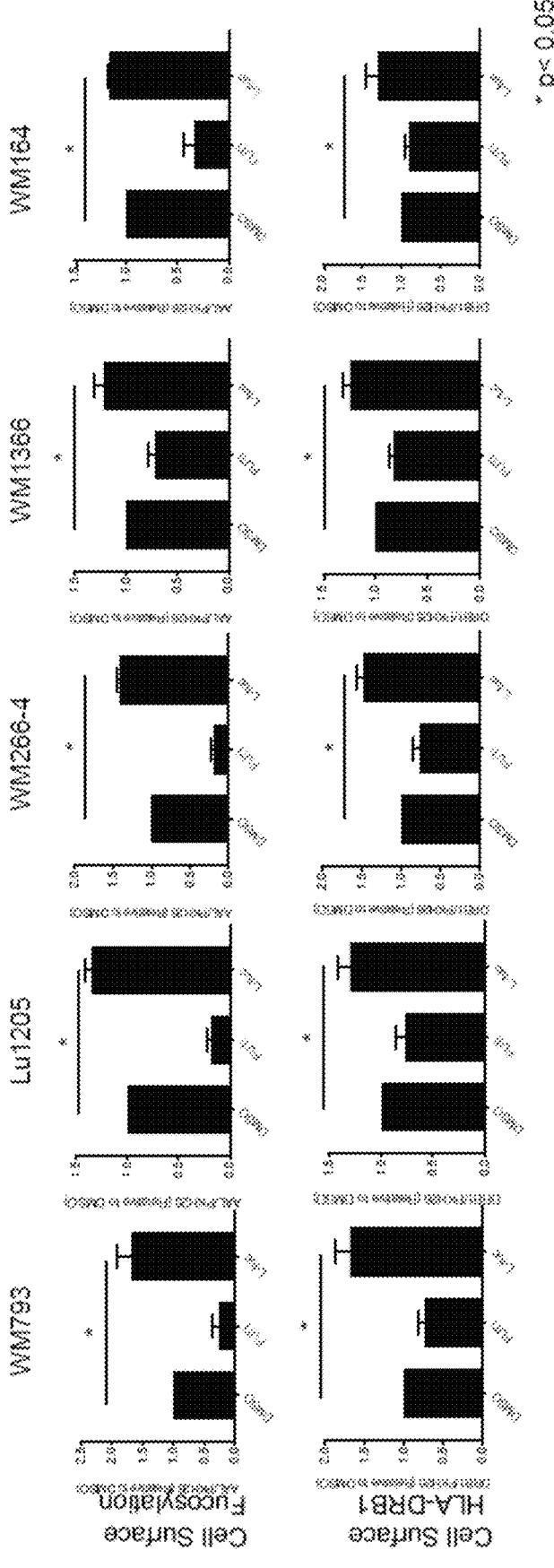
FIG. 12 shows that modulation of fucosylation propor-
tionately modulates cell surface levels of HLA-DRB1.

Experiments provided herein showed that HLA-DRB1 is expressed (FIG. 8A) and fucosylated (FIG. 8B) in melanoma cells and required for L-fucose-triggered tumor suppression in the C3H/HeJ mouse model. To determine if the effect of L-fucose on surface fucosylation and on HLA-DRB1 expression was limited to a particular cell type, WM793, Lu1205, WM266-4, WM1366, and WM164 cells were incubated in the presence of DMSO, the fucosylation inhibitor FUTi (2-fluoro-fucose), or L-fucose (FIG. 12). In all cell types cell surface fucosylation was increased by administration of L-fucose or decreased by administration of FUTi relative to control cells. Additionally, the surface expression levels of HLA-DRB1 was modulated with the addition of L-fucose (increased) or FUTi (HLA-DRB1 expression suppressed).

Figure 13:
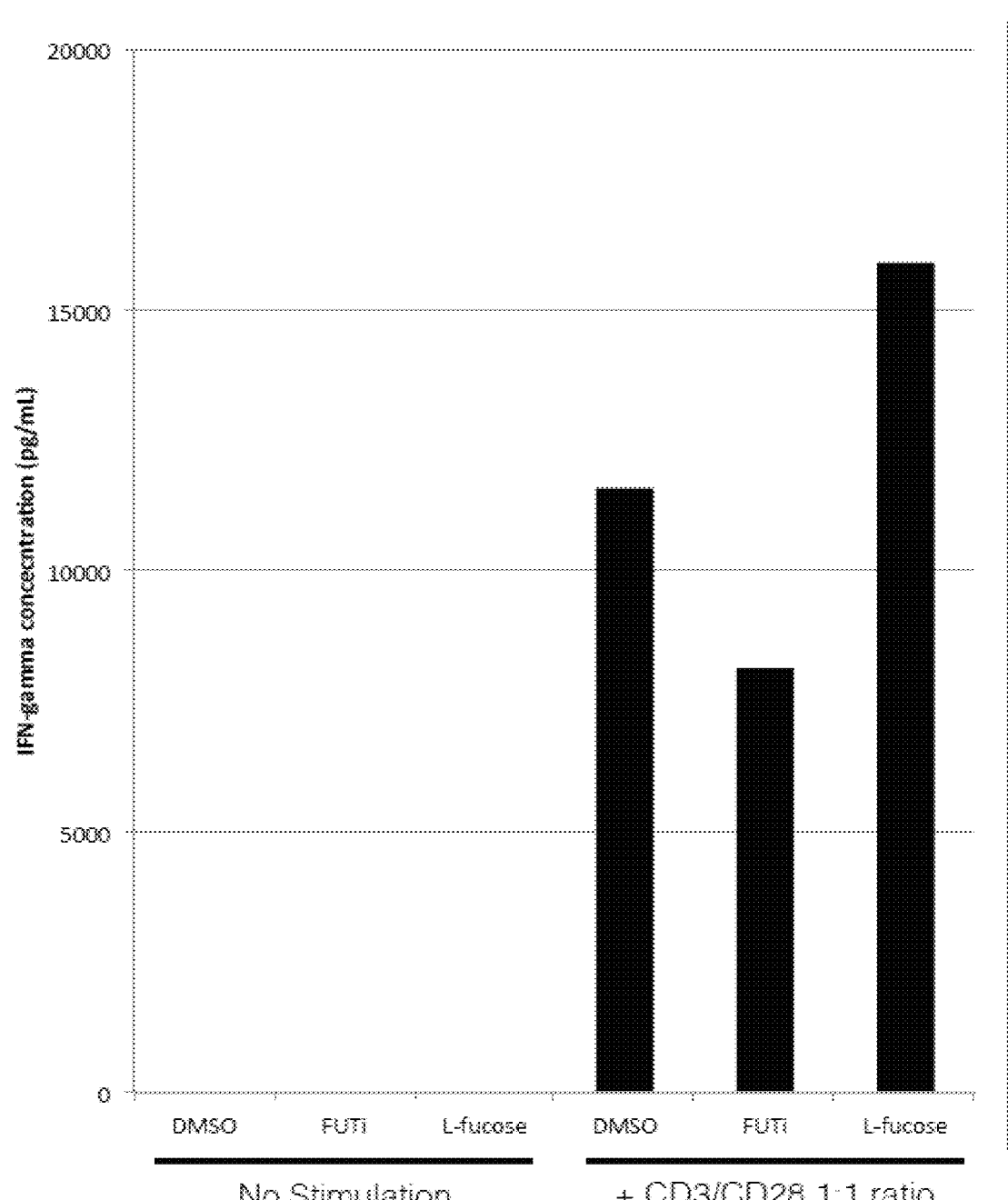
FIG. 13 shows that modulation of global fucosylation in
CD4+ T cells proportionately alters their activation capacity.

As HLA-DRB1 is an MHC class II molecule and plays a critical role in CD4+ T cell activation, experiments were conducted to determine if the modulation of HLA-DRB1 would proportionately modulate activation of CD4+ T cells. Using IFN-γ as the measure for T cell activation, cells receiving L-fucose saw an increase in IFN-γ production whereas FUTi treated cells showed a decrease in IFN-γ production relative to DMSO treated controls (FIG. 13). This indicates that increasing fucosylation augments the activation status of CD4+ T cells, whereas suppressing fucosylation suppresses the activation of CD4+ T cells. Because CD4+ T cell activation and response play such an important roll in many therapeutic approaches, it is evident that increasing CD4+ T cell activation by increasing fucosylation can enhance CD4 T cell mediated therapeutic approaches such as TILs, CAR T cells, and immune checkpoint blockade.

Example 4: N-Linked Fucosylation of HLA-DRB1 in Melanoma Triggers CD4+ T Cell-Mediated Anti-Tumor Immunity a) Results
(1) Increasing Melanoma Fucosylation Reduces Tumor Growth and Increases TIL Abundance, Particularly CD4+ and CD8+ T Cells Increasing tumor fucosylation (by dietary or genetic manipulation) in an immunocompetent mouse melanoma model increases CD45+ tumor-infiltrating lymphocytes (TILs) and suppressed tumor growth and metastasis (ref. 18). To determine how L-fuc-triggered increases in TILs can contribute to tumor suppression, we assessed L-fuc-induced changes in intratumoral immune landscape in the NRAS-mutant SW1 mouse melanoma model. L-fuc supplementation increased tumor fucosylation (~2.25-fold; FIG. 14A) and reduced tumor growth (~50%) (FIG. 15A). Flow cytometric profiling revealed that L-fuc triggered ~10-50-fold increases in total TIL counts (FIG. 15B), without significant changes in splenic lymphocyte profiles (FIG. 14B). Absolute counts of each TIL subpopulation (e.g., CD3+ T cells, dendritic cells (DCs), natural killer cells (NKs), macrophages (MP), and myeloid-derived suppressor (like)-cells (MDSCs) were increased by L-fuc (FIG. 14C). To determine which specific subpopulation(s) was most significantly increased by L-fuc (and thus likely to mediate tumor suppression), we compared pre- and post-L-fuc changes in individual subpopulations as a percentage of total TIL (FIG. 15C). CD3+ T cells—specifically CD4+ and CD8+ subsets—were most increased, doubling compared to other subpopulations (FIG. 15D). Subpopulations known to promote tumors (i.e., MDSCs (FIG. 15C)) were either decreased or low.

As only ~20% of all melanomas are driven by mutant NRAS, whereas ~60% are driven by mutant BRAF (ref. 12), we sought to determine if L-fuc elicits similar effects in the mutant BRAF$^{V600E}$ SM1 mouse melanoma model. L-fucose supplementation increased tumor fucosylation by ~4-fold (FIG. 14D) and decreased tumor volume by ~60% (FIG. 15E). Consistently, L-fuc induced ~10- and ~15-fold increases in total TILs and the CD3+ T cell subpopulation, respectively (FIGS. 15F & 15G). CD4+ and CD8+ T cells were again most increased, by ~10-100-fold, in response to L-fuc (FIG. 15H). L-fuc did not significantly alter splenic lymphocyte profiles (FIG. 14E), whereas it again significantly increased absolute counts of each TIL subpopulation (FIG. 14F).

Although these data show that L-fuc can increase TILs, particularly CD4+ and CD8+ T cells, and reduce tumor growth in both BRAF- and NRAS-mutant melanomas, whether tumor fucosylation alone is sufficient for these effects was unclear. To delineate contributions of tumor-specific fucosylation from those of systemic fucosylation (stimulated by dietary L-fuc), we overexpressed murine fucokinase (mFuk) to increase fucosylation exclusively in SW1 cells. mFuk alone increased tumor fucosylation by 4-fold and suppressed tumor growth by ~60% (FIGS. 14G and 15I, respectively). It also increased absolute TILs by ~10-fold (FIG. 15J). Consistent with FIG. 15A, L-fuc reduced growth of EV tumors by ~50% (FIG. 15I), while doubling total TILs (FIG. 15J). Whereas absolute TIL, subpopulation counts were also generally increased (FIG. 14H), CD3$^+$ T cells were again most increased (~doubling) (FIG. 15K), where absolute CD4$^+$ and CD8$^+$ T cell counts increased by ~15-fold (FIG. 15L). No additive effects were observed in mFuk tumors supplemented with L-fuc, which indicate downstream limiting factors (e.g., fucosyltransferase expression).

To determine the requirement of the L-fuc-induced TILs to tumor suppression, we assessed the growth of SW1 tumors in immunodeficient NSG mice fed with or without L-fuc. There were no significant differences in tumor growth (FIG. 15M), indicating that the immune system is required for L-fuc-triggered tumor suppression.

The findings herein indicate that tumor fucosylation can significantly influence the intratumoral presence of CD3$^+$ T cells and other TILs, which has important implications in the diagnosis and treatment of melanoma in humans. Thus, we assessed if there is a correlation between intratumoral fucosylation and CD3$^+$ T cells in humans. We immunofluorescently stained and analyzed a melanoma tumor microarray (n=41 patients) for melanoma-specific fucosylation and CD3$^+$ T cells. Patients with higher than median levels of melanoma-specific fucosylation exhibited significantly higher intratumoral density of CD3$^+$ T cells (P-value=0.025, Wilcoxon rank sum test; FIG. 15N). This association remained statistically significant after adjusting for potential confounding factors including age, sex, and stage (P-value=0.035, multivariable linear regression). Interestingly, sex was identified by regression analysis as a significant covariate: male patients tended to have a stronger association between T cells and fucosylation (FIG. 14I).

The data indicate that melanoma fucosylation positively correlates with increased intratumoral CD3$^+$ T cells in mice and humans. Melanoma fucosylation can be increased by L-fuc, which significantly suppresses tumor growth and increases TILs—particularly CD3$^+$ T cells. Although CD4$^+$ and CD8$^+$ T cells were the most increased TIL, subpopulation, their functional requirement for tumor suppression and how increased fucosylation mechanistically triggers increases in CD4$^+$ vs. CD8$^+$ T cells and other TILs were unclear.

Figures 16A, 16B, 16C, 16D, 16E, 16F:
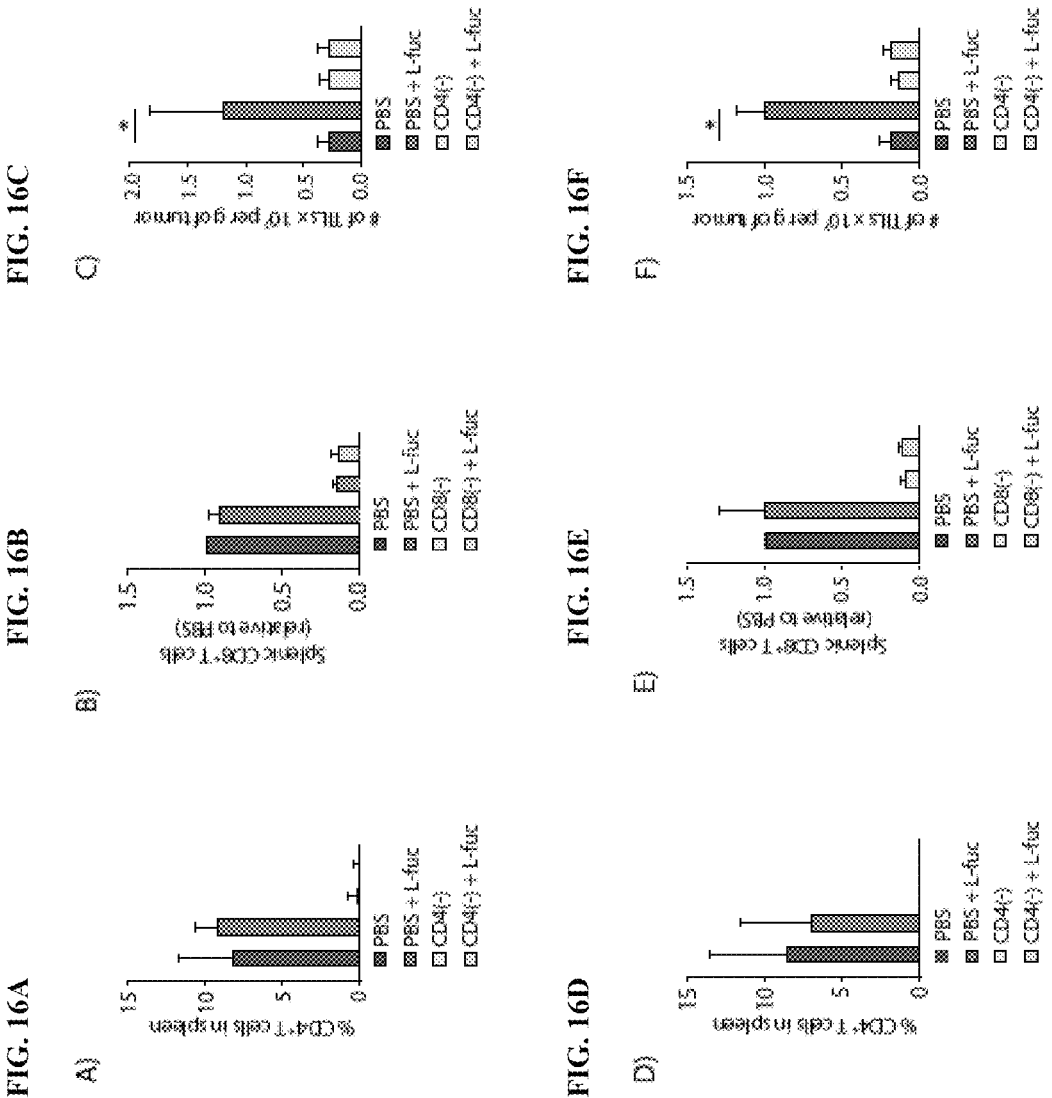

(2) CD4$^+$ T Cells are Central for L-Fucose-Triggered Tumor Suppression and Increases in Intratumoral NK, Dendritic, and CD8$^+$ T Cells To delineate the requirement and roles for each subpopulation, we immunodepleted CD8$^+$ or CD4$^+$ T cells in the SW1 model (depletion was confirmed by splenic profiling, FIGS. 16A & 16B). Consistent with the tumor suppression observed in FIG. 15A, L-fuc reduced tumor growth by ~60% in control mice (FIG. 17A). Although CD8$^+$ T cell depletion generally increased tumor sizes by ~25%, L-fuc still reduced tumor growth by ~50% in CD8$^+$ T cell-depleted mice, indicating that CD8$^+$ T cells are not central mediators of L-fuc/fucosylation-associated tumor suppression (FIG. 17B). In contrast, depletion of CD4$^+$ T cells completely abrogated tumor suppression and the increase in total TILs induced by L-fuc, indicating that CD4$^+$ T cells play an essential role in L-fuc-triggered tumor suppression (FIGS. 17C and 16C).

CD4$^+$ T cells can recruit/activate key anti-tumor TILs, including NK cells, DCs, and CD8$^+$ T cells, which can suppress melanomas and which we observed to be increased by tumor fucosylation (FIG. 15). Therefore, we examined if depletion of CD4$^+$ T cells alters intratumoral populations of these potentially anti-tumor TILs during L-fuc supplementation. Whereas in control mice, L-fuc increased intratumoral NK, DC, and CD8$^+$ T cell subpopulations by ~3-, ~10-, and ~10-fold, respectively, these increases were completely blunted in tumors of CD4$^+$ T cell-depleted mice, indicating that CD4$^+$ T cells are required for induction of intratumoral NK, DC, and CD8$^+$ T cells by L-fuc (FIG. 17D).

We next verified the role of CD4$^+$ T cells in L-fuc-triggered suppression of BRAF-mutant melanoma by CD4$^+$ or CD8$^+$ T cell immunodepletion using the SMI model (depletion was confirmed by splenic profiling (FIGS. 16D & 16E)). Immunodepletion of CD4$^+$ not CD8$^+$ T cells abrogated L-fuc-triggered suppression of the SMI tumors (FIGS. 17E-17G), as well as increases in total TILs and intratumoral NK, DC, and CD8$^+$ T cells (FIGS. 16F and 17H).

The data indicate that CD4$^+$ T cells are required for L-fuc-triggered increases in TILs, and ultimately, in suppression of both NRAS- and BRAF-mutant melanomas. However, the underlying molecular mechanism was unknown. That mFUK expression alone resulted in smaller tumors with increased TILs (FIGS. 15J-15L) indicated that tumor-specific fucosylation—tumor-specific fucosylated protein(s)—is sufficient to trigger anti-tumor immune responses.

(3) HLA-DRB1 is Expressed, Fucosylated, and Required for L-Fucose-Triggered Increased TIL Abundance and Melanoma Suppression To determine the underlying mechanism, we performed proteomic profiling to identify fucosylated immunoregulatory proteins that contribute to fucosylation-triggered, CD4$^+$ T cell-mediated melanoma suppression. We subjected purified fucosylated proteins from control, FUK-overexpressing (to increase fucosylation), or FUK-knockdown (to decrease fucosylation) WM793 BRAF$^{V600E}$ human melanoma cells to liquid chromatography mass spectrometric (LC-MS) analysis (FIG. 18A, left) followed by Ingenuity Pathway Analysis (Qiagen, Redwood City, CA) to identify immunoregulatory pathways with fucosylated components. Of the top 20 functional pathways identified, "Antigen presentation pathway" was the only immunoregulatory pathway (FIG. 18A, upper right). Of the 5 potentially fucosylated components identified in this pathway, the MHC-I protein HLA-A and the MHC-II protein HLA-DRB1 were the only antigen presentation-related and plasma membrane proteins (FIG. 18A, lower right). Based on these findings and known roles of HLA-A and HLA-DRB1 in modulating T cell activity, we next studied the potential fucosylation and role(s) of HLA-A and HLA-DRB1 in fucosylation-triggered anti-melanoma immunity. We first confirmed their expression in human primary melanocyte and melanoma cell lines by immunoblot (IB) analysis (FIG. 19A). Although HLA-DRB1 is generally expressed in antigen-presenting immune cells, the findings are consistent with reports that HLA-DRB1 is also expressed in melanoma.

To verify the fucosylation of HLA-A and HLA-DRB1, we performed lectin pulldown (LPD) assays using agarose-bound *Aleuria aurantia* (AAL) and *Ulex europaeus* agglutinin I (UEA1) lectins, which exhibit binding affinities to α(1,2) and α(1,3/6) fucose linkages, respectively. HLA-A and HLA-DRB1 were both bound by AAL lectin (and to a lesser extent, UEA1 lectin) in melanoma cells (FIG. 19B). The LPD assays, which were performed in cell line pairs derived from patient-matched primary tumor and metastases (WM793 and 1205Lu, and WM115 and WM266-4), indicate that fucosylation of both proteins was reduced in the metastatic cell lines, consistent with findings of reduced fucosylation during metastatic progression (ref. 18). However, these data do not delineate if each protein is directly fucosylated or not (instead interacting with fucosylated, lectin-interacting partners). To determine if HLA-A or HLA-DRB1 are directly fucosylated, we immunoprecipitated and subjected ectopically expressed, V5-tagged HLA-A or HLA-DRB1 to IB analysis using AAL. AAL did not recognize HLA-A but did recognize HLA-DRB1 protein bands (FIG. 19C, left and right), indicating that HLA-DRB1, but not HLA-A, is directly fucosylated in melanoma. However, their potential roles in this context remained unclear.

To determine the potential contribution of HLA-A or HLA-DRB1 to fucosylation-triggered anti-tumor responses, we knocked down the C3H/HeN mouse orthologs of HLA-A and HLA-DRB1, H2K1 and EB1, respectively, in SW1 tumors (FIG. 18B, left & right) and assessed their growth and TIL, profiles in vivo. Consistent with FIG. 15A, L-fuc reduced control knockdown tumor growth by ~60% (FIG. 19D). Overall tumor growth was suppressed by H2K1 knockdown, regardless of L-fuc (FIG. 19E), consistent with roles for MHC-I proteins in protecting against NK cell-mediated anti-tumor activities. However, knockdown of EB1 completely abrogated L-fuc-triggered tumor suppression, indicating that HLA-DRB1/EB1 is crucial for fucosylation-triggered tumor suppression (FIG. 19F). Similar to the CD4+ T cell depletion models (FIGS. 17D & 17H), loss of EB1 reduced total TILs induced by L-fuc, including intratumoral DCs, CD8+ and CD4+ T cells (FIGS. 19G & 19H).

Together, the data demonstrate that HLA-DRB1 is expressed, fucosylated, and required for L-fuc-triggered TIL, induction and melanoma suppression. However, where it is fucosylated and how fucosylation regulates HLA-DRB1 to trigger anti-melanoma immunity and tumor suppression was unclear.

(4) Fucosylation of HLA-DRB1 at N48 Increases its Cell Surface Presentation and is Required for L-Fucose-Triggered Tumor Suppression To study how fucosylation regulates HLA-DRB1, we first mapped its fucosylation site(s). We implemented glycosylation prediction software NetNGlyc and NetOGlyc, which predicted the following 2 glycosylation-fucosylation sites: 1 N-linked site at Arg48 (N48) and 1 O-linked site at Thr129 (T129), which are conserved within constant regions of both human and mouse MHC-II orthologs (FIG. 20A, upper). We performed structural modeling of known HLA-DRB1 interactions with HLA-DM or CD4/TCR to infer structural/functional implications of these sites (PyMOL Molecular Graphics System, Version 2.0 Schrödinger, LLC) (FIG. 20A, lower left and lower right, respectively). Neither site is expected to affect peptide loading/presentation. Glycosylation-fucosylation at N48 is not anticipated to affect HLA-DRB1 interaction interfaces in either complex. Whereas T129 is not on the DRB1: CD4 binding interface, it is on the α and β chain interface of HLA-DRB1, and its fucosylation can affect MHC-II complex assembly.

To determine if HLA-DRB1 is fucosylated at N48 or T129 or both, we subjected V5-tagged HLA-DRB1 purified from WM793 cells to nano-LC/MS, which identified the HLA-DRB1 peptide fragment FLEYSTSECHFENGTER (residues 4-20 of SEQ ID NO: 21) as N-glycosylated on N48, containing the predicted fucosylated glycan HexNAc (4) Hex (3) Fuc (1) (FIG. 20B). To further verify the fucosylation of HLA-DRB1 at N48 or T129, we mutated these amino acids to Gly or Ala, respectively, to abolish its ability to be N- or O-linked fucosylated, respectively. We subjected wild-type (WT), or N48G or T129A "fucomutant"

HLA-DRB1 (ectopically expressed in WM793 cells) to AAL LPD. The N48G fucomutant did not bind to AAL compared with WT or T129A fucomutant HLA-DRB1, (FIG. 20C). These data confirm that HLA-DRB1 is fucosylated at N48 on an N-linked glycan.

To determine how fucosylation regulates HLA-DRB1, we first assessed the subcellular localization of endogenous HLA-DRB1, an expected determinant of its immunoregulatory function, in WM793 cells treated with dimethylsulfoxide (DMSO; control) or 2F-peracteyl-fucose (FUTi; to inhibit fucosyltransferase activity and decrease global fucosylation). Whereas it appeared generally diffuse and up to the edges of DMSO-treated cells, HLA-DRB1 immunostaining was less intense and more centrally co-localized with the endoplasmic reticulum in FUTi-treated cells (FIG. 20D), indicating that fucosylation affects HLA-DRB1 protein levels and/or dispersal throughout the cell and to the surface. We next quantitatively assessed if fucosylation regulates HLA-DRB1 protein levels and/or localization—and importantly—its cell surface abundance in a panel of melanoma cells (WM793, 1205Lu, WM115, WM266-4, WM1366, and WM164) that were pharmacologically modulated for fucosylation. We first confirmed modulation of fucosylation using flow cytometry; in contrast to DMSO, cell surface fucosylation was suppressed or increased (variably, depending on the cell line) using FUTi or L-fuc, respectively (FIGS. 20E & 21A, upper). Flow cytometric analyses revealed that cell surface HLA-DRB1 was reduced and increased by FUTi and L-fuc, respectively, correlating directly with cell surface fucosylation (FIGS. 20E & 21A, upper middle). In contrast, qRT-PCR and IB analyses revealed that neither HLA-DRB1 mRNA nor protein levels were altered by modulation of fucosylation (FIGS. 20E & 21A, lower middle & lower, respectively), indicating that fucosylation does not impact HLA-DRB1 mRNA or protein levels. Rather, it promotes HLA-DRB1 abundance at the cell surface, which is required for immunoregulatory function. Thus, we next tested whether fucosylation of HLA-DRB1 affects TIL induction and tumor suppression.

(5) N48 Fucosylation of HLA-DRB1 is Required for Dietary L-Fucose-Triggered TIL Induction and Tumor Suppression To study how HLA-DRB1 fucosylation affects TILs and tumor suppression, we generated a mouse fucomutant HLA-DRB1 (EB1). The human N48 fucosylation site is conserved in mouse EB1 at N46 (FIG. 20A, upper), which we mutated to Gly (N46G). We reconstituted EB1-knocked-down SW1 cells (from FIG. 19F) with empty vector (shEB1+EV), EB1 WT (shEB1+WT), or EB1 N46G (shEB1+N46G). Non-targeting shRNA knocked-down (shNT) cells (from FIG. 19D) reconstituted with EV (shNT+EV) served as controls. Expression and fucosylation of EB1 WT, and EB1 N46G in the shEB1 cells was confirmed by IB and LPD analyses, respectively (FIG. 21B, upper and lower). We grafted these modified cells into C3H/HeN mice, which we supplemented with or without L-fuc and monitored for tumor growth. The ~60% growth suppression by L-fuc in control tumors was abrogated by loss of EB1 in shEB1+EV tumors (FIG. 20F upper left and upper right, respectively), again supporting the requirement of EB1 for L-fuc-triggered tumor suppression (FIGS. 19D & 19F). In contrast, shEB1+WT tumors exhibited >60% reduced growth in L-fuc-fed mice, indicating that reconstitution with EB1 WT restored tumor suppression (FIG. 20F, lower left). Notably, L-fuc did not suppress shEB1+N46G tumors, similar to shEB1+EV tumors, indicating that glycosylation-fucosylation at N46 is essential for tumor suppression (FIG. 20F, lower right).

To assess the role that HLA-DRB1 fucosylation plays in TIL induction, we profiled total TIL and TIL subpopulations of the shNT and shEB1 tumors. shEB1 abrogated L-fuc-triggered induction of total TIL counts and TIL subpopulations (FIGS. 21C & 21D, respectively), consistent with the earlier shEB1 model (FIGS. 19G & 19H). However, whereas reconstitution of shEB1 tumors with EB1 WT restored TIL induction by L-fuc, reconstitution with EV or EB1 N46G did not (FIGS. 21C & 21D).

These data demonstrate that the expression and glycosylation-fucosylation of HLA-DRB1 at N48 is a key mechanism underlying L-fuc-triggered increases in TIL and suppression of melanoma tumors.

(6) Oral L-Fucose can Enhance Anti-PD1-Mediated Melanoma Suppression 147. Anti-melanoma immunotherapies, such as anti-PD1 are limited by TIL abundance. MHC-II expression in melanomas has recently been reported to correlate with increased anti-PD1 responsiveness, indicating functional contribution. We found a consistent >30% reduction in cell surface MHC-II (including HLA-DRB1) but not MHC-I levels in tumors of melanoma patients who failed anti-PD1 therapy (FIG. 22A). As the data demonstrate that L-fuc can increase cell surface HLA-DRB1 and trigger CD4$^+$ T cell-mediated TIL increases and tumor suppression, we sought to explore (i) how L-fuc can be combined with anti-PD1 to augment efficacy, and (ii), potential prognostic utility of melanoma fucosylation/fucosylated HLA-DRB1 in the context of anti-PD1.

Figures 23A, 23B, 23C, 23D:
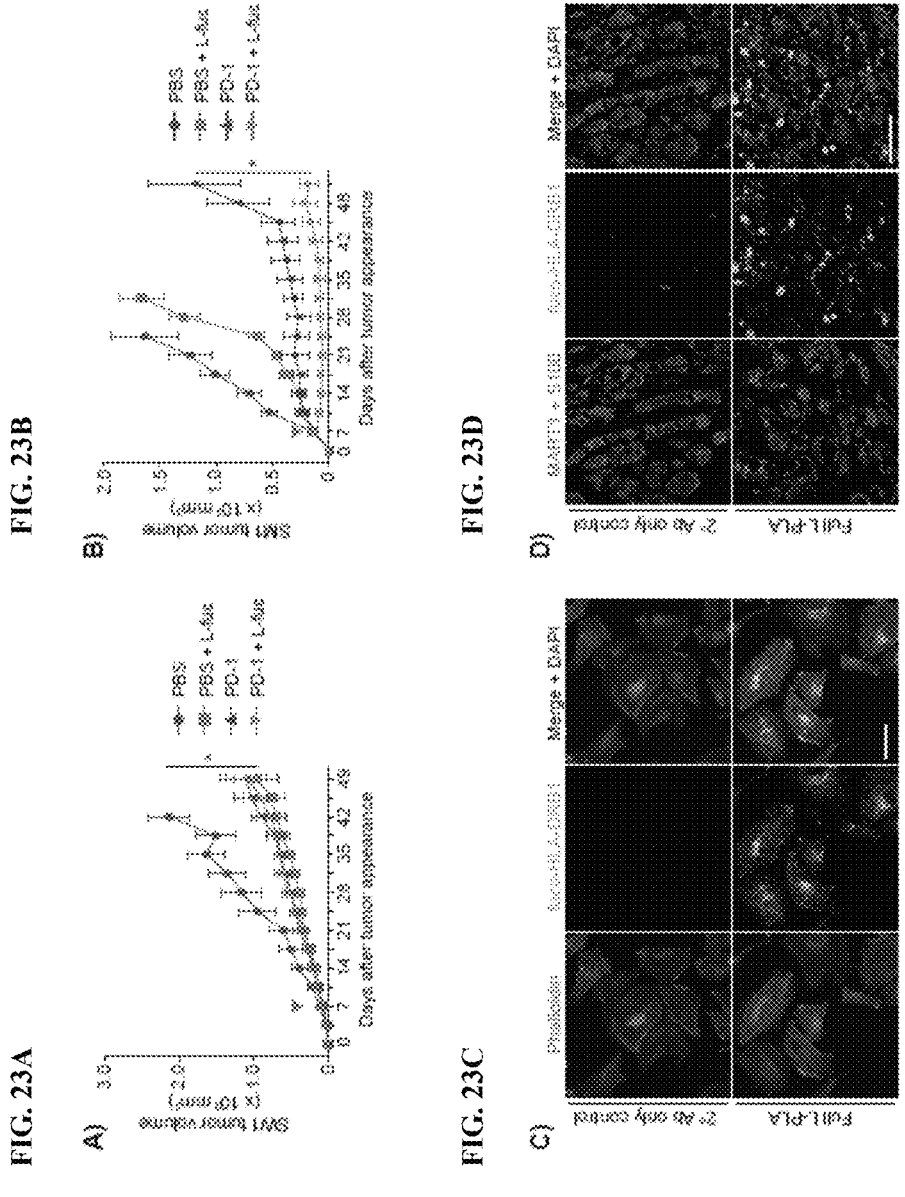

We tested if L-fuc could enhance anti-PD1 efficacy using the SW1 and SM1 models. Consistent with the earlier SW1 model in FIG. 15, L-fuc suppressed SW1 tumor growth ~50-60%. Although co-administration of L-fuc and anti-PD1 did not elicit additive tumor suppression, L-fuc alone suppressed the tumors as much as anti-PD1 (FIG. 23A). In the SM1 model, tumors growth was suppressed >50% for 21 days by L-fuc and >70% for 45 days by anti-PD1 but progressed quickly thereafter. Strikingly, co-administration of L-fuc and anti-PD1 completely suppressed the tumors, with no observable progression even after day 48 (FIG. 23B). These data indicate that in some contexts, L-fuc can suppress melanomas as effectively as anti-PD1, whereas in others, it can enhance anti-PD1. Although reasons underlying the discrepancies are not known, we sought to determine if fucosylated HLA-DRB1 or tumor fucosylation exhibit clinical utility as prognostic biomarkers for melanoma and anti-PD1 responsiveness.

(7) Visualization of Melanoma Fucosylation and Fucosylated HLA-DRB1 as Prognostic Biomarkers for Anti-PD1 Responsiveness Whereas tumor fucosylation status can be readily assessed for prognostic value by staining with fluorescently conjugated AAL (or other lectins), there are currently no antibody reagents against fucosylated species of specific proteins. To overcome this limitation, we modified conventional proximity ligation analysis (PLA) technique, which is used to immunofluorescently stain for 2 proteins that interact or are in close proximity, to visualize fucosylated species of specific proteins (e.g., fucosylated HLA-DRB1) (FIG. 22B). We developed this technique, lectin-mediated PLA (L-PLA), using coverslip-grown WM793 cells, which revealed that endogenous fucosylated HLA-DRB1 exhibits speckled diffuse localization throughout the cell (FIG. 23C), consistent with the observation that fucosylation promotes similar dispersal of HLA-DRB1 throughout the cell and at the cell surface (FIGS. 20D & 20E and 21A). This staining was lost in cells treated with FUTi, confirming specificity of the fucosylated HLA-DRB1 signal (FIG. 22C). We next validated its application on de-identified formalin-fixed paraffin-embedded (FFPE) melanoma patient sections (FIG. 23D).

Figure 23E:
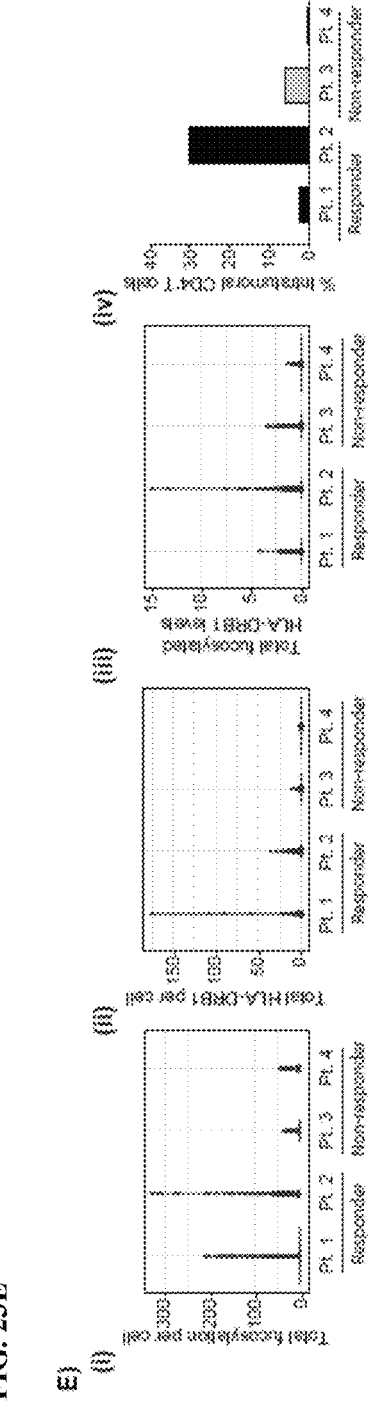

Based on the ability to immunostain for fucosylated HLA-DRB1 in patient FFPE specimens, we tested if total vs. fucosylated HLA-DRB1 or tumor-specific fucosylation correlates with survival outcomes of anti-PD1 treated melanoma patients. To this end, we sought patients who represent poor or good responders to single agent anti-PD1. We defined poor or "non-responders" as patients exhibiting <6 months progression-free survival (PFS) and "responders" as patients exhibiting >2 years PFS on anti-PD1. We identified 2 responders and 2 non-responders with pre-treatment FFPE tumor sections for testing. We performed blinded staining of tumor fucosylation, total HLA-DRB1, fucosylated HLA-DRB1, and CD4$^+$ T cells on the sections, followed by scanning, single cell segmentation, and quantitative imaging analysis. The melanoma cells of both responders exhibited increased fucosylation levels, as well as a trend of increased total DRB1 levels, compared to the non-responders (FIGS. 23Ei & 23Eii). Although only 1 of the 2 responders exhibited increased levels of fucosylated HLA-DRB1 compared with the non-responders (FIG. 23Eiii), this trend matched that of intratumoral CD4$^+$ T cell counts (FIG. 23Eiv). Likely, as-of-yet undefined biological determinants (e.g., variable tumor burden, pre-existing immunological pathologies, co-morbidities, etc.) confound the correlation of these markers. Although limited patient numbers preclude statistical significance in the test, the matching trends in increased tumor fucosylation and total HLA-DRB1, as well as the matching trends in fucosylated HLA-DRB1 and CD4$^+$ T cell counts, support future study with larger patient cohorts to clarify and aid in the development of these potential prognostic biomarkers for melanoma and responsiveness to anti-PD.

b) Discussion

Lack of responsiveness or development of resistance to current immunotherapies is a major hurdle for the effective treatment of melanomas and other cancers types. Although it is clear that insufficient anti-tumor TILs and/or overabundance of tumor-promoting, immunosuppressive TILs can significantly impair immunotherapeutic efficacy, safe and effective methods that overcome these limitations remain to be developed. Advancing the understanding of mechanisms regulating interactions between tumor and immune cells is expected to help overcome these challenges.

We report that the oral administration of the non-toxic dietary sugar L-fuc boosts TIL, abundance and triggers striking melanoma suppression as a monotherapeutic agent and context-specific enhancer of anti-PD1 efficacy. The data reveal that anti-tumor immunity can be induced by increasing melanoma fucosylation, by dietary or by genetic manipulation. In mouse models, L-fuc or expression of mFuk increased TILs by ~10-50-fold, where CD8$^+$ and CD4$^+$ T cells were the most significantly increased subpopulations. TMA analysis confirmed that, consistent with the mouse models, tumor fucosylation positively correlates with intratumoral CD3$^+$ T cell density in human melanomas. We further delineated the essential role that CD4$^+$ T cells play in L-fuc-triggered TIL, induction and tumor suppression. We identified the MHC-II protein HLA-DRB1 as expressed and fucosylated in melanoma and demonstrated that N-linked fucosylation at N48 regulates its cell surface presentation, which is crucial for anti-tumor immunity in vivo. We found context-specific enhancement of anti-PD1 efficacy by L-fuc: in a NRAS-mutant mouse model, L-fuc suppressed tumors as well as anti-PD1; in a BRAF-mutant mouse model, L-fuc was less effective than anti-PD1 but elicited striking additive tumor suppression when administered in combination. Importantly, we developed a novel technique for the immunofluorescent detection of fucosylated species of specific proteins which overcomes a long-standing technical hurdle in the study of glycosylated proteins. Although additional studies with increased patient numbers and statistical power are required, the initial testing indicates that tumor fucosylation and fucosylated HLA-DRB1 have potential for further development as prognostic biomarkers of responsiveness to anti-PD1.

These findings build on a growing body of evidence pointing to key roles of tumor-expressed MHC-II proteins—in this case, HLA-DRB1—in increased responsiveness to anti-PD1. Here, we report the ability to increase cell surface HLA-DRB1 levels using L-fuc. This has significant therapeutic implications, as indicated by the mouse models, which revealed equivalent or additive tumor suppression when L-fuc is administered alone or in combination with anti-PD1. However, the utility of L-fuc as a therapeutic agent and the prognostic value of tumor fucosylation/fucosylated HLA-DRB1 require further elucidation.

Intriguingly, fucosylation was reported to stabilize cell surface PD1 in T cells, and FUTi treatment of $CD8^+$ T cells enhanced their tumor suppression in an OT-I mouse melanoma model, indicating that fucosylation can suppress T cells by enhancing the PD1-mediated immune checkpoint. We did not find that modulating fucosylation alters cell surface PD1 ligand PD-L1 in human or mouse melanoma cells (FIG. 22D), indicating that despite potentially increased cell surface PD1 in $CD8^+$ T cells, the PD1 checkpoint is not functional or predominant in the context of systemic L-fuc. Moreover, fucosylation of TCR was reported to be required for $CD4^+$ T cell activation in in vitro and in vivo FUT8-knockout models of colitis. Importantly, both studies focused on core fucosylation, a FUT8-specific type of fucosylation, whereas oral L-fuc is expected to increase fucosylation subtypes mediated by all 13 mammalian FUTs. Two key interpretations can be drawn from these findings: (i) core vs. non-core fucosylation elicit divergent immunoregulatory effects, and (ii), fucosylation elicits divergent effects on $CD4^+$ vs. $CD8^+$ T cells.

Consistent with the first interpretation, artificial fucosylation of $CD8^+$ T cells using FUT7, which mediates non-core fucosylation, was reported to enhance tumor-homing and anti-tumor activity in mouse models of leukemia, breast cancer, and melanoma. We found that TCR-dependent activation of human peripheral $CD4^+$ T cells ex vivo was associated with increased fucosylation by ~2.75-fold (FIG. 22E). Importantly, $CD4^+$ T cell activation (as indicated by IFNγ production) was reduced ~26% by FUTi and increased ~37% by L-fuc (FIG. 22F). The findings are consistent with both interpretations and indicate that TCR-dependent $CD4^+$ T cell activation can be modulated by manipulating fucosylation, where boosting all subtypes of fucosylation using L-fuc promotes activation.

The discrepant degrees of tumor suppression resulting from single vs. combinatorial L-fuc and anti-PD1 between the SW1 and SMI models (FIGS. 23A & 23B) points to key differences between the models, which represent potential determinants of therapeutic L-fuc and tumor fucosylation/fucosylated HLA-DRB1 as prognostic biomarkers. First, SW1 and SMI are NRAS- and BRAF-mutant melanomas, respectively, raising possible divergent contributions of different driver mutations. Second, based on their origins, SW1 cells were grafted into female mice, whereas SMI cells were grafted into male mice. Thus, the discrepancies can be due to sex-dependent differences—a notion that is consistent with the TMA data showing more significant correlation between tumor fucosylation and intratumoral $CD3^+$ T cell counts in male patients (FIG. 14I). This is also consistent with the disproportionate lethality rate in male melanoma patients—in 2020, the total estimated ~6,850 melanoma deaths in the United States comprises more than twice as many male (4,610) than female (2,240) patients (American Cancer Society Facts and Figures, 2020).

L-fucose has been explored as an experimental treatment for Leukocyte Adhesion Deficiency II, a genetic disorder of fucosylation that presents with developmental retardation, impaired infection responses, and pathological accumulation of peripheral leukocytes due to impaired extravasation. Symptoms of this disorder can be mitigated by L-fuc supplementation without significant co-morbidities, setting a precedent of therapeutic safety for L-fuc. Currently, lack of GMP-grade L-fuc is a logistical hurdle for clinical trials. However, there exists a potentially safe alternative: fucoidan, a commercially available L-fuc polymer-containing seaweed extract. Fucoidan has been safely consumed for decades for anecdotal health benefits; clinically, fucoidan supplementation in healthy human subjects and patients with pathologies, including HTLV-1 and hepatitis C, has been reported with few co-morbidities. Notably, fucoidan elicits anti-tumor effects in a number of different cancer types, although the mechanism(s) are unclear. Further studies are needed to determine if fucoidan elicits similar anti-tumor immunological effects as L-fuc and can be administered as a safe, relatively inexpensive immunotherapeutic agent for the treatment of melanoma (and other cancers).

In conclusion, we have identified a mechanism by which oral administration of the non-toxic dietary sugar L-fuc can increase cell surface HLA-DRB1, triggering $CD4^+$ T cell-mediated anti-melanoma immunity and significant tumor suppression. Further studies elucidating determinants of this mechanism are expected to expand the understanding of the immunobiology of melanoma and other cancer types and to inform future efforts in maximizing the utility of fucosylation/fucosylated HLA-DRB1 as biomarkers and of L-fuc as an anti-cancer therapeutic.

c) Methods (1) Cell Culture

WM793, 1205Lu, A375, WM1366, WM164, and SW1 melanoma cells were obtained from the Ronai laboratory (Sanford-Burnham Prebys Medical Discovery Institute (La Jolla, CA), WM983A/B cells were purchased from Rockland Immunochemicals (Limerick, PA). WM115 and WM266-4 cells were purchased from ATCC (Manassas, VA). SMI (Gift from the Smalley Laboratory at Moffitt), were cultured in Dulbecco's Modified Eagle Medium containing 10% fetal bovine serum (FBS), 1 g/ml, glucose, 4 mM L-glutamine in 37° C. in 5% $CO_2$. Cell lines were transfected using Lipofectamine 2000 (Invitrogen, Waltham, MA). Primary $CD4^+$ T cells were harvested using the EasySep (StemCell Technologies) Human $CD4^+$ negative selection isolation kit (#17952) according to manufacturer's protocols.

(2) Antibodies

160. The following antibodies were used as indicated: mouse anti-V5 (0.2 μg/ml. Millipore Sigma (St. Louis, MO)), mouse anti-V5 gel (V5-10, Millipore Sigma (St. Louis, MO)), mouse anti-human HLA-DRB1 (0.2 μg/mL, IF, ab215835, Abcam (Cambridge, UK)), rabbit anti-human HLA-DRB1 (0.2 μg/ml. WB, ab92371, Abcam (Cambridge, UK)), β-tubulin (0.3 μg/mL, E7, developed by M. Mccutcheon and S. Carroll and obtained from Developmental Studies Hybridoma Bank (University of Iowa, Iowa City, IA)), goat anti-biotin (0.1 μg/ml. Vector Labs (Burlingame, CA)), biotinylated AAL (0.4 μg/ml, Vector Labs, Burlingame, CA), fluorescein-conjugated AAL (0.4 μg/ml. Vector Laboratories, Burlingame, CA), Agarose UEA1 and AAL (Vector Laboratories, (Burlingame, CA)), anti-mouse CD4 (20 mg/kg, for immunodepletion, GK1.5, Bioxcell (West Lebanon, NH)), anti-mouse CD8 (20 mg/kg, for immunodepletion, 2.43, Bioxcell (West Lebanon, NH)), goat anti-mouse horseradish peroxidase (HRP) (0.04 μg/mL, Santa Cruz Biotechnology (Dallas, TX)), goat anti-mouse HRP (0.04 μg/mL, Santa Cruz Biotechnology (Dallas, TX)), goat anti-rabbit AlexaFluor 488 (0.04 μg/mL, ThermoFisher Scientific (Waltham, MA)),), donkey anti-mouse AlexaFluor 594 (0.05 μg/mL, ThermoFisher Scientific (Waltham, MA)), AlexaFluor 594 donkey anti-rabbit (0.05 g/mL, ThermoFisher Scientific (Waltham, MA)), rabbit anti-Mart1 (0.2 μg/mL, Millipore Sigma (St. Louis, MO), rabbit anti-S100 (0.2 g/mL, Agilent Technologies (Santa Clara, CA)), APC anti-mouse CD3 (0.5 μg/mL, BD Biosciences (San Jose, CA)), Pacific Blue anti-mouse CD4 (0.5 μg/mL, BD Biosciences (San Jose, CA)), BV785 anti-mouse CD8 (0.5 μg/mL, BD Biosciences (San Jose, CA)), FITC anti-mouse F4/80 (0.5 μg/mL, BD Biosciences (San Jose, CA)), PerCP anti-mouse GR-1 (0.5 g/mL, BD Biosciences (San Jose, CA)), PeCy7 anti-mouse CD11c (0.5 μg/mL, BD Biosciences (San Jose, CA)), PE anti-mouse NK1.1 (0.5 μg/mL, BD Biosciences (San Jose, CA)), PE anti-mouse DX5 (0.5 μg/mL, BD Biosciences (San Jose, CA)), PerCP-Cy5.5 anti-mouse CD11b (0.5 μg/mL, BD Biosciences (San Jose, CA)), rabbit anti-human PD-L1 (clone #NBP1-76769; Noveus Biologicals, Centennial, CO), PE rat anti-mouse PD-L1 (clone #10F.9G2; (Biolegend, (San Diego, CA)), and phalloidin Alexafluor 488 (0.2 μg/mL, ThermoFisher Scientific (Waltham, MA)), mouse anti-FLAG (0.2 μg/mL, clone M2, Millipore Sigma (St. Louis, MO)), rabbit anti-HLA-A (0.2 μg/mL, Proteintech (Rosemont, IL)), normal mouse IgG (Santa Cruz Biotechnology (Dallas, TX)), rabbit anti-KDEL (0.1 μg/mL, ThermoFisher Scientific (Waltham, MA)), mouse anti-PD1 (for in vivo studies, 20 mg/kg, clone #RMP1-14 Bioxcell (West Lebanon, NH)), donkey anti-goat plus PLA secondary antibody (Millipore Sigma (St. Louis, MO)), donkey anti-mouse plus PLA secondary antibody (Millipore Sigma (St. Louis, MO)), mouse anti-actin (0.2 μg/mL clone JLA, developed by M. Mccutcheon and S. Carroll and obtained from Developmental Studies Hybridoma Bank (University of Iowa, Iowa City, IA)), rat anti-mouse CD8 antibody (0.2 μg/mL, ThermoFisher Scientific (Waltham, MA)), AlexaFluor 568 goat anti-rat secondary antibody (0.05 μg/mL, ThermoFisher Scientific (Waltham, MA)), anti-CD3 (0.2 μg/mL, Clone PSI, Santa Cruz Biotechnology (Dallas, TX).

(3) Proteomic Mass Spectrometric Profiling of Fucosylated Proteins

WM793 cells stably transduced with pLenti-GFP empty vector (EV), pLenti-FUK-GFP, or shFUK were grown in triplicate to ~30-40% confluence in (3×15 cm³ plates each). The cells were further cultured in the presence of 50u M L-fucose-alkyne for ~72 h to ~80% confluence. The cells were lysed in 1.5% N-dodecyl-beta-D-maltoside/20 mM HEPES pH 7.4/protease and phosphatase inhibitors. Lysates were sonicated and cleared by centrifugation at full speed for 5 min at 4 C. Lysates were acetone precipitated overnight. The pelleted proteins were resuspended and subjected to click-chemistry labeling with biotin-azide using the Click-It kit per manufacturer's protocol (Invitrogen). For negative control, pLenti-GFP-EV cells were not labeled with L-fucose-alkyne but were lysed, pelleted, and click-reacted with biotin-azide. All biotin-azide (biotinylated-fucosylated) samples were pulled down using neutravidin beads that were pre-blocked with 2% IgG-free BSA. Samples were submitted to the Sanford-Burnham Prebys proteomics core facility for on-bead digest; supernatants from on-bead digest were analyzed by LC/MS/MS. Hits that were increased by >1.5 fold in pLenti-FUK-GFP-expressing cells and unchanged or decreased in pLenti-EV-GFP-expressing cells or decreased in pLenti-shFUK-expressing cells. Hits were subjected to Ingenuity Pathway Analysis (Qiagen).

(4) Lectin Pulldown

Control beads and AAL or UEA1 lectin-conjugated agarose beads (Vector Laboratories (Burlingame, CA)) were pre-blocked for 2 h in blocking buffer (2% IgG-Free BSA (Jackson ImmunoResearch Laboratories (Westgrove, PA)) on a rotator at 4° C. Cells were lysed on ice in 1% Triton-X100 lysis buffer (1% Triton-X100, 20 mM Tris-HCl, pH 7.4, 150 mM NaCl in ddH2O+protease and phosphatase inhibitors (ThermoFisher Scientific (Waltham, MA)), briefly sonicated, pelleted, and the resulting lysates were normalized in protein concentration to the sample with the lowest concentration and diluted to a final 0.25% Triton-X-100 with dilution buffer (0) % Triton X-100, 20 mM Tris-HCl, pH 7.4, 150 mM NaCl in ddH₂O+protease and phosphatase inhibitors (ThermoFisher Scientific (Waltham, MA)), and incubated with 15 μl of pre-blocked beads (beads were spun out of block and resuspended in dilution buffer) and rotated overnight at 4° C. Next, the beads were washed twice with dilution buffer and subjected to (12%) SDS-PAGE and IB analysis using the indicated antibodies.

(5) Mass Spectral Analysis of Glycosylation on HLA-DRB1

Stained bands of approximately lug of exogenously expressed HLA-DRB1 purified from WM793 cells were cut into 1-mm³ pieces and reduced and alkylated using 20 mM TCEP (tris(2-carboxyehtyl)phosphine) and iodoacetamide in 50 mM Tris-HCl. The gel pieces were washed in a 20 mM ammonium phosphate solution with 50% methanol overnight at 4° C. The following day, the gel pieces were dehydrated for 30 minutes with 100% acetonitrile. After gel pieces were completely dry, trypsin protease solution was added to the samples (300 ng trypsin). Samples were digested for 4 hours at 37° C. The digests were applied to a C-18 Zip-Tip and eluted with 50% methanol and 0.1% formic acid. Five microliters of the elution were diluted in 0.1% formic acid and then injected into a Q-Exactive Orbitrap mass spectrometer (ThermoFisher Scientific, (Waltham, MA)) equipped with an Easy nano-LC HPLC system with reverse-phase column (ThermoFisher Scientific, (Waltham, MA)). A binary gradient solvent system consisting of 0.1% formic acid in water (solvent A) an 90% acetonitrile and 0.1% formic acid in water (solvent B) was used to separate peptides. Raw data files were analyzed using both Proteome Discoverer v2.1 (ThermoFisher Scientific, (Waltham, MA)) with Byonic (Protein Metrics) as a module and Byonic standalone v2.10.5. All extracted ion chromatograms (EICs) were generated using Xcalibur Qual Browser v4.0 (ThermoFisher Scientific, (Waltham, MA)). UniProt sequence Q5Y7D1_Human was used as the reference sequence for peptide analysis.

(6) TIL Isolation Protocol

Tumors of SW1 or SMI melanoma cells from C3H/HeJ or C57BL/6 mice, respectively) were digested using 1× tumor digest buffer (0.5 mg/ml. Collagenase I, 0.5 mg/ml. Collagenase IV, 0.25 mg/ml. Hyalyronidase V. 0.1 mg/ml. DNAse I in HBSS (Millipore Sigma (St. Louis, MO)). Tumors were homogenized using the Miltenyi MACs dissociator. Red blood cells were lysed using ACK lysis buffer (Life Technologies, (Grand Island, NY)). Tumor homogenate cells were counted using a standard hemocytometer.

(7) Flow Cytometry (a) TIL Profiling:

Single-cell suspensions from tumor and spleen tissue were stained with Live/Dead Zombie NIR (Biolegend, (San Diego, CA)) at 1:1,000 in PBS for 20 min. Cell suspensions were spun down and stained with the following antibodies: APC anti-mouse CD3 (0.5 μg/mL, BD Biosciences (San Jose, CA)), Pacific Blue anti-mouse CD4 (0.5 g/mL, BD Biosciences (San Jose, CA)), BV785 anti-mouse CD8 (0.5 μg/mL, BD Biosciences (San Jose, CA)), PerCP anti-mouse CD25 (0.5 g/mL, BD Biosciences (San Jose, CA)), FITC anti-mouse F4/80 (0.5 μg/mL, BD Biosciences (San Jose, CA)), PeCy7 anti-mouse CD11c (0.5 μg/mL, BD Biosciences (San Jose, CA)), PE anti-mouse NK1.1 (0.5 μg/mL, BD Biosciences (San Jose, CA)), PE anti-mouse DX5 (0.5 μg/mL, BD Biosciences (San Jose, CA)), PerCP-Cy5.5 anti-mouse CD11b (0.5 μg/mL, BD Biosciences (San Jose, CA)). After staining, the cells were washed and fixed (2% formaldehyde), followed by another wash and flow cytometric analysis. The compensation controls were prepared using 0.5 μg/ml. of each antibody with beads UltraComp eBeads™, (ThermoFisher Scientific (Waltham, MA)). All samples were subject to flow cytometric analysis using a LSR Flow Cytometer (BD Biosciences (San Jose, CA)). Flow cytometric data was further analyzed using FlowJo™ analysis software (BD Biosciences (San Jose, CA)). TIL profiles were determined as a measure of TIL subpopulations per gram of tumor tissues or % of total splenocytes.

(b) Assment of Cell Surface Pan-MHC-I and Pan-MHC-II:

Homogenates from resected metastatic melanomas of anti-PD1 naïve patients (n=6) and patients who failed anti-PD1 therapy (n=13) were subject to flow cytometric analysis, where CD45⁻/CD90⁻/EpCAM⁻ tumor cells were subgated and assessed for pan-MHC-I or pan-MHC-II positivity (based on FMO samples for each marker). Each data point represents.

(8) Assment of Cell Surface Fucosylation, HLA-DRB1, and PD-L1

Indicated cells were treated for 72 h with DMSO, 250 μM fucosyltransferase inhibitor (FUTi) (Millipore Sigma (St. Louis, MO)), or 250 μM of L-fucose (Biosynth (Oak Terrace, IL)). After 72 h, cells were stained with 0.1 μM PKH26 (Millipore Sigma (St. Louis, MO)) prior to fixation in 4% formaldehyde solution. The cells were stained with anti-HLA-DRB1 (rabbit anti-human HLA-DRB1 (0.2 μg/mL, ab92371, Abcam (Cambridge, UK)) and fluorescein AAL (0.2 μg/ml. Vector Labs (Burlingame, CA)), or anti-human or anti-mouse PD-L1 (Novus Biologicals (Centennial, CO) or Biolegend (San Diego, CA), respectively) overnight. The following day the cells were washed 3 times prior to adding AlexaFluor 594 donkey anti-rabbit (0.8 μg/mL, ThermoFisher Scientific (Waltham, MA)). Cells were washed 3 times and then subject to flow cytometric analyses using a FACSCalibur™ (BD Biosciences (San Jose, CA)). Samples were analyzed using FlowJo™ analysis software (BD Biosciences (San Jose, CA)). Median values of DRB1 and AAL were normalized to PKH26 values and statistical analysis was performed using GraphPad Prism™.

(9) Immunoprecipitation and Immunoblot Analyses

Cells were lysed on ice in RIPA lysis buffer (25 mM Tris-HCl pH 7.6, 150 mM NaCl, 5 mM EDTA, 1% NP-40 or 1% Triton X-100, 1% sodium deoxycholate, 0.1% SDS in diH₂O+protease and phosphatase inhibitors (ThermoFisher Scientific (Waltham, MA)), briefly sonicated, pelleted, and the resulting lysates were normalized by protein concentration using DC assay (BioRad Laboratories, (Hercules, CA)). The indicated samples were subjected to (12%) SDS-PAGE and immunoblot analysis using the indicated antibodies. Immunoblot imaging and analysis was performed using either an Odyssey FC scanner and ImageStudio (LiCor Biosciences, Lincoln, NE) or film.

(10) qPCR

RNA from cells subjected to the indicated treatments was extracted using Gene Elute Mammalian Total RNA Extraction System (Millipore Sigma (St. Louis, MO)). RNA was reversed transcribed to cDNA using High-Capacity cDNA Reverse Transcription Kit (ThermoFisher Scientific (Waltham, MA)). qRT-PCR analysis was performed using FastStart Universal SYBR Green Master Mix (Rox) (Roche Diagnostics, (Indianapolis, IN)) using a BioRad CFX96 Real-time system (BioRad Laboratories, (Hercules, CA)). The qRT-PCR cycles used were as follows: 95° C. for 10 min, 35 cycles of 95° C. for 15 seconds, 55° C. for 60 seconds, and 72° C. for 30 seconds. Expression of the indicated genes was normalized to histone H3A expression. Primers (listed in table 1) for qRT-PCR were generated using NCBI primer blast software (National Center for Biotechnology Information (Washington, D.C.)).

Table 1: Primers

(11) Fluorescent Immunocytochemical and Immunohistological Staining and Analysis (a) General Fluorescent Immunocytochemical Staining Protocol Melanoma cells were grown on German glass coverslips (Electron Microscopy Services (Hatfield, PA)) and fixed in fixation buffer (4% formaldehyde, 2% sucrose in phosphate buffered saline (PBS) for 20 min at room temperature (RT). The coverslip-grown cells were subject to two 5-min standing washes in PBS prior to permeabilization in permeabilization buffer (0.4% Triton-X-100 and 0.4% IgG-free bovine serum albumin (BSA, Jackson ImmunoResearch Laboratories (Westgrove, PA) in PBS) for 20 min at RT. The coverslip-grown cells were next subject to 2 PBS washes and incubated with the indicated primary antibodies.

(b) General Fluorescent Immunohistochemical Staining Protocol

In general, paraffin-embedded FFPE tumor tissue sections (or the TMA slide) were melted at 70° C. for 30 min. The slides were further de-paraffinizeded using xylene and rehydrated in serial alcohol washes. The slides were pressure cooked at 15 PSI for 15 min in a 1×DAKO antigen retrieval buffer (Agilent Technologies (Santa Clara, CA)). The tumor sections were subject to two 5-min standing washes in PBS prior to blocking in 1× Carb-Free Blocking Solution (Vector Labs (Burlingame, CA)) for 2-3h. The slides were next washed twice and incubated with indicated lectin and/or antibodies.

(c) Immunofluorescent Staining and Analysis of Melanoma TMA (FIG. 15N)

(i) Immunostaining

Melanoma TMA (Serial #ME1002b; US BioMax, Inc. (Derwood, MD)) was immunostained with FITC-conjugated AAL lectin (0.4 μg/mL, Vector Laboratories (Burlingame, CA)), rabbit anti-Mart1 (0.2 μg/mL, Millapore Sigma (St. Louis, MO)), and rabbit anti-S100 (0.2 μg/mL, Agilent Technologies (Santa Clara, CA)), and anti-CD3 (0.2 μg/mL, Clone PS1, Santa Cruz Biotechnology (Dallas, TX)) followed by AlexaFluor 568 (Cy3) donkey anti-rabbit and AlexaFluor 647 (Cy5) donkey anti-mouse secondary antibodies (0.05 μg/mL, ThermoFisher Scientific (Waltham, MA). The slides were mounted with VECTASHIELD®+ DAPI (Vector Laboratories (Burlingame, CA)).

(ii) Analysis

The multiplex fluorescence TMA image file was imported into Definiens Tissue Studio version 4.7 (Definiens AG, Munich, Germany), where individual cores were identified using the software's automated TMA segmentation tool. First, nucleus segmentation (DAPI channel) and cell growth algorithms were used to segment individual cells within each core. A minimum size threshold was used to refine the cell segmentation. Next, mean fluorescence intensity (MFI) values for the FITC (fucosylation), Cy3 (melanoma markers Mart1+S100) and Cy5 (CD3 marker) channels were extracted from each segmented cell and minimum thresholds for MFI was set to enumerate positive Cy3 and Cy5 cells. Identical thresholds were used for each core. Finally average MFI values for each core were reported for the FITC and Cy3 channels.

Melanoma-specific fucosylation (FITC in CY3-positive cells) MFI and $CD3^+$ cell numbers were subject to statistical analyses and correlation with clinical parameters as follows: We used the nonparametric Wilcoxon rank sum test to compare melanoma-specific fucosylation levels between $CD3^+$ T cells high vs low groups. The density values of $CD3^+$ T cells were all log 2 transformed in the statistical analysis. Multivariable linear regression was used to assess the association between fucosylation and T cells while adjusting for confounding factors including sex, age and stage. The Spearman correlation coefficient was used to measure the correlation between melanoma-specific fucosylation and T cells in different sex groups.

(d) Immunofluorescent Confirmation of Splenic $CD8^+$ T Cells (FIGS. 16B & 16E):

FFPE mouse tumor sections were immunostained with rat anti-mouse CD8 antibody (0.2 μg/mL, ThermoFisher Scientific (Waltham, MA)), followed by AlexaFluor 568 goat anti-rat secondary antibody (0.05 μg/mL, ThermoFisher Scientific (Waltham, MA)). The slides were mounted with VECTASHIELD®+DAPI (Vector Laboratories (Burlingame, CA)). Microscopy images were acquired using a Keyence BZ-X710 microscope (Osaka, Japan) and processed and analyzed using FIJI (NIH).

(e) Immunofluorescent Analysis of AAL on SW1/SM1/ SW1+EV/mFuk Tumors (FIGS. 14A, 14D, & 14G)

FFPE mouse tumor sections were immunostained with FITC-conjugated AAL lectin (0.4 μg/mL, Vector Laboratories (Burlingame, CA)), rabbit anti-Mart-1 (0.2 μg/mL, Millipore Sigma (St. Louis, MO), and rabbit anti-S100 (0.2 μg/mL, Agilent Technologies (Santa Clara, CA)), followed by AlexaFluor 594 donkey anti-rabbit secondary antibody (0.05 μg/mL, ThermoFisher Scientific (Waltham, MA)). The slides were mounted with VECTASHIELD®+DAPI (Vector Laboratories (Burlingame, CA)). Microscopy images were acquired using a Keyence BZ-X710 microscope (Osaka, Japan), and images were measured for AAL-positive signal within MARTI-/S 100-positive regions (designated as melanoma regions of interest) using FIJI software (NIH). Statistical analysis was performed using GraphPad Prism™ (San Diego, CA).

(12) Lectin-Mediated Proximity Ligation Assay (L-PLA)

Coverslip-grown cells subjected to L-PLA were processed upfront as described in the fluorescent immunocytochemistry protocol detailed above, whereas FFPE tumor tissue sections were processed according to the fluorescent immunohistochemistry protocol detailed above. Both approaches used mouse-anti-HLA-DRB1 (applied at 0.2 μg/mL, ab215835, Abcam, Cambridge, UK), biotinylated AAL, lectin (applied at 0.2 μg/mL, Vector Laboratories (Burlingame, CA)), on coverslips overnight in 4° C. The coverslip-grown cells were again washed twice with PBS followed and then incubated with phalloidin Alexafluor 488 (applied at 0.05 μg/mL, ThermoFisher Scientific (Waltham, MA) with goat anti-biotin (applied at 0.1 μg/mL, Vector Laboratories (Burlingame, CA)) for 2h in 4° C. Subsequent steps of the protocol were adapted from the DUOlink In Situ Green PLA kit's manufacturer's protocol (Millipore Sigma (St. Louis, MO)). PLA anti-goat MINUS and PLA anti-mouse PLUS probes were applied at 1:5 for 1 h at 37° C. The coverslips were washed twice with Wash Buffer A prior to ligation with 1:5 ligation buffer and 1:40 ligase in ddH2O for 30 min at 37° C. The coverslips were washed twice with wash buffer A prior to incubation in amplification mix (1:5 amplification buffer and 1:80 polymerase in ddH2O for 1.5 h at 37° C.). Coverslips were washed twice with Wash Buffer B prior to mounting to slide with DAPI with VECTASHIELD® (Vector Labs, Burlingame, CA). Microscopy images were acquired using a Keyence BZ-X710, and images were process and analyzed using FIJI (NIH).

(a) Immunofluorescent Analysis of Anti-PD1-Treated Melanoma Patients (FIG. 23E)

The indicated FFPE sections were L-PLA stained as detailed above with the addition of anti-$CD4^+$ antibody. The scanned tumor images were processed using InForm (PerkinElmer, Waltham, MA) and HALO (indica labs, Albuquerque, NM). For each whole tumor images, (i) every individual melanoma marker (MARTI+S100)-positive cell was segmented and quantitatively measured for total fucosylation, total HLA-DRB1, and fucosylated HLA-DRB1, and (ii) every CD4+ T cell within the melanoma marker-positive tissue region was counted. Per patient (Pt.), these marker values were box plotted to visualize the staining distribution of individual tumor cells. The total numbers of melanoma cells per patient section measured and analyzed were as follows: Pt. 1:557, 146 cells; Pt. 2:743, 172 cells; Pt. 3:95, 628 cells; and Pt. 4:13, 423 cells.

(13) Mouse Models

Four-to-six-week-old female C3HeN and male C57BL6 mice were purchased from Charles Rivers Laboratories for the indicated experiments. Four-to-six-week-old male NSG mice from the Lau laboratory breeding colony were used for the indicated experiments. Mice were housed in the Comparative Medicine Facility at H. Lee Moffitt Cancer Center and Research Institute. Mouse tumor volumes were measured using length, width and depth divided by 2. Generally, 10 mice were assigned to each indicated treatment cohort, and $1 \times 10^6$ melanoma cells were subcutaneously injected into the right rear flanks of the recipient mice. At each experimental endpoint, mice were humanely euthanized using $CO_2$ inhalation in accordance to the American Veterinary Medical Association guidelines. Mice were observed daily and humanely euthanized if the tumor reached 2,000 $mm^3$ or mice showed signs of metastatic disease. All experiments were approved by the Institutional Animal Care and Use Committee (IACUC) in accordance with the National Research Council guidelines.

(a) Control Vs. mFuk±L-Fucose Models (FIG. 15)

SW1 or SMI mouse melanoma cells were injected into syngeneic C3H/HeN (or NSG) female or C57BI/6 male mice, respectively. Cells were injected as follows: parental SW1 cells for FIG. 15A; parental SMI cells for FIG. 15E; SW1 cells stably expressing either empty vector (EV) or mouse fucose kinase (mFuk) for FIG. 15L; and parental SW1 cells for FIG. 15M. Between 7-14 days, when the mice tumors reached ~150 $mm^3$, the mice were either supplemented with or without 100 mM L-fucose (Biosynth (Oak Terrace, IL.)) via drinking water, which was provided ad libitum. When the tumors reached ~2 cm³, the animals were sacrificed, and the tumors either processed for flow cytometric profiling or for histological analysis as indicated.

(b) Immunodepletion Mouse Models (FIG. 17)

Three days prior to tumor engraftment, PBS (control) or ~300 μg α-CD4 (20 mg/kg, for immunodepletion, GK1.5, Bioxcell (West Lebanon, NH)) or α-CD8 (20 mg/kg, for immunodepletion, 2.43, Bioxcell (West Lebanon, NH)) was administered by intraperitoneal injection into the indicated cohorts of mice. Injections of immunodepletion antibody or PBS were continued every 3-4 days until endpoint. Syngeneic recipient C3H/HeN female or C57BL/6 male mice were injected with SW1 or SMI cells, respectively. After approximately 7 days, when the tumors reached ~150 mm³, the mice were either supplemented with or without 100 mM L-fucose (Biosynth (Oak Terrace, IL)) via drinking water, which was provided ad libitum. When the tumors reached ~2 cm³, the animals were sacrificed, and the tumors were either processed for flow cytometric profiling or for histological analysis as indicated.

(c) HLA-A/HLA-DRB1 Knockdown and Fucomutant H2-EB1 Reconstitution Mouse Model (FIGS. 19 & 20 Models):

SW1 mouse melanoma cells expressing either shNT (nontargeting shRNA), shH2K1, shEB1, shNT+EV, shEB1+EV, shEB1+EB1 WT, or shEB1+EB1 N46G were injected into syngeneic C3H/HeN female mice. After approximately 7 days, when the mice tumors reached ~150 mm³, the mice were either supplemented with or without 100 mM L-fucose (Biosynth (Oak Terrace, IL)) via drinking water, which was provided ad libitum. When the tumors reached ~2 cm³, the animals were sacrificed, and the tumors were either processed for flow cytometric profiling or for histological analysis as indicated (d) Anti-PD-1 Mouse Model (FIG. 23 Models)

SW1 or SM1 mouse melanoma cells were injected into syngeneic C3H/HeN female or C57BL/6 male mice, respectively. After approximately 7 days, when the mice tumors reached ~150 mm³, the mice were either supplemented with or without 100 mM L-fucose (Biosynth (Oak Terrace, IL)) via drinking water, which was provided ad libitum. Simultaneously, the mice were injected either with PBS (control) or anti-PD1 (20 mg/kg, clone RMP1-14, Bioxcell (West Lebanon, NH)) every 3-4 days until endpoint. When the tumors reached ~2 cm³, the animals were sacrificed.

(e) NSG Melanoma Model (FIG. 15 Model)

SW1 murine mouse melanoma cells were subcutaneously injected into the right rear flanks of NSG mice. After 7 days, when the tumors reached ~150 mm³, the mice were either supplemented with or without 100 mM L-fucose (Biosynth (Oak Terrace, IL)) via drinking water, which was provided ad libitum. When the tumors reached 2 cm³, the animals were sacrificed.

(14) CD3/CD28 Human CD4⁺ T Cell Activation Assay/ ELISA

Human CD4⁺ T cells were isolated from fresh PBMC using a CD4⁺ T cell negative selection isolation kit (Stem Cell Technologies, (Vancouver CA)) according to manufacturer's protocols. CD4⁺ T cells were cultured in the presence of DMSO, 250 μM FUTi (Millapore Sigma (St. Louis, MO)), or 250 μM L-fucose 3 days prior to activation. After 3 days, the CD4⁺ T cells were activated using anti-CD3/ CD28 Dynabeads (ThermoFisher Scientific (Waltham, MA)) in a 1:1 bead: CD4⁺ T cell ratio. After 24 h, supernatants were collected and IFNγ ELISA was performed according to manufacturer's protocols (Biolegend (San Diego, CA)).

D. References

1. Abe, S., et al. Safety evaluation of excessive ingestion of mozuku fucoidan in human. *J Food Sci* 78, T648-651 (2013).
2. Alam, M. S. Proximity Ligation Assay (PLA). *Curr Protoc Immunol* 123, e58 (2018).
3. Alatrash, G., et al. Fucosylation Enhances the Efficacy of Adoptively Transferred Antigen-Specific Cytotoxic T Lymphocytes. *Clin Cancer Res* 25, 2610-2620 (2019).
4. Araya, N., et al. Fucoidan therapy decreases the proviral load in patients with human T-lymphotropic virus type-1-associated neurological disease. *Antivir Ther* 16, 89-98 (2011).
5. Barber, L. D., et al. Unusual uniformity of the N-linked oligosaccharides of HLA-A, -B, and -C glycoproteins. *J Immunol* 156, 3275-3284 (1996).
6. Becker, D. J. & Lowe, J. B. Fucose: biosynthesis and biological function in mammals. *Glycobiology* 13, 41R-53R (2003).
7. Chacon, J. A., et al. Manipulating the tumor microenvironment ex vivo for enhanced expansion of tumor-infiltrating lymphocytes for adoptive cell therapy. *Clin Cancer Res* 21, 611-621 (2015).
8. Chang, C. S., Brossay, L., Kronenberg, M. & Kane, K. P. The murine nonclassical class I major histocompatibility complex-like CD1.1 molecule protects target cells from lymphokine-activated killer cell cytolysis. *J Exp Med* 189, 483-491 (1999).
9. Choi, S. S., et al. Safety evaluation of the human-identical milk monosaccharide, 1-fucose. *Regul Toxicol Pharmacol* 72, 39-48 (2015).
10. Etzioni, A. & Tonetti, M. Fucose supplementation in leukocyte adhesion deficiency type II. *Blood* 95, 3641-3643 (2000).
11. Gellrich, F. F., Schmitz, M., Beissert, S. & Meier, F. Anti-PD-1 and Novel Combinations in the Treatment of Melanoma—An Update. *J Clin Med* 9 (2020).
12. Hodis, E., et al. A landscape of driver mutations in melanoma. *Cell* 150, 251-263 (2012).
13. Hsu, H. Y. & Hwang, P. A. Clinical applications of fucoidan in translational medicine for adjuvant cancer therapy. *Clin Transl Med* 8, 15 (2019).
14. Johnson, D. B., et al. Melanoma-specific MHC-II expression represents a tumour-autonomous phenotype and predicts response to anti-PD-1/PD-L1 therapy. *Nat Commun* 7, 10582 (2016).
15. Kennedy, R. & Celis, E. Multiple roles for CD4+ T cells in anti-tumor immune responses. *Immunol Rev* 222, 129-144 (2008).
16. Knight, D. A., et al. Host immunity contributes to the anti-melanoma activity of BRAF inhibitors. *J Clin Invest* 123, 1371-1381 (2013).
17. Kramer, A., Green, J., Pollard, J., Jr. & Tugendreich, S. Causal analysis approaches in Ingenuity Pathway Analysis. *Bioinformatics* 30, 523-530 (2014).
18. Lau, E., et al. The transcription factor ATF2 promotes melanoma metastasis by suppressing protein fucosylation. *Sci Signal* 8, ra124 (2015).
19. Lenertz, L. Y., et al. Mutation of putative N-linked glycosylation sites on the human nucleotide receptor P2X7 reveals a key residue important for receptor function. *Biochemistry* 49, 4611-4619 (2010).

20. Liang, W., et al. Core Fucosylation of the T Cell Receptor Is Required for T Cell Activation. *Front Immunol* 9, 78 (2018).

21. Maletzki, C., et al. NSG mice as hosts for oncological precision medicine. *Lab Invest* 100, 27-37 (2020).

22. Marquardt, T., et al. Correction of leukocyte adhesion deficiency type II with oral fucose. *Blood* 94, 3976-3985 (1999).

23. Marth, J. D. & Grewal, P. K. Mammalian glycosylation in immunity. *Nat Rev Immunol* 8, 874-887 (2008).

24. Mori, N., Nakasone, K., Tomimori, K. & Ishikawa, C. Beneficial effects of fucoidan in patients with chronic hepatitis C virus infection. *World J Gastroenterol* 18, 2225-2230 (2012).

25. Okada, M., et al. Blockage of Core Fucosylation Reduces Cell-Surface Expression of PD-1 and Promotes Anti-tumor Immune Responses of T Cells. *Cell Rep* 20, 1017-1028 (2017).

26. Orczyk-Pawilowicz, M., Augustyniak, D., Himle, L. & Katnik-Prastowska, I. Lectin-based analysis of fucose and sialic acid expressions on human amniotic IgA during normal pregnancy. *Glycoconj J* 30, 599-608 (2013).

27. Pandey, A., et al. Glycosylation of Specific Notch EGF Repeats by O-Fut1 and Fringe Regulates Notch Signaling in *Drosophila*. *Cell Rep* 29, 2054-2066 e2056 (2019).

28. Raulet, D. H., et al. Specificity, tolerance and developmental regulation of natural killer cells defined by expression of class I-specific Ly49 receptors. *Immunol Rev* 155, 41-52 (1997).

29. Rillahan, C. D., et al. Global metabolic inhibitors of sialyl- and fucosyltransferases remodel the glycome. *Nat Chem Biol* 8, 661-668 (2012).

30. Rock, K. L., Reits, E. & Neefjes, J. Present Yourself! By MHC Class I and MHC Class II Molecules. *Trends Immunol* 37, 724-737 (2016).

31. Rodig, S. J., et al. MHC proteins confer differential sensitivity to CTLA-4 and PD-1 blockade in untreated metastatic melanoma. *Sci Transl Med* 10 (2018).

32. Rossjohn, J., et al. T cell antigen receptor recognition of antigen-presenting molecules. *Annu Rev Immunol* 33, 169-200 (2015).

33. Rubio, G., et al. Cross-linking of MHC class I molecules on human NK cells inhibits NK cell function, segregates MHC I from the NK cell synapse, and induces intracellular phosphotyrosines. *J Leukoc Biol* 76, 116-124 (2004).

34. Spitzer, M. H., et al. Systemic Immunity Is Required for Effective Cancer Immunotherapy. *Cell* 168, 487-502 e415 (2017).

35. Steentoft, C., et al. Precision mapping of the human O-GalNAc glycoproteome through SimpleCell technology. *EMBO J* 32, 1478-1488 (2013).

36. Stern, L. J., et al. Crystal structure of the human class II MHC protein HLA-DR1 complexed with an influenza virus peptide. *Nature* 368, 215-221 (1994).

37. Talmadge, J. E. & Fidler, I. J. Enhanced metastatic potential of tumor cells harvested from spontaneous metastases of heterogeneous murine tumors. *J Natl Cancer Inst* 69, 975-980 (1982).

38. Topalian, S. L., et al. Melanoma-specific CD4+T lymphocytes recognize human melanoma antigens processed and presented by Epstein-Barr virus-transformed B cells. *Int J Cancer* 58, 69-79 (1994).

39. Tsiakas, K., et al. Mutation of the glycosylated asparagine residue 286 in human CLN2 protein results in loss of enzymatic activity. *Glycobiology* 14, 1C-5C (2004).

40. Wang, Y., et al. Biological Activities of Fucoidan and the Factors Mediating Its Therapeutic Effects: A Review of Recent Studies. *Mar Drugs* 17 (2019).

41. Weber, J. S., et al. Nivolumab versus chemotherapy in patients with advanced melanoma who progressed after anti-CTLA-4 treatment (CheckMate 037): a randomised, controlled, open-label, phase 3 trial. *Lancet Oncol* 16, 375-384 (2015).

42. Wei, W., et al. Molecular mechanisms of missense mutations that generate ectopic N-glycosylation sites in coagulation factor VIII. *Biochem J* 475, 873-886 (2018).

What is claimed is:

1. A method of modulating major histocompatibility complex II human lymphocyte antigen (HLA)-DRB1 expression on the surface of a cell, comprising contacting the cell with an agent that modulates the amount of fucosylation on the cell;

wherein an increase in fucosylation increases surface expression of HLA-DRB1; and wherein a decrease in fucosylation decreases the surface expression of HLA-DRB1.

2. The method of claim 1, wherein the agent that modulates fucosylation comprises an agent that increases fucosylation, wherein the agent that increases fucosylation comprises a fucose selected from L-fucose, D-fucose, fucose-1-phosphate, or GDP-L-fucose; or wherein the agent that modulates fucosylation comprises an agent that decreases fucosylation, wherein the agent that decreases fucosylation comprises 2-fluoro-fucose (FUTi).

3. A method of increasing the activation of CD4$^+$ T cells, comprising contacting the CD4$^+$ T cells with an agent that increases the amount of fucosylation;

wherein the agent that increases the amount of fucosylation comprises L-fucose; and wherein an increase in fucosylation increases CD4$^+$ T cell activation.

4. A method of enhancing the efficacy of CD4$^+$ T cell mediated therapy to treat a cancer in a subject, comprising administering to the subject a fucose; and wherein the CD4$^+$ T cell therapy is reliant on MHC class II HLA-DRB1 antigen presentation.

5. The method of claim 4, wherein the fucose is selected from L-fucose, D-fucose, fucose-1-phosphate, or GDP-L-fucose.

6. The method of claim 4, wherein the CD4$^+$ T cell mediated therapy comprises an immune checkpoint blockade inhibitor.

7. The method of claim 4, wherein the fucose is administered before and/or during administration of the CD4$^+$ T cell mediated therapy.

8. The method of claim 4, wherein the cancer is a melanoma.

9. A method of increasing the number of tumor infiltrating lymphocytes (TILs) or marrow infiltrating lymphocytes (MILs) in a cancer microenvironment in a subject, comprising administering to the subject an agent that increases the amount of fucosylation.

10. A method of increasing the efficacy of an immune checkpoint inhibitor therapy to treat a cancer in a subject, comprising administering to the subject an agent that increases the amount of fucosylation.

11. The method of claim 10, wherein the cancer is a melanoma.

12. A method of treating, inhibiting, decreasing, reducing, and/or ameliorating a cancer or metastasis in a subject, comprising administering to the subject (a) an immune checkpoint inhibitor, and (b) an agent that increases the amount of fucosylation.

13. The method of claim 12, wherein the agent that increases fucosylation comprises a fucose selected from L-fucose, D-fucose, fucose-1-phosphate, or GDP-L-fucose.

14. The method of claim 12, wherein the cancer is a melanoma.

15. The method of claim 12, further comprising the steps of:

(i) harvesting TILs, CAR T cells, and/or MILs;

(ii) contacting the TILs, CAR T cells, and/or MILs of step (i) with the agent that increases fucosylation; and (iii) administering to the subject the TILs, CAR T cells, and/or MILs of step (ii) that have been contacted with the agent.

16. A method of increasing the efficacy of a TIL and/or MIL therapy to treat a cancer in a subject, comprising administering to the subject an agent that increases the amount of fucosylation.

17. The method of claim 16, wherein the agent that increases fucosylation comprises a fucose, and wherein the fucose is administered before resection of TILs.

18. The method of claim 17, further comprising administering to the subject the fucose during ex vivo processing of the TILs.

19. A method of increasing the number of TILs, CAR T cells, and/or MILs ex vivo, comprising contacting the TILs, CAR T cells, and/or MILs with an agent that increases the amount of fucosylation.

20. A method of activating TILs, CAR T cells, and/or MILs ex vivo, comprising contacting the TILs, CAR T cells, and/or MILs with L-fucose.

\* \* \* \* \*

SEQUENCE LISTING

<160> NUMBER OF SEQ ID NOS: 24

<210> SEQ ID NO 1
<211> LENGTH: 45
<212> TYPE: DNA
<213> ORGANISM: Artificial Sequence
<220> FEATURE:
<223> OTHER INFORMATION: Synthetic construct

<400> SEQUENCE: 1
cgcgcgcggg atccatggag cagtcagagg gagtcaattg gactg          45

<210> SEQ ID NO 2
<211> LENGTH: 37
<212> TYPE: DNA
<213> ORGANISM: Artificial Sequence
<220> FEATURE:
<223> OTHER INFORMATION: Synthetic construct

<400> SEQUENCE: 2
cgcgcgcggc tagcggtggt gcccacttca gagggcc          37

<210> SEQ ID NO 3
<211> LENGTH: 38
<212> TYPE: DNA
<213> ORGANISM: Artificial Sequence
<220> FEATURE:
<223> OTHER INFORMATION: Synthetic construct

<400> SEQUENCE: 3
gtctttgaag gatacacagc caccttagga tggactcg                                                    38

<210> SEQ ID NO 4
<211> LENGTH: 32
<212> TYPE: DNA
<213> ORGANISM: Artificial Sequence
<220> FEATURE:
<223> OTHER INFORMATION: Synthetic construct

<400> SEQUENCE: 4
tgagtgtcat ttcttcggtg ggacggagcg gg                                                          32

<210> SEQ ID NO 5
<211> LENGTH: 38
<212> TYPE: DNA
<213> ORGANISM: Artificial Sequence
<220> FEATURE:
<223> OTHER INFORMATION: Synthetic construct

<400> SEQUENCE: 5
cgagtccatc ctaaggtggc tgtgtatcct tcaaagac                                                    38

<210> SEQ ID NO 6
<211> LENGTH: 38
<212> TYPE: DNA
<213> ORGANISM: Artificial Sequence
<220> FEATURE:
<223> OTHER INFORMATION: Synthetic construct

<400> SEQUENCE: 6
gtctttgaag gatacacagc caccttagga tggactcg                                                    38

<210> SEQ ID NO 7
<211> LENGTH: 29
<212> TYPE: DNA
<213> ORGANISM: Artificial Sequence
<220> FEATURE:
<223> OTHER INFORMATION: Synthetic construct

<400> SEQUENCE: 7
cgcgcccggg cgcgccatgg tggtgtggc                                                              29

<210> SEQ ID NO 8
<211> LENGTH: 26
<212> TYPE: DNA
<213> ORGANISM: Artificial Sequence
<220> FEATURE:
<223> OTHER INFORMATION: Synthetic construct

<400> SEQUENCE: 8
cgcgcccgct cgaggctcag gagtcc                                                                 26

<210> SEQ ID NO 9
<211> LENGTH: 28
<212> TYPE: DNA
<213> ORGANISM: Artificial Sequence
<220> FEATURE:
<223> OTHER INFORMATION: Synthetic construct

<400> SEQUENCE: 9
gtgtcatttc tacggcggga cgcagcgc                                                               28

-continued

```
<210> SEQ ID NO 10
<211> LENGTH: 28
<212> TYPE: DNA
<213> ORGANISM: Artificial Sequence
<220> FEATURE:
<223> OTHER INFORMATION: Synthetic construct

<400> SEQUENCE: 10
gcgctgcgtc ccgccgtaga aatgacac                                        28

<210> SEQ ID NO 11
<211> LENGTH: 18
<212> TYPE: DNA
<213> ORGANISM: Artificial Sequence
<220> FEATURE:
<223> OTHER INFORMATION: Synthetic construct

<400> SEQUENCE: 11
aagcagactg ccgcaaat                                                   18

<210> SEQ ID NO 12
<211> LENGTH: 21
<212> TYPE: DNA
<213> ORGANISM: Artificial Sequence
<220> FEATURE:
<223> OTHER INFORMATION: Synthetic construct

<400> SEQUENCE: 12
ggcctgtaac gatgaggttt c                                               21

<210> SEQ ID NO 13
<211> LENGTH: 20
<212> TYPE: DNA
<213> ORGANISM: Artificial Sequence
<220> FEATURE:
<223> OTHER INFORMATION: Synthetic construct

<400> SEQUENCE: 13
acttccgccg agatctgttc                                                 20

<210> SEQ ID NO 14
<211> LENGTH: 20
<212> TYPE: DNA
<213> ORGANISM: Artificial Sequence
<220> FEATURE:
<223> OTHER INFORMATION: Synthetic construct

<400> SEQUENCE: 14
ggatcagtgg acgtaggcag                                                 20

<210> SEQ ID NO 15
<211> LENGTH: 20
<212> TYPE: DNA
<213> ORGANISM: Artificial Sequence
<220> FEATURE:
<223> OTHER INFORMATION: Synthetic construct

<400> SEQUENCE: 15
gaacacgctt cttccttggg                                                 20

<210> SEQ ID NO 16
<211> LENGTH: 21
<212> TYPE: DNA
<213> ORGANISM: Artificial Sequence
<220> FEATURE:
<223> OTHER INFORMATION: Synthetic construct
```

-continued

```
<400> SEQUENCE: 16
caggctcctt acctttctgg t                                              21

<210> SEQ ID NO 17
<211> LENGTH: 16
<212> TYPE: DNA
<213> ORGANISM: Artificial Sequence
<220> FEATURE:
<223> OTHER INFORMATION: Synthetic construct

<400> SEQUENCE: 17
ccgcggacgc tggata                                                    16

<210> SEQ ID NO 18
<211> LENGTH: 18
<212> TYPE: DNA
<213> ORGANISM: Artificial Sequence
<220> FEATURE:
<223> OTHER INFORMATION: Synthetic construct

<400> SEQUENCE: 18
ggcgattcgc gacttctg                                                  18

<210> SEQ ID NO 19
<211> LENGTH: 20
<212> TYPE: DNA
<213> ORGANISM: Artificial Sequence
<220> FEATURE:
<223> OTHER INFORMATION: Synthetic construct

<400> SEQUENCE: 19
ccatagtagc tcagcacccg                                                20

<210> SEQ ID NO 20
<211> LENGTH: 20
<212> TYPE: DNA
<213> ORGANISM: Artificial Sequence
<220> FEATURE:
<223> OTHER INFORMATION: Synthetic construct

<400> SEQUENCE: 20
gtcctgtcct gttctccagc                                                20

<210> SEQ ID NO 21
<211> LENGTH: 31
<212> TYPE: PRT
<213> ORGANISM: Homo sapiens

<400> SEQUENCE: 21

Arg Pro Arg Phe Leu Glu Tyr Ser Thr Ser Glu Cys His Phe Phe Asn
1               5                   10                  15

Gly Thr Glu Arg Val Arg Phe Leu Asp Arg Tyr Phe Tyr Asn Gln
            20                  25                  30

<210> SEQ ID NO 22
<211> LENGTH: 31
<212> TYPE: PRT
<213> ORGANISM: Homo sapiens

<400> SEQUENCE: 22

Arg Pro Arg Phe Leu Glu Tyr Ser Thr Ser Glu Cys His Phe Tyr Asn
1               5                   10                  15

Gly Thr Gln Arg Val Arg Phe Leu Glu Arg Tyr Ile Tyr Asn Arg
```

-continued

```
                 20               25               30

<210> SEQ ID NO 23
<211> LENGTH: 31
<212> TYPE: PRT
<213> ORGANISM: Homo sapiens

<400> SEQUENCE: 23

Val Val Glu Ser Phe Thr Val Gln Arg Arg Val His Pro Lys Val Thr
1               5               10               15

Val Tyr Pro Ser Lys Thr Gln Pro Leu Gln His His Asn Leu Leu
            20               25               30

<210> SEQ ID NO 24
<211> LENGTH: 33
<212> TYPE: PRT
<213> ORGANISM: Homo sapiens

<400> SEQUENCE: 24

Tyr Glu Ile Phe Asp Asn Phe Leu Val Arg Arg Arg Val Glu Pro Thr
1               5               10               15

Val Thr Val Tyr Pro Thr Lys Thr Gln Pro Leu Glu His His Asn Leu
            20               25               30

Leu
```